(12) United States Patent
Clark et al.

(10) Patent No.: US 10,278,572 B1
(45) Date of Patent: May 7, 2019

(54) SPECULUM

(71) Applicant: OBP Medical Corporation, Lawrence, MA (US)

(72) Inventors: Adrienne Clark, Waltham, MA (US); Demetrio Donald Anaya, Somerville, MA (US); Shawn P. Murphy, Bolton, MA (US)

(73) Assignee: OBP Medical Corporation, Lawrence, MA (US)

( * ) Notice: Subject to any disclaimer, the term of this patent is extended or adjusted under 35 U.S.C. 154(b) by 0 days.

(21) Appl. No.: 16/105,153

(22) Filed: Aug. 20, 2018

Related U.S. Application Data

(60) Provisional application No. 62/574,412, filed on Oct. 19, 2017, provisional application No. 62/574,969, (Continued)

(51) Int. Cl.
*A61B 1/32* (2006.01)
*A61B 1/303* (2006.01)

(52) U.S. Cl.
CPC .............. *A61B 1/32* (2013.01); *A61B 1/303* (2013.01)

(58) Field of Classification Search
CPC ....... A61B 1/32; A61B 1/303; A61B 17/0206; A61B 17/02; A61B 2017/2837;
(Continued)

(56) References Cited

U.S. PATENT DOCUMENTS

| 559,122 A | 4/1896 | Daily |
| 2,235,979 A | 3/1941 | Brown |

(Continued)

FOREIGN PATENT DOCUMENTS

| CN | 2239235 Y | 11/1996 |
| CN | 2265156 Y | 10/1997 |

(Continued)

OTHER PUBLICATIONS

Solvey, Techinical Data Sheet, Ixef 1022 polyarylamide, Feb. 13, 2015, pp. 1-5.

(Continued)

*Primary Examiner* — Lynnsy M Summitt
(74) *Attorney, Agent, or Firm* — Cowan, Liebowitz & Latman, P.C.

(57) ABSTRACT

A speculum, comprising a lower member including a handle and a lower blade extending at an angle from the handle, an upper blade movably engaged with the lower member by an angular adjustment mechanism so as to allow continuous adjustment of an angle between the upper and lower blades, and the angular adjustment mechanism comprising: a guiding arm, a rotational lever connected to the upper blade and operable by a user to change the angle between the upper and lower blades, the rotational lever being movably engaged with the guiding arm and configured to move relative to the guiding arm to continuously change the angle between the upper and lower blades, and a locking member movable between a locked position to lock a positional relationship between the rotational lever and the guiding arm and an unlocked position to release a locked positional relationship between the rotational lever and the guiding arm, wherein the locking member is configured to: (1) automatically lock the positional relationship between the rotational lever and the guiding arm along any position on the guiding arm, (2) automatically release the locked positional relationship during operation of the rotational lever in a first direction, and (3) be manually moved to the unlocked position to permit operation of the rotational lever in a second direction opposite to the first direction.

27 Claims, 53 Drawing Sheets

Related U.S. Application Data filed on Oct. 20, 2017, provisional application No. 62/649,190, filed on Mar. 28, 2018.

(58) Field of Classification Search
CPC .......... A61B 17/42; A61B 2017/0256; A61B 1/0684; A61B 1/00105; A61B 1/31
See application file for complete search history.

(56) References Cited

U.S. PATENT DOCUMENTS

| | | |
|---|---|---|
| 2,247,458 A | 6/1941 | Shepard |
| 2,482,971 A | 9/1949 | Golson |
| 2,592,190 A | 4/1952 | Rubens et al. |
| 3,324,850 A | 6/1967 | Gunning et al. |
| 3,332,414 A | 7/1967 | Gasper |
| 3,532,088 A | 10/1970 | Fiore |
| 3,592,199 A | 7/1971 | Ostensen |
| 3,595,222 A | 7/1971 | Vellacott |
| 3,638,644 A | 2/1972 | Reick |
| 3,675,641 A | 7/1972 | Fiore |
| 3,716,047 A | 2/1973 | Moore et al. |
| 3,729,006 A | 4/1973 | Wilder et al. |
| 3,762,400 A | 10/1973 | McDonald |
| 3,769,968 A | 11/1973 | Blount et al. |
| 3,789,835 A | 2/1974 | Whitman |
| 3,815,585 A * | 6/1974 | Fiore .................. A61B 1/32 600/222 |
| 3,826,248 A | 7/1974 | Gobels |
| 3,847,143 A * | 11/1974 | Cotey .................. A61B 1/32 600/220 |
| 3,851,642 A | 12/1974 | McDonald |
| 3,934,578 A | 1/1976 | Heine |
| 3,945,371 A | 3/1976 | Adelman |
| 3,978,850 A | 9/1976 | Moore et al. |
| 4,067,323 A | 1/1978 | Troutner |
| 4,156,424 A | 5/1979 | Burgin |
| 4,210,133 A | 7/1980 | Castaneda |
| 4,226,228 A | 10/1980 | Shin et al. |
| 4,263,899 A | 4/1981 | Burgin |
| 4,300,541 A | 11/1981 | Burgin |
| 4,337,763 A * | 7/1982 | Petrassevich ............ A61B 1/32 600/210 |
| 4,432,351 A | 2/1984 | Hoary |
| 4,492,220 A | 1/1985 | Hayes |
| 4,502,468 A | 3/1985 | Burgin |
| 4,527,553 A | 7/1985 | Upsher |
| 4,546,761 A | 10/1985 | McCullough |
| 4,556,052 A * | 12/1985 | Muller .................. A61B 1/267 600/193 |
| 4,562,832 A | 1/1986 | Wilder |
| 4,566,439 A | 1/1986 | Burgin |
| 4,574,784 A | 3/1986 | Soloway |
| 4,597,383 A | 7/1986 | Van Der Bel |
| 4,607,623 A | 8/1986 | Bauman |
| 4,619,248 A | 10/1986 | Walsh |
| 4,638,792 A | 1/1987 | Burgin |
| 4,766,887 A | 8/1988 | Cecil, Jr. et al. |
| 4,807,600 A | 2/1989 | Hayes |
| 4,884,559 A | 12/1989 | Collins |
| 4,905,670 A | 3/1990 | Adair |
| 4,934,352 A | 6/1990 | Sullivan, Jr. |
| 4,971,036 A | 11/1990 | Collins |
| 5,018,507 A | 5/1991 | Montaldi |
| 5,026,368 A | 6/1991 | Adair |
| 5,054,906 A | 10/1991 | Lyons, Jr. |
| 5,063,908 A | 11/1991 | Collins |
| 5,143,054 A | 9/1992 | Adair |
| 5,165,387 A | 11/1992 | Woodson |
| 5,174,278 A | 12/1992 | Babkow |
| 5,179,937 A | 1/1993 | Lee |
| 5,179,938 A | 1/1993 | Lonky |
| 5,222,271 A | 6/1993 | Eganhouse |
| D337,384 S | 7/1993 | Schucman |
| 5,318,009 A | 6/1994 | Robinson |
| 5,329,938 A | 7/1994 | Lonky |
| 5,427,152 A | 6/1995 | Weber |
| 5,438,976 A | 8/1995 | Nash |
| 5,465,709 A | 11/1995 | Dickie et al. |
| 5,499,964 A | 3/1996 | Beck et al. |
| 5,512,038 A | 4/1996 | O'Neal et al. |
| 5,695,492 A | 12/1997 | Brown |
| 5,716,329 A | 2/1998 | Dieter |
| 5,785,648 A | 7/1998 | Min |
| 5,840,013 A | 11/1998 | Lee et al. |
| 5,846,249 A | 12/1998 | Thompson |
| 5,865,729 A | 2/1999 | Meehan |
| 5,873,820 A | 2/1999 | Norell |
| 5,879,304 A | 3/1999 | Schuchman et al. |
| 5,888,195 A | 3/1999 | Schneider |
| 5,899,854 A | 5/1999 | Slishman |
| 5,916,150 A | 6/1999 | Sillman |
| 6,004,265 A | 12/1999 | Hsu et al. |
| 6,036,638 A | 3/2000 | Nwawka |
| 6,036,713 A | 3/2000 | Kieturakis |
| 6,048,308 A | 4/2000 | Strong |
| 6,080,105 A | 6/2000 | Spears |
| 6,130,520 A | 10/2000 | Wawro et al. |
| 6,176,824 B1 | 1/2001 | Davis |
| 6,186,944 B1 | 2/2001 | Tsai |
| 6,217,512 B1 | 4/2001 | Salo et al. |
| 6,254,247 B1 | 7/2001 | Carson |
| 6,277,067 B1 | 8/2001 | Blair |
| 6,319,199 B1 | 11/2001 | Sheehan et al. |
| 6,346,085 B1 | 2/2002 | Schiffman |
| 6,359,644 B1 | 3/2002 | Salvati |
| 6,361,489 B1 | 3/2002 | Tsai |
| 6,379,296 B1 | 4/2002 | Baggett |
| 6,379,299 B1 | 4/2002 | Borodulin et al. |
| 6,394,111 B1 | 5/2002 | Jacobs et al. |
| 6,394,950 B1 | 5/2002 | Weiss |
| 6,416,465 B2 | 7/2002 | Brau |
| 6,428,180 B1 | 8/2002 | Karram et al. |
| 6,432,045 B2 | 8/2002 | Lemperle et al. |
| 6,432,049 B1 | 8/2002 | Banta |
| 6,436,033 B2 | 8/2002 | Tan |
| 6,450,952 B1 | 9/2002 | Rioux |
| 6,468,206 B1 | 10/2002 | Hipps et al. |
| 6,468,232 B1 | 10/2002 | Ashton-Miller et al. |
| 6,487,440 B2 | 11/2002 | Deckert et al. |
| 6,504,985 B2 | 1/2003 | Parker et al. |
| 6,523,973 B2 | 2/2003 | Galli |
| 6,524,259 B2 | 2/2003 | Baxter-Jones et al. |
| 6,569,091 B2 | 5/2003 | Diokno et al. |
| 6,589,168 B2 | 7/2003 | Thompson |
| 6,595,917 B2 | 7/2003 | Nieto |
| 6,616,603 B1 | 9/2003 | Fontana |
| 6,626,825 B2 | 9/2003 | Tsai |
| 6,663,576 B2 | 12/2003 | Gombrich et al. |
| 6,676,598 B2 | 1/2004 | Rudischhauser et al. |
| 6,719,688 B2 | 4/2004 | Pecherer et al. |
| 6,761,687 B1 | 7/2004 | Doshi |
| 6,830,547 B2 | 12/2004 | Weiss |
| 6,896,653 B1 | 5/2005 | Vail, III et al. |
| 7,014,340 B2 | 3/2006 | Betis |
| 7,029,439 B2 | 4/2006 | Roberts et al. |
| D520,464 S | 5/2006 | Strong |
| 7,223,223 B2 | 5/2007 | Lindsay |
| 7,276,025 B2 | 10/2007 | Roberts et al. |
| 7,306,559 B2 | 12/2007 | Williams |
| 7,631,981 B2 | 12/2009 | Miller et al. |
| 7,736,304 B2 | 6/2010 | Pecherer |
| 7,758,203 B2 | 7/2010 | McMahon et al. |
| 7,909,759 B2 | 3/2011 | Pecherer |
| 7,967,809 B2 | 6/2011 | Jay-Robinson |
| 8,012,089 B2 | 9/2011 | Bayat |
| 8,047,987 B2 | 11/2011 | Grey et al. |
| 8,088,066 B2 | 1/2012 | Grey et al. |
| 8,096,945 B2 | 1/2012 | Buchok et al. |
| 8,142,352 B2 | 3/2012 | Vivenzio et al. |
| 8,142,353 B2 | 3/2012 | Pecherer et al. |
| 8,157,728 B2 | 4/2012 | Danna et al. |
| 8,162,826 B2 | 4/2012 | Pecherer et al. |
| 8,251,898 B2 | 8/2012 | Pecherer |
| 8,317,693 B2 | 11/2012 | Grey et al. |

(56) References Cited

U.S. PATENT DOCUMENTS

| | | | |
|---|---|---|---|
| 8,388,523 B2 | 3/2013 | Vivenzio et al. |
| 8,394,017 B2 | 3/2013 | Kieffer |
| 8,435,175 B2 | 5/2013 | McMahon et al. |
| 8,512,234 B2 | 8/2013 | Grey et al. |
| 8,512,237 B2 | 8/2013 | Bastia |
| 8,555,892 B2 | 10/2013 | Traub |
| 8,596,847 B2 | 12/2013 | Vayser et al. |
| 8,628,879 B2 | 1/2014 | Pecherer et al. |
| 8,821,385 B2 | 9/2014 | Naito |
| D719,652 S | 12/2014 | Swift |
| 8,979,745 B2 | 3/2015 | Swift |
| 9,050,048 B2 | 6/2015 | Nadershahi |
| D745,669 S | 12/2015 | Swift |
| D752,217 S | 3/2016 | Swift |
| D753,295 S | 4/2016 | Vivenzio et al. |
| 9,307,897 B2 | 4/2016 | Swift |
| 9,326,812 B2 * | 5/2016 | Waaler ............... H01M 2/1066 |
| 9,332,898 B2 | 5/2016 | McMahon et al. |
| 9,532,706 B2 | 1/2017 | McMahon et al. |
| 9,629,529 B1 | 4/2017 | Indovina et al. |
| 9,718,130 B1 | 8/2017 | Vayser et al. |
| 9,763,743 B2 | 9/2017 | Lin et al. |
| 9,808,231 B2 | 11/2017 | Miraki et al. |
| 9,814,377 B2 | 11/2017 | Lia et al. |
| 9,820,638 B2 | 11/2017 | Cheng |
| 9,820,729 B2 | 11/2017 | Miles et al. |
| 9,826,892 B2 | 11/2017 | Dresher et al. |
| 9,833,295 B2 | 12/2017 | Vayser et al. |
| 9,844,364 B2 | 12/2017 | Grey et al. |
| 9,861,349 B2 | 1/2018 | Nadershahi et al. |
| 9,867,531 B2 | 1/2018 | Pacey et al. |
| 9,877,639 B2 | 1/2018 | Grey et al. |
| 9,877,644 B2 | 1/2018 | Greenstein et al. |
| D809,660 S | 2/2018 | Nguyen et al. |
| 9,883,792 B2 | 2/2018 | McMahon et al. |
| 9,888,957 B2 | 2/2018 | Wolf et al. |
| 9,907,544 B2 | 3/2018 | Nadershahi et al. |
| 9,913,682 B2 | 3/2018 | Wolf et al. |
| 9,918,618 B2 | 3/2018 | Molnar |
| 9,918,802 B2 | 3/2018 | Coppersmith et al. |
| 9,931,028 B2 | 4/2018 | Lia et al. |
| 9,943,295 B2 | 4/2018 | King |
| 9,949,814 B2 | 4/2018 | Alexander et al. |
| 9,955,858 B2 | 5/2018 | Pamnani et al. |
| 9,968,262 B2 | 5/2018 | Greenstein et al. |
| 9,968,346 B2 | 5/2018 | Alexander et al. |
| 9,980,710 B2 | 5/2018 | Seifert et al. |
| 9,986,901 B2 | 6/2018 | Grey et al. |
| 9,986,903 B2 | 6/2018 | Nadershahi et al. |
| 9,986,988 B2 | 6/2018 | Ferro et al. |
| 9,999,345 B2 | 6/2018 | Vayser et al. |
| 10,004,392 B2 | 6/2018 | Millard et al. |
| 10,004,393 B2 | 6/2018 | Kucklick |
| 10,028,648 B2 | 7/2018 | Goldfain et al. |
| 10,028,649 B2 | 7/2018 | Salvati et al. |
| 10,028,780 B2 | 7/2018 | Wolf et al. |
| 10,045,686 B2 | 8/2018 | Ou Yang et al. |
| 10,045,731 B2 | 8/2018 | Prasad et al. |
| 10,052,432 B2 | 8/2018 | Dexter et al. |
| 10,064,611 B2 | 9/2018 | Ross et al. |
| 10,064,613 B2 | 9/2018 | Davis et al. |
| 10,068,173 B2 | 9/2018 | Vayser et al. |
| 10,092,176 B2 | 10/2018 | Kienzle et al. |
| 10,092,281 B2 | 10/2018 | Perler et al. |
| 10,098,530 B2 | 10/2018 | McMahon et al. |
| 10,105,043 B2 | 10/2018 | George |
| 10,117,646 B2 | 11/2018 | Friedrich et al. |
| 10,130,441 B2 | 11/2018 | Martinez |
| 2001/0029044 A1 | 10/2001 | Gombrich et al. |
| 2002/0016528 A1 * | 2/2002 | Tan ..................... A61B 1/32 600/224 |
| 2002/0022769 A1 | 2/2002 | Smith et al. |
| 2002/0038075 A1 | 3/2002 | Tsai |
| 2002/0038076 A1 | 3/2002 | Sheehan et al. |
| 2002/0055670 A1 | 5/2002 | Weiss |
| 2002/0156350 A1 | 10/2002 | Nieto |
| 2002/0165435 A1 | 11/2002 | Weiss |
| 2002/0198471 A1 | 12/2002 | Baxter-Jones et al. |
| 2003/0105387 A1 * | 6/2003 | Frumovitz ............... A61B 1/32 600/220 |
| 2003/0139673 A1 | 7/2003 | Vivenzio et al. |
| 2003/0158502 A1 | 8/2003 | Baxter-Jones et al. |
| 2003/0176772 A1 | 9/2003 | Yang |
| 2003/0187331 A1 | 10/2003 | Faludi et al. |
| 2004/0026829 A1 | 2/2004 | Van Der Weegen |
| 2004/0054260 A1 | 3/2004 | Klaassen et al. |
| 2004/0141175 A1 | 7/2004 | Baldwin et al. |
| 2004/0183482 A1 | 9/2004 | Roberts et al. |
| 2004/0184288 A1 | 9/2004 | Bettis |
| 2004/0186355 A1 | 9/2004 | Strong |
| 2005/0065496 A1 | 3/2005 | Simon et al. |
| 2005/0085699 A1 | 4/2005 | Weiss |
| 2005/0159649 A1 | 7/2005 | Patel |
| 2005/0192482 A1 | 9/2005 | Carpenter |
| 2005/0215858 A1 | 9/2005 | Vail, III |
| 2005/0240081 A1 | 10/2005 | Eliachar |
| 2005/0277811 A1 | 12/2005 | Richards et al. |
| 2006/0084843 A1 | 4/2006 | Sommerich et al. |
| 2006/0122463 A1 * | 6/2006 | Klaassen ............... A61B 1/32 600/221 |
| 2006/0189847 A1 | 8/2006 | Yee et al. |
| 2007/0043264 A1 | 2/2007 | Gillis et al. |
| 2007/0060795 A1 | 3/2007 | Vayser et al. |
| 2007/0060938 A1 | 3/2007 | Dziadik et al. |
| 2007/0100212 A1 | 5/2007 | Pimenta et al. |
| 2007/0208226 A1 | 9/2007 | Grey et al. |
| 2007/0230164 A1 | 10/2007 | Vivenzio et al. |
| 2007/0230167 A1 | 10/2007 | McMahon et al. |
| 2007/0255110 A1 * | 11/2007 | Wax ..................... A61B 1/303 600/223 |
| 2008/0002426 A1 | 1/2008 | Vayser et al. |
| 2008/0221569 A1 | 9/2008 | Moore et al. |
| 2008/0228038 A1 * | 9/2008 | McMahon ........ A61B 1/00105 600/223 |
| 2008/0269564 A1 | 10/2008 | Gelnett |
| 2008/0269565 A1 | 10/2008 | McMahon et al. |
| 2009/0018400 A1 | 1/2009 | Raymond et al. |
| 2009/0069634 A1 | 3/2009 | Larkin |
| 2009/0097236 A1 | 4/2009 | Miller et al. |
| 2009/0112068 A1 | 4/2009 | Grey et al. |
| 2009/0275603 A1 | 11/2009 | Krauter et al. |
| 2009/0275803 A1 * | 11/2009 | Krauter ................ A61B 1/303 600/222 |
| 2009/0287192 A1 | 11/2009 | Vivenzio et al. |
| 2009/0312610 A1 | 12/2009 | Buchok et al. |
| 2010/0036382 A1 | 2/2010 | Bonnadier |
| 2010/0041955 A1 | 2/2010 | Grey et al. |
| 2010/0191062 A1 | 7/2010 | Kieffer |
| 2010/0292533 A1 | 11/2010 | Kasahara et al. |
| 2011/0022032 A1 * | 1/2011 | Zemlok ............ A61B 17/07207 606/1 |
| 2012/0055470 A1 | 3/2012 | Pecherer et al. |
| 2012/0059226 A1 | 3/2012 | Funt |
| 2012/0078060 A1 | 3/2012 | Swift |
| 2012/0116170 A1 | 5/2012 | Vayser et al. |
| 2013/0041229 A2 | 2/2013 | Hahn et al. |
| 2013/0197313 A1 | 8/2013 | Wan |
| 2013/0245657 A1 | 9/2013 | Deville et al. |
| 2013/0267786 A1 | 10/2013 | Vayser et al. |
| 2013/0281784 A1 | 10/2013 | Ray |
| 2013/0324801 A1 | 12/2013 | Grey et al. |
| 2014/0275790 A1 | 9/2014 | Vivenzio et al. |
| 2014/0309499 A1 | 10/2014 | Swift |
| 2014/0316211 A1 | 10/2014 | Hermle |
| 2014/0323800 A1 | 10/2014 | Dye |
| 2014/0364695 A1 | 12/2014 | Nadershahi et al. |
| 2014/0371536 A1 | 12/2014 | Miller et al. |
| 2015/0018625 A1 | 1/2015 | Miraki et al. |
| 2015/0157469 A1 | 6/2015 | Prado et al. |
| 2015/0238070 A1 | 8/2015 | Lia et al. |
| 2016/0000305 A1 | 1/2016 | Elbaz et al. |
| 2016/0038012 A1 * | 2/2016 | McMahon ............... A61B 1/06 600/210 |
| 2016/0038032 A1 | 2/2016 | Dan |

(56) References Cited

U.S. PATENT DOCUMENTS

| | | |
|---|---|---|
| 2016/0095506 A1 | 4/2016 | Dan et al. |
| 2016/0100751 A1 | 4/2016 | Davis et al. |
| 2016/0302657 A1 | 10/2016 | Hussey et al. |
| 2017/0007228 A1 | 1/2017 | Costabile |
| 2017/0020621 A1 | 1/2017 | Huldin et al. |
| 2017/0065282 A1 | 3/2017 | Mathis et al. |
| 2017/0079518 A1 | 3/2017 | Elbaz et al. |
| 2017/0172404 A1 | 6/2017 | McMahon et al. |
| 2017/0181605 A1 | 6/2017 | Lalli et al. |
| 2017/0181607 A1 | 6/2017 | Lalli et al. |
| 2017/0181615 A1 | 6/2017 | Vella et al. |
| 2017/0181616 A1 | 6/2017 | Vella et al. |
| 2017/0224206 A1 | 8/2017 | Vayser |
| 2017/0300623 A1 | 10/2017 | Rosenblatt et al. |
| 2017/0303903 A1 | 10/2017 | De Koning et al. |
| 2017/0347871 A1 | 12/2017 | Wallace et al. |
| 2017/0360423 A1 | 12/2017 | Stevenson et al. |
| 2018/0000469 A1 | 1/2018 | Wood et al. |
| 2018/0008137 A1 | 1/2018 | Poormand |
| 2018/0008138 A1 | 1/2018 | Thommen et al. |
| 2018/0008368 A1 | 1/2018 | Duggal et al. |
| 2018/0014721 A1 | 1/2018 | Rullo et al. |
| 2018/0014842 A1 | 1/2018 | Shener-Irmakoglu |
| 2018/0014900 A1 | 1/2018 | Vayser et al. |
| 2018/0036095 A1 | 2/2018 | Vayser et al. |
| 2018/0042596 A1 | 2/2018 | Tsubouchi |
| 2018/0064316 A1 | 3/2018 | Charles et al. |
| 2018/0064317 A1 | 3/2018 | Tesar |
| 2018/0078301 A1 | 3/2018 | Vayser |
| 2018/0116581 A1 | 5/2018 | Prasad et al. |
| 2018/0125336 A1 | 5/2018 | Goldfarb et al. |
| 2018/0125347 A1 | 5/2018 | Czyzewski et al. |
| 2018/0132710 A1 | 5/2018 | Pacey et al. |
| 2018/0132970 A1 | 5/2018 | Ritter |
| 2018/0153391 A1 | 6/2018 | McMahon et al. |
| 2018/0156448 A1 | 6/2018 | Phillips, Jr. et al. |
| 2018/0206832 A1 | 7/2018 | Greeley et al. |
| 2018/0228376 A1 | 8/2018 | Greenstein et al. |
| 2018/0228483 A1 | 8/2018 | Duggal et al. |
| 2018/0235444 A1 | 8/2018 | Tsai |
| 2018/0235592 A1 | 8/2018 | Kass et al. |
| 2018/0249902 A1 | 9/2018 | Grey et al. |
| 2018/0263480 A1 | 9/2018 | Lalli et al. |
| 2018/0271581 A1 | 9/2018 | Ou Yang et al. |
| 2018/0280011 A1 | 10/2018 | Ferro et al. |
| 2018/0296082 A1 | 10/2018 | Salvati et al. |
| 2018/0317746 A1 | 11/2018 | Lalli et al. |
| 2018/0317752 A1 | 11/2018 | Cybulski et al. |
| 2018/0317902 A1 | 11/2018 | Green et al. |
| 2018/0328572 A1 | 11/2018 | Kennedy et al. |
| 2018/0336474 A1 | 11/2018 | Vayser et al. |
| 2018/0344144 A1 | 12/2018 | Bouquet |
| 2018/0353059 A1 | 12/2018 | Tesar |
| 2018/0360301 A1 | 12/2018 | Kucklick |

FOREIGN PATENT DOCUMENTS

| | | |
|---|---|---|
| CN | 2516109 Y | 10/2002 |
| CN | 2629738 Y | 8/2004 |
| CN | 1565664 A | 1/2005 |
| CN | 2668152 Y | 1/2005 |
| CN | 1717195 A | 1/2006 |
| CN | 101179982 A | 5/2008 |
| CN | 201055387 Y | 5/2008 |
| CN | 203591245 U | 5/2008 |
| CN | 102415869 A | 4/2012 |
| CN | 302536685 S | 8/2013 |
| CN | 103925266 A | 7/2014 |
| CN | 203898367 U | 10/2014 |
| CN | 102573700 B | 12/2014 |
| DE | 2128855 A | 12/1972 |
| DE | 202004002963 U1 | 5/2004 |
| DE | 202005019780 U1 | 5/2006 |
| DE | 600 33 612 T2 | 12/2007 |
| EP | 0190014 A2 | 8/1986 |
| FR | 2490478 A1 | 3/1982 |
| RU | 2187972 C2 | 8/2002 |
| RU | 2308873 C2 | 10/2007 |
| WO | 9825512 A1 | 6/1998 |
| WO | 03082123 A2 | 10/2003 |
| WO | 2004064624 A1 | 8/2004 |
| WO | 2006107877 A2 | 10/2006 |
| WO | 2006107878 A2 | 10/2006 |
| WO | 2009137017 A2 | 11/2009 |
| WO | 2013-044151 A1 | 3/2013 |
| WO | 2014-041172 A1 | 3/2014 |
| WO | 2006121530 A2 | 11/2016 |

OTHER PUBLICATIONS http://www.makeitfrom.com/material-properties/Polyetheretheketone-PEEK, printed on Oct. 9, 2016, pp. 1-9.

International Search Report for International application No. PCT/US2016/016154 dated May 19, 2016 for corresponding U.S. Appl. No. 14/614,413.

International Search Report, for International application No. PCT/US2016/035508 dated Sep. 15, 2016 for corresponding U.S. Appl. No. 15/171,581.

International Search Report for International application No. PCT/US2016/036833 dated Jan. 19, 2017.

U.S. Patent references 121-125 and U.S. Published Patent Application references 48 and 50 were cited in an Office Action issued in U.S. Appl. No. 15/171,581.

U.S. Published Patent Application references 47, 49 and 51 were cited in a PCT Search Report issued in PCT Application No. PCT/US2017/042617.

The above foreign patent documents 18, 21, 22, 23 and 24 were cited in a Nov. 1, 2017 Chinese Office Action, which is enclosed without an English Translation, that issued in Chinese Patent Application No. 201510543086.7.

The above foreign patent documents 21, 22 and 26 was cited in the Jul. 16, 2018 Chinese Office Action, which is enclosed without an English Translation, that issued in Chinese Patent Application No. 201510543086.7.

International Search Report of PCT/US2018/054925, dated Oct. 9, 2018.

Pankaj Saxena, et al., Hydrodissection Technique of Harvesting Left Internal Thoracic Artery, Department of Cardiac Surgery. The Prince Charles Hospital, Chermside, Brisbane, Queensland, Australia, Thoracic Artery, Ann Thorac Surg., 2005; 80:335-6.

The above documents were cited in a European Search Report dated Nov. 23, 2018, which is enclosed, that issued in the corresponding European Patent Application No. 16747107.7.

The above patent was cited in a Oct. 29, 2018 Chinese Office Action, which is enclosed without an English Translation, that issued in Chinese Patent Application No. 201711159829.6.

The above Foreign Patent documents were cited in a European Search Report dated Nov. 23, 2018, which is enclosed, that issued in European Patent Application No. 16747107.7.

* cited by examiner

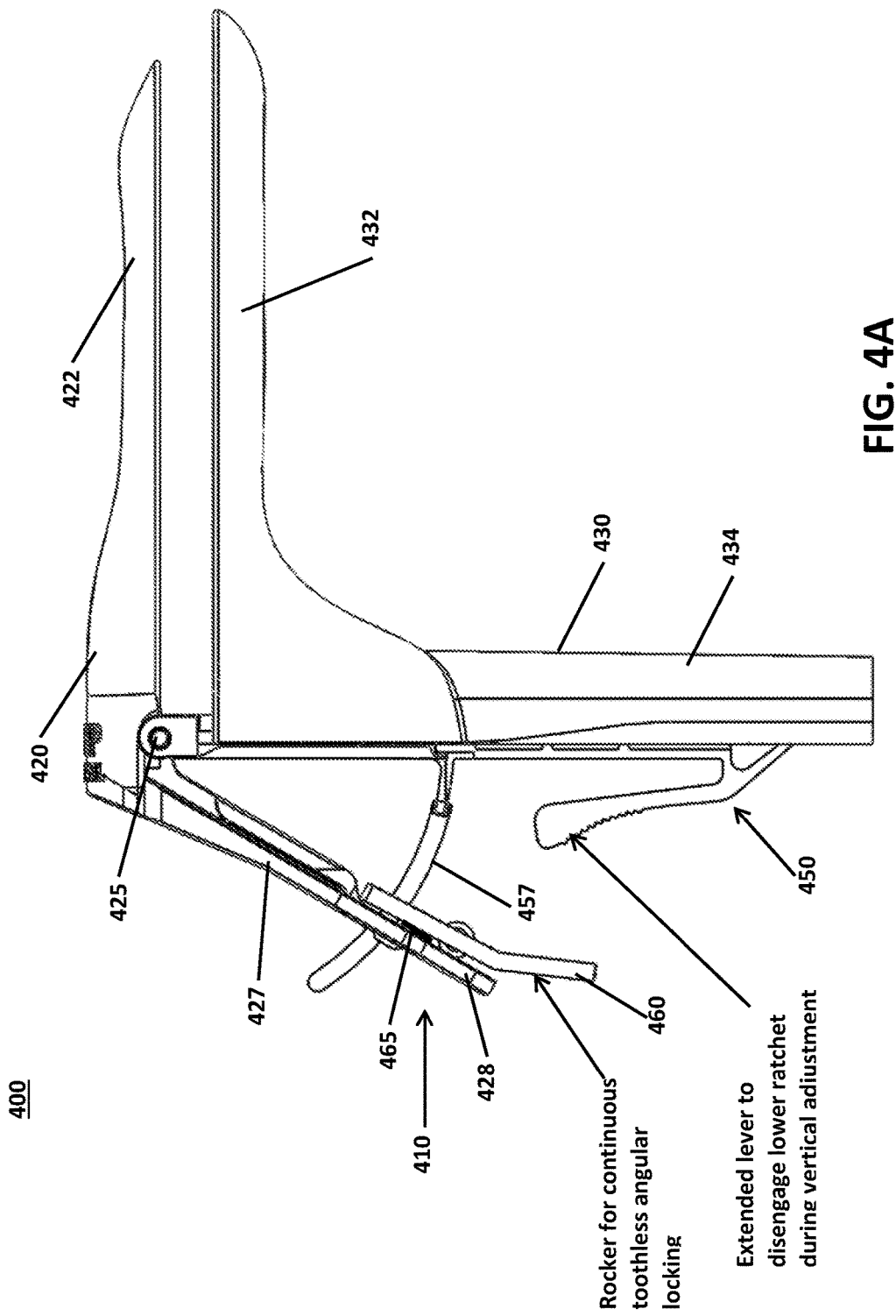

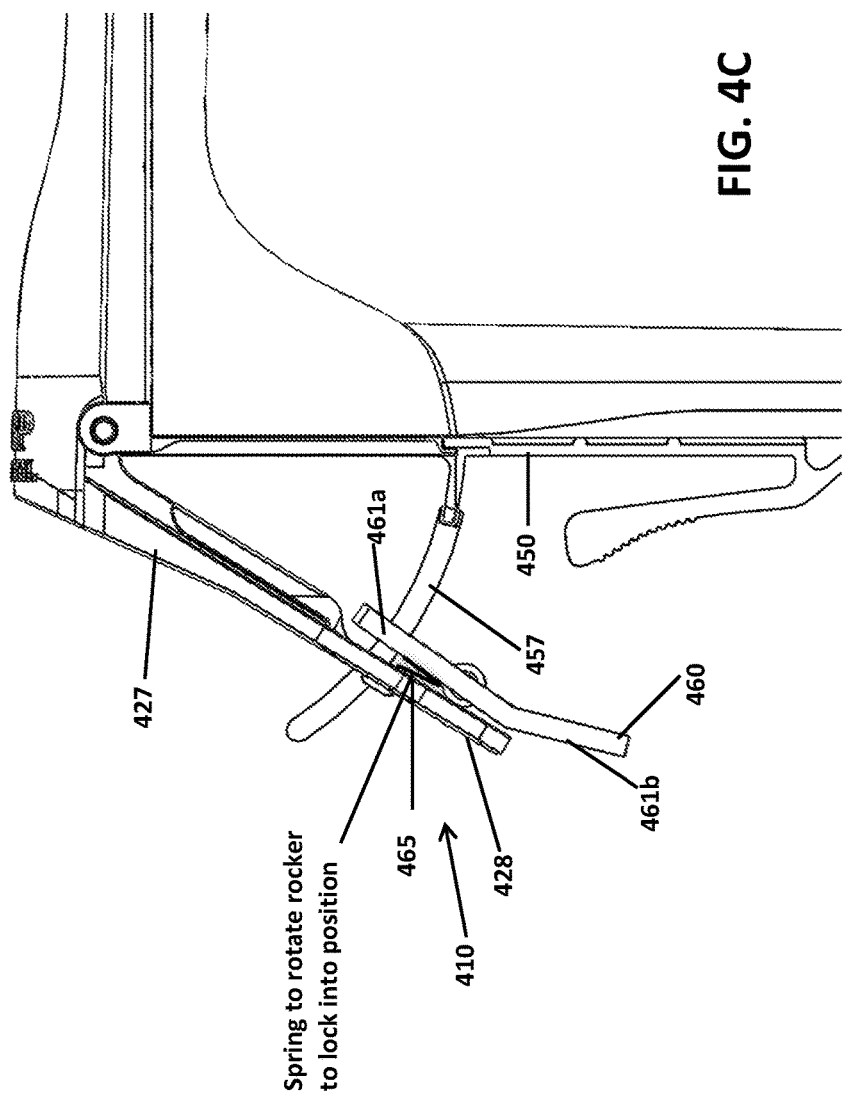

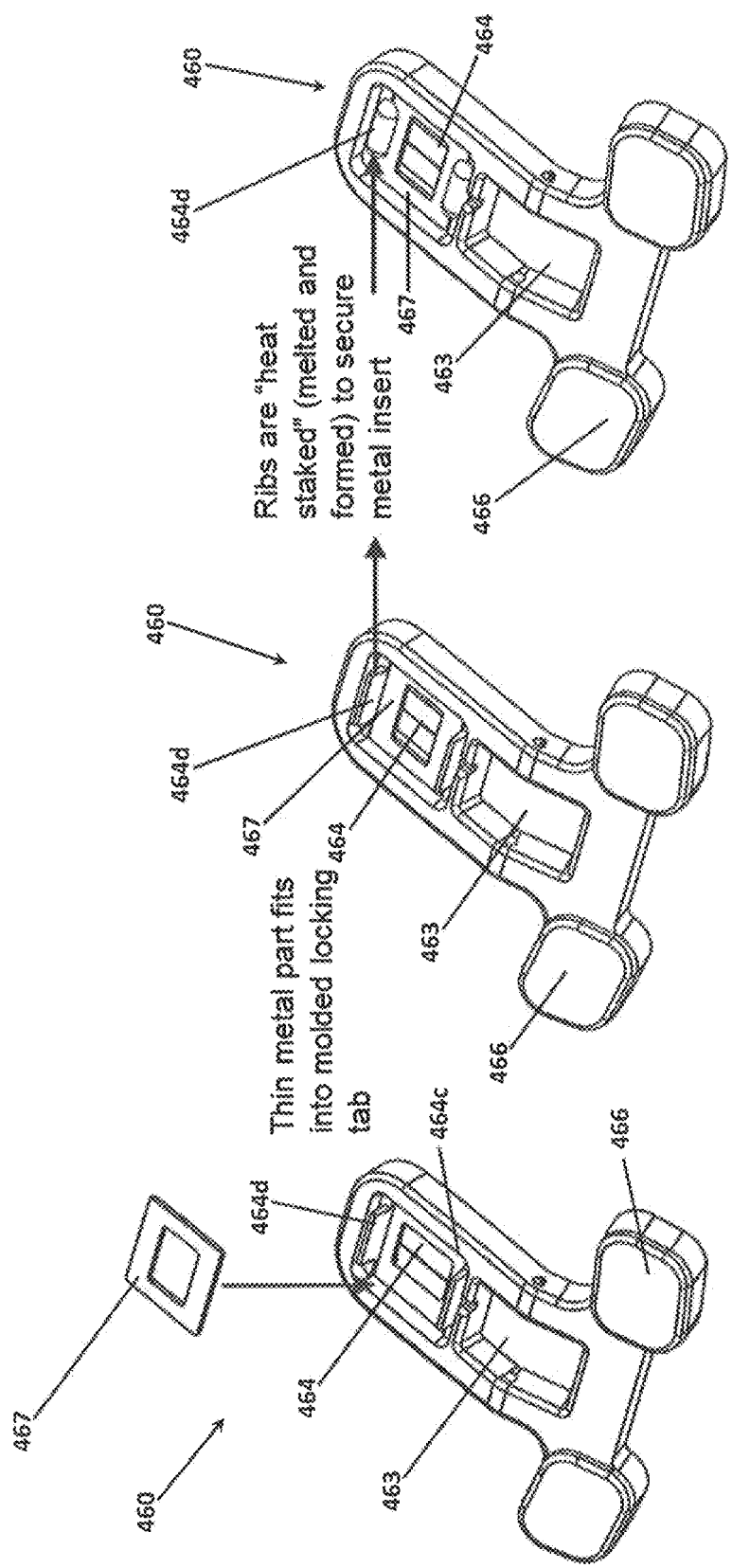

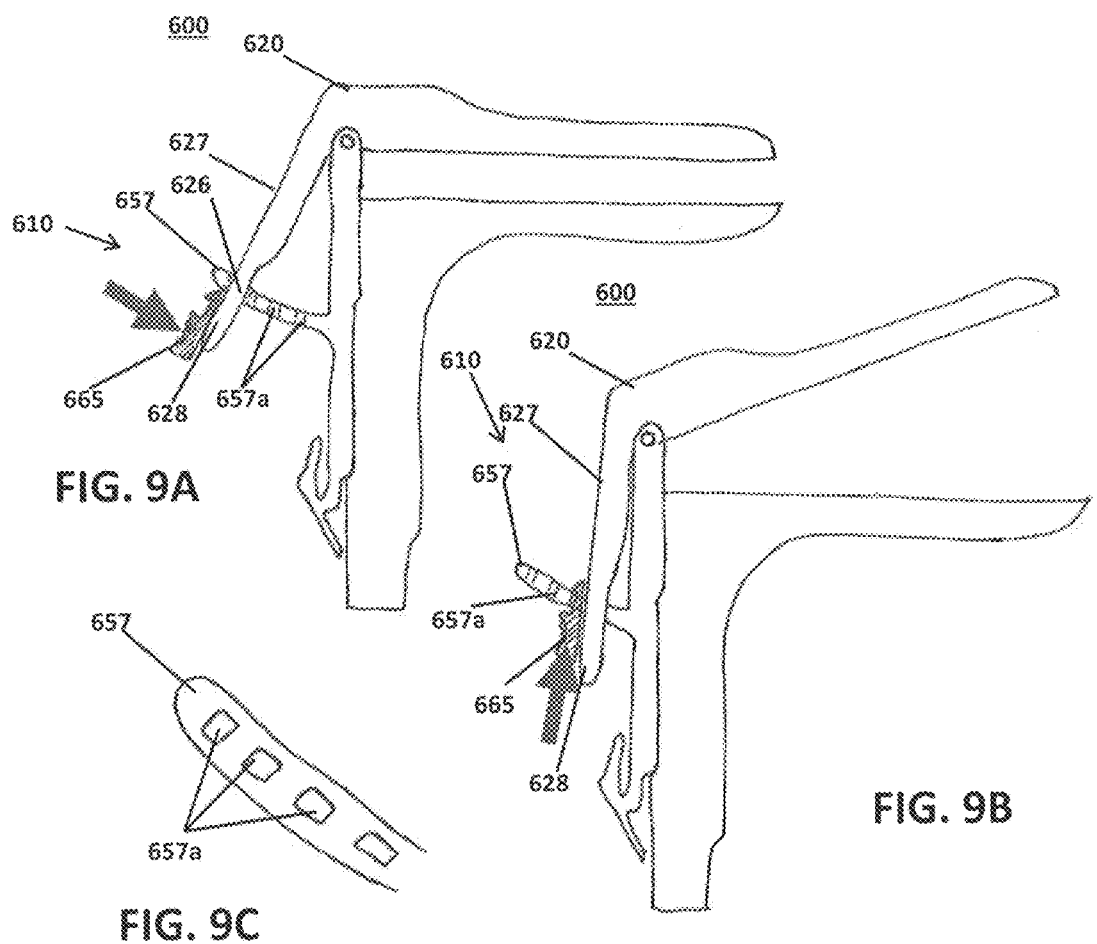

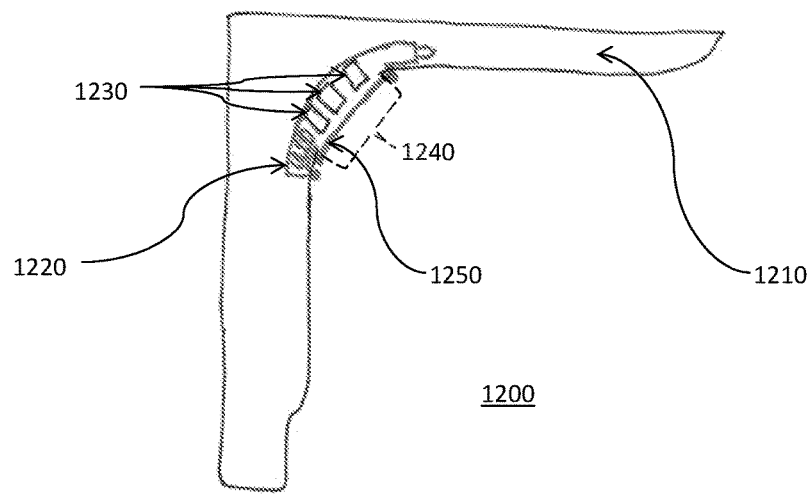
FIG. 16A
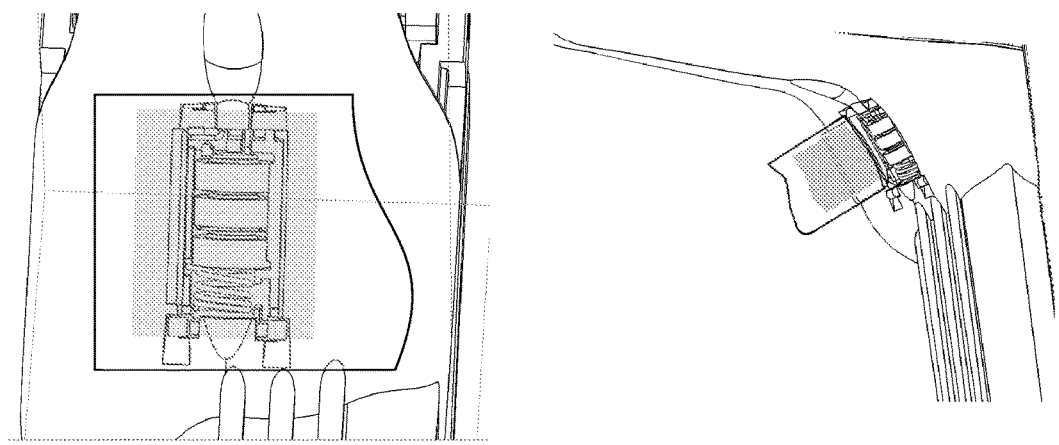
FIG. 16B
FIG. 16C

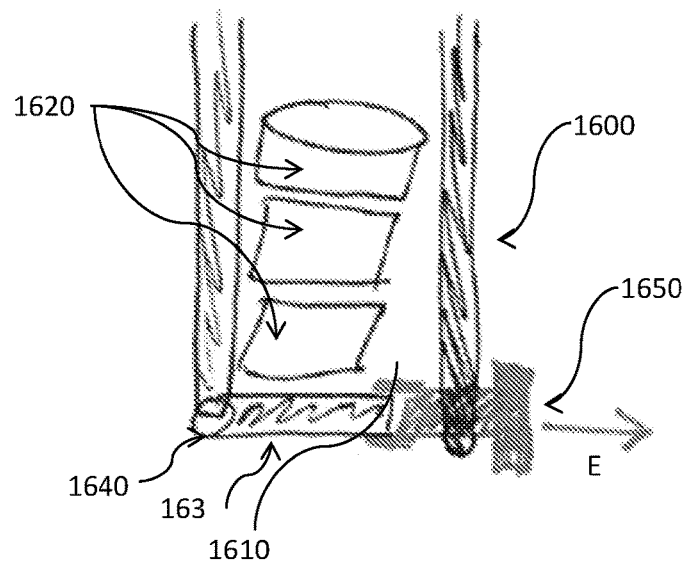
FIG. 20A
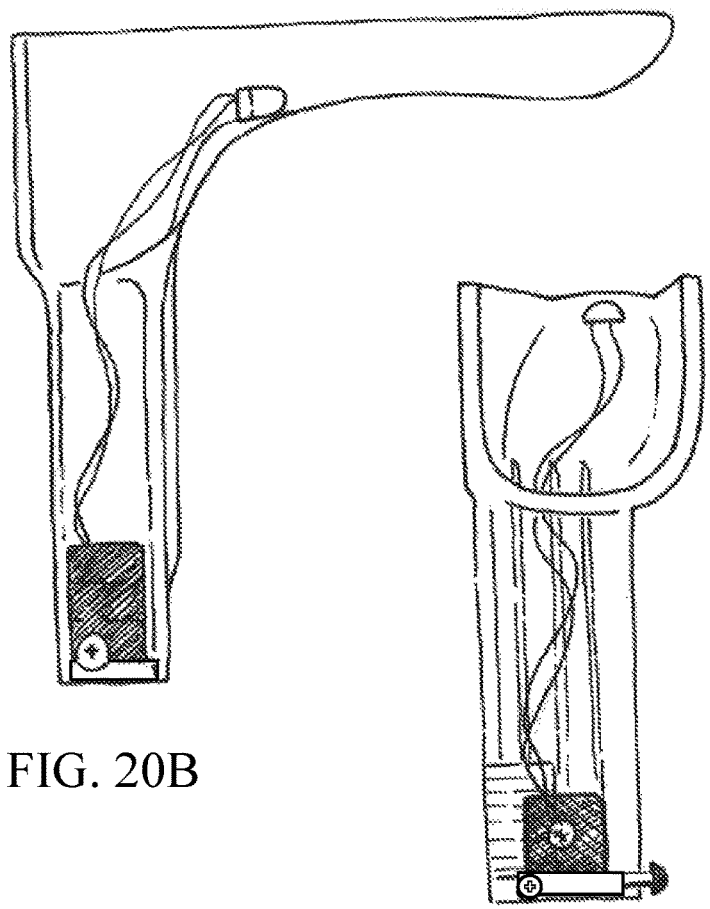
FIG. 20B
FIG. 20C

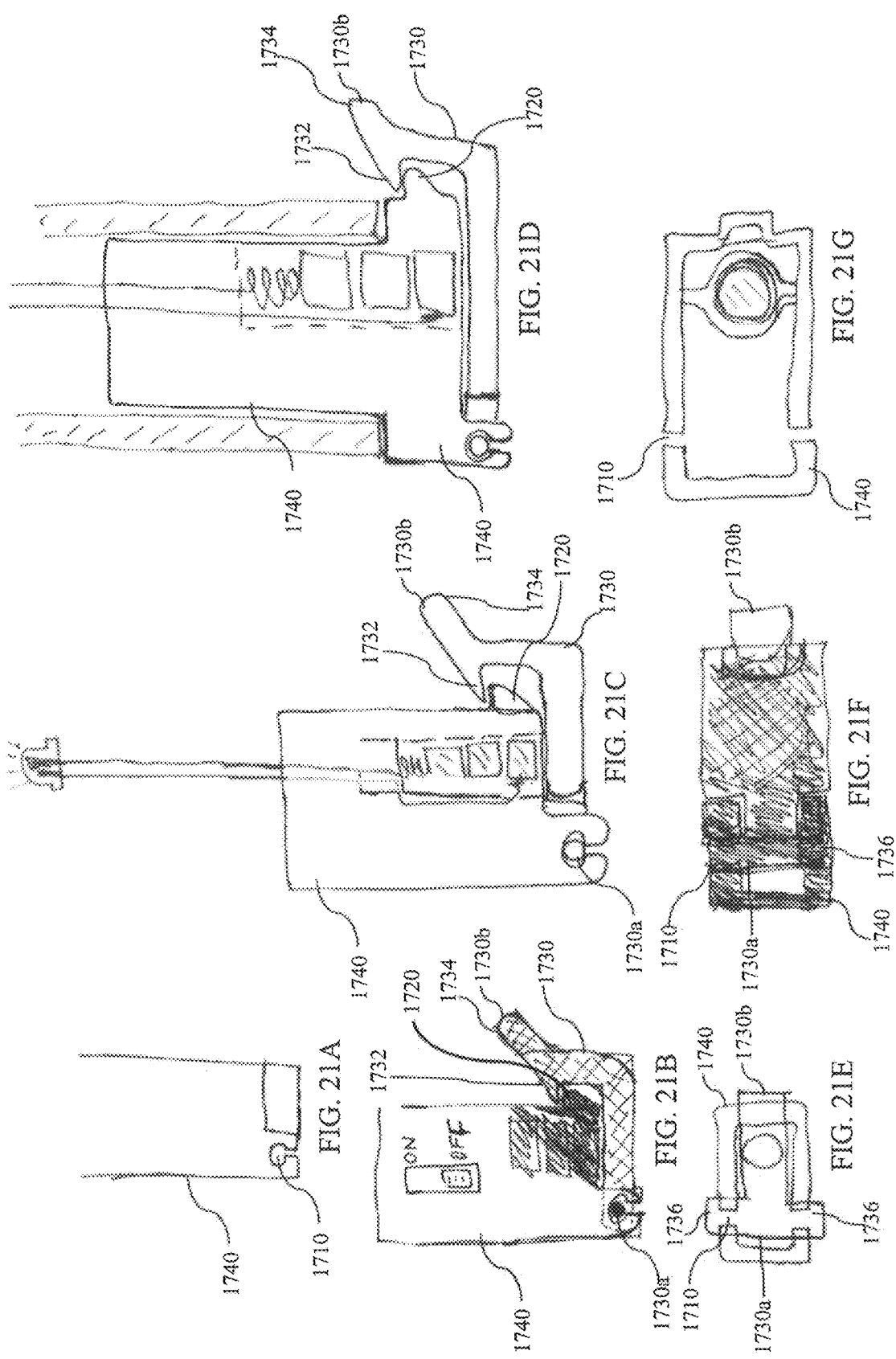

Top assembly is snapped into yoke.

Top assembly snaps into bottom assembly.

SPECULUM

INTRODUCTION

The present invention relates to speculums typically used for examination of a patient. A speculum is a medical instrument for dilating the opening of a body cavity for medical examination. A bivalved vaginal speculum commonly used during a gynecological examination or a surgical procedure includes a pair of hinged blades and is introduced into a patient's vagina in a closed state and then opened to separate the vaginal walls, thus allowing the internal genital organs to be examined. Metal, autoclavable duck-bill specula are conventionally used for gynecological examination and treatment. These units, with exposed joints, sharp edges, and cold metal are universally disliked by patients. The conventional metallic specula blades are typically opaque and thus, the open end between the blades is the only area available for inspection when the metallic speculum is in use. Moreover sterilization of reusable specula can be costly and time-consuming.

Plastic specula, made from lightweight, inexpensive and transparent or translucent material have been developed in order to eliminate the above problems. In addition, plastic specula are typically one-time use disposable specula. As a result, cross-contamination, which may occur when metallic specula are improperly autoclaved, is avoided. In addition, disposable specula are particularly helpful for busy environments, where time is of the essence, such as emergency rooms or busy doctor's offices.

Plastic specula typically includes a pair of blades, which can be moved relative to one another in a vertical direction (translational adjustment) so as to increase or decrease the elevation of an upper blade relative to a lower blade. In addition, the blades may be adjusted angularly with respect to one another (angular adjustment) so as to increase or decrease the angle between the upper and lower blades, and the distance between distal ends of the upper and lower blades. In conventional specula, ratchet mechanisms with ratchet teeth are used for translational and angular adjustment of the upper and/or lower blades. Examples of such mechanisms are disclosed in applicant's U.S. application Ser. No. 13/241,136 (U.S. Pat. No. 9,307,897), Ser. No. 14/316,787 (US Pub. No. 2014/0309499) and Ser. No. 14/748,435 (US Pub. No. 2015/0289757), all of which are incorporated herein by reference.

When the ratchet mechanism is used for adjustment of the blades, particularly for the angular adjustment, clicking sounds are audible to the doctor and to the patient. These clicking sounds often cause anxiety to patients being examined. Moreover, since the ratchet mechanism adjusts the blades in distinct steps, doctors may be reluctant to use disposable specula that include such mechanisms or may be reluctant to fully separate the vaginal walls in order to avoid patient discomfort.

U.S. Pat. No. 8,376,942 describes several modifications to the ratchet mechanism that allows a doctor to disengage the mechanism from a lock tooth during adjustment so that clicking sound are generated during adjustment. In addition, the '942 patent describes a mechanism for continuous adjustment of the blades, such as by using side tongues to squeeze and secure in place a curved adjustment arm. However, these mechanisms require additional operations by doctors in order to disengage the mechanism from the lock tooth and/or different operations by doctors in order to adjust the blades from those to which doctors are accustomed. Therefore, proper use of such specula requires additional training for doctors and may be a deterrent in using such specula mechanisms. Furthermore, some of the mechanisms described in the '942 patent add complexity to the speculum device, increasing the cost of manufacturing and assembly.

Conventional specula may also use illumination means for illuminating the subject area for examination. For example, U.S. patent application Ser. Nos. 13/241,136 and 14/316,787 describe specula that include an illumination assembly for illuminating the subject area. These applications are incorporated herein by reference. Illumination assemblies or means typically use a light, such as an LED, and one or more power sources, such as batteries. For example, button batteries are used in the illumination assemblies described in the '136 and '787 applications.

After a disposable speculum is used on a patient, the speculum is disposed as biohazardous waste in accordance with medical waste disposal requirements. Biomedical waste is often incinerated by an appropriate entity. However, batteries usually contain metals, such as mercury, cadmium, zinc, nickel, chromium, lead and others. As a result, when batteries are incinerated along with the biomedical waste, heavy metals may contaminate the ash released by the incinerator, thus polluting the air. Moreover, metals in the batteries can leach out of landfills and pollute water sources. Therefore, proper disposal and recycling of batteries from used specula, without contaminating the batteries with biohazardous materials, is desired.

SUMMARY OF THE INVENTION

It is an objective of the present invention to provide a speculum which has a silent, i.e. click-free, vertical and angular adjustment mechanisms. It is also an objective of the present invention to provide a speculum in which the angular adjustment mechanism allows for flexible adjustment, not constrained by predetermined positions as in the ratchet-type adjustments. It is a further objective to provide a speculum in which the angular and vertical adjustments are ergonomically designed for easy and convenient adjustment by the user and do not require additional training or learning for the user. Furthermore, the speculum of the present invention has a battery removal mechanism which allows for easy removal of batteries without risking contamination of the batteries with biohazardous materials.

In accordance with the present invention, the speculum comprises a lower member including a handle and a lower blade extending at an angle from the handle, an upper blade movably engaged with the lower member by an angular adjustment mechanism so as to allow continuous adjustment of an angle between the upper and lower blades. In the present invention, the angular adjustment mechanism comprises a guiding arm, a rotational lever connected to the upper blade and operable by a user to change the angle between the upper and lower blades, the rotational lever being movably engaged with the guiding arm and configured to move relative to the guiding arm to continuously change the angle between the upper and lower blades, and a locking member movable between a locked position to lock a positional relationship between the rotational lever and the guiding arm and an unlocked position to release a locked positional relationship between the rotational lever and the guiding arm, wherein the locking member is configured to: (1) automatically lock the positional relationship between the rotational lever and the guiding arm along any position on the guiding arm, (2) automatically release the locked positional relationship during operation of the rotational lever in a first direction, and (3) be manually moved to the unlocked position to permit operation of the rotational lever in a second direction opposite to the first direction.

In certain embodiments, the rotational lever is configured to move relative to the guiding arm between a first position corresponding to a closed state of the upper and lower blades and a second position corresponding to a maximum angle between the upper and lower blades. The rotational lever is configured to be locked relative to the guiding arm at any position within a range from the first position to the second position. In certain embodiments, the guiding arm does not include any ratchet teeth.

In some embodiments, the operation of the rotational lever in the first direction causes the angle between the upper and lower blades to increase and wherein the operation of the rotational lever in the first and second directions is substantially silent.

In certain illustrative embodiments, the locking member comprises a rocker pivotably engaged with the rotational lever and configured to pivot between the locked position and the unlocked position. The locking member may also include a biasing member for biasing the rocker to the locked position. In some configurations of the locking member, the rocker includes an opening formed therein, with the size of the opening being greater than a thickness of the guiding arm, and the guiding arm is inserted into the opening formed in the rocker so that when the rocker is in the unlocked position, the guiding arm is allowed to slide through the opening in the rocker, and when the rocker is in the locked position, the guiding arm engages with sidewalls of the opening in the rocker to prevent the guiding arm from sliding through the opening in the rocker. In some embodiments, the rocker is biased to the locked position and is configured to be manually operated to pivot to the unlocked position.

In certain embodiments, the engagement between the rotational lever and the guiding arm is maintained when the locking member is in the locked position and when the locking member is in the unlocked position. In the illustrative embodiments described below, the guiding arm extends from the lower member and the rotational lever extends from a proximal end of the upper blade. The speculum may further comprise a linear support member slidably engaged with the lower member and hingedly engaged with the proximal end of the upper blade, and the linear support member is configured to allow linear adjustment of a vertical distance between the upper blade and the lower blade, and the guiding arm extends from the linear support member. In certain embodiments, the handle includes a plurality of teeth formed thereon, and the linear support member includes a locking projection configured to engage with each tooth, the plurality of teeth defining corresponding fixed open states and a closed state for linear adjustment of the vertical distance between the upper blade and the lower blade. The plurality of teeth are formed on an inner surface of the handle and a portion of the linear support member is disposed inside the handle so that the locking projection engages with said plurality of teeth.

In certain embodiments, the speculum also includes an illumination assembly including at least one light source disposed adjacent to the lower blade, at least one battery provided in the handle, and a battery ejection mechanism for removal of the at least one battery from the handle. The battery ejection mechanism may include a housing for holding the at least one battery in a retained state and an operating member configured to be operated by a user to cause the housing to move from the retained state to an ejected state, and wherein the at least one battery is released from the housing in the ejected state for removal from the handle. The housing has an open side and in the retained state, the at least one battery is retained within the housing by abutting an inner surface of the handle. The handle may include a projection formed on the inner surface thereof, the projection abutting the at least one battery in the retained state. In some embodiments, the handle includes a main body having an open rear side and a rear faceplate configured to engage with the main body and to cover the open rear side of the main body, the battery ejection mechanism is engaged with the rear faceplate of the handle, and the rear faceplate further includes an illumination assembly cover for enclosing electrical connections between the at least one battery and the at least one light source and for partially enclosing the at least one light source.

In some embodiments of the speculum, the angle between the handle and the lower member is between 95 and 120 degrees.

The present invention also includes a speculum comprising a lower member including a handle and a lower blade extending at an angle from the handle; an upper blade movably engaged with the lower member by an angular adjustment mechanism for adjustment of an angle between the upper and lower blades; and the angular adjustment mechanism configured to allow continuous adjustment of the angle between the upper and lower blades to any angle within a predetermined range from a closed state to a maximum angle between the upper and lower blades, wherein the angular adjustment mechanism includes a locking member movable between a locked position to lock a positional relationship between the upper and lower blades and an unlocked position to release a locked positional relationship between the upper and lower blades, wherein the locking member is configured to: (1) automatically lock the positional relationship between the upper and lower blades at any selected angle within the predetermined range, (2) automatically release the locked positional relationship between the upper and lower blades when the angular adjustment mechanism is operated to increase the angle between the upper and lower blades, and (3) be manually moved to the unlocked position to permit operation of the angular adjustment mechanism to decrease the angle between the upper and lower blades.

The present invention further includes a speculum comprising a lower member including a handle having a proximal end and a distal end and a lower blade extending at an angle from the proximal end of the handle, an upper blade movably engaged with the lower member by an angular adjustment mechanism so as to allow adjustment of an angle between the upper and lower blades, and an illumination assembly including at least one light source, at least one battery provided in the handle and a battery ejection mechanism for removal of the at least one battery from the handle via an opening formed in the handle, wherein the battery ejection mechanism includes an operating member configured to be operated by a user to cause the at least one battery to be released from the handle.

BRIEF DESCRIPTION OF THE DRAWINGS

The above and other features and aspects of the present invention will become more apparent upon reading the following detailed description in conjunction with the accompanying drawings, in which:

FIGS. 4A-4G show a speculum with a first embodiment of an angular adjustment mechanism of the present invention and details of the angular adjustment mechanism;

FIGS. 6A-6C show another embodiment of a rocker for use in the angular adjustment mechanism of the present invention;

FIGS. 9A-9D show a speculum with a third embodiment of an angular adjustment mechanism;

FIGS. 16A-16C show a medical device with a first embodiment of an illumination assembly of the present invention that allows for battery removal;

FIGS. 20A-20D show a medical device with a fifth embodiment of an illumination assembly of the present invention that allows for battery removal;

FIGS. 21A-21G show a portion of a medical device with a sixth embodiment of an illumination assembly of the present invention that allows for battery removal;

DETAILED DESCRIPTION

The present invention includes a speculum that is more ergonomic and comfortable for use by doctors. The speculum of the present invention has a silent mechanism for angular and/or translational adjustment of the blades. In addition, mechanisms for continuous adjustment, particularly angular continuous adjustment, of the blades are described. Such continuous adjustment mechanisms have reliable locking capabilities and have simple construction that does not require additional training. Moreover, in the present invention, the mechanism for translational adjustment is modified in order to enable easier operation to adjust one blade vertically relative to another.

The present invention also provides a speculum which includes an illumination assembly or the like with batteries and in which the batteries can be easily removed by the doctor and recycled after the speculum is used on a patient. In particular, the speculum of the present invention enables a doctor to remove the batteries, while wearing gloves, without having the batteries come into contact with the doctor's gloves or other parts of the speculum.

Figure 1:
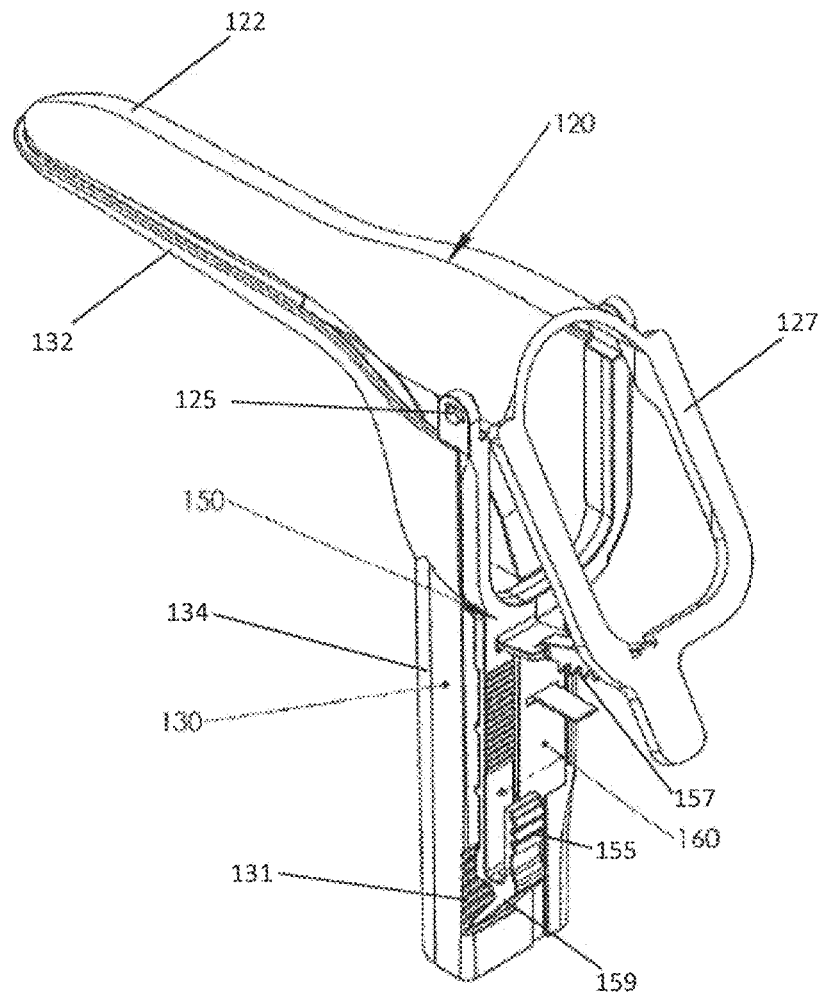
FIG. 1 shows a conventional disposable vaginal speculum.

FIG. 1 shows a conventional disposable vaginal speculum 100 which includes an upper member 120 with an upper blade 122, a lower member 130 with a lower blade 132 and a handle 134, and a linear support member 150 which is engaged with the upper member 120 and the lower member 130. As shown in FIG. 1, the upper member 120 includes a hinge assembly 125 for pivotably engaging with the linear support member 150 and an operating mechanism 127 that extends from the hinge assembly 125 and which is used for engaging with ratchet teeth in a guiding arm 157 that extends from the linear support member 150 for angular adjustment. The linear support member 150 also includes an elevation leg 155 extending from and a locking tooth 159 its lower or distal end, wherein the elevation leg 155 is operated to disengage and engage the locking tooth 159 from stop tabs 131 on the outer surface of the handle 134 and for lifting or lowering of the linear support member 150 relative to the lower member 130 for translational/vertical adjustment.

In conventional speculums, such as the one shown in FIG. 1, the lower blade 132 extends substantially perpendicularly relative to the handle 134 and the elevation leg 155 is relatively short, having a similar length to that of the locking tooth 159. The elevation leg is also substantially linear and includes a plurality of protrusions for preventing slipping of a user's finger.

Figure 2C:
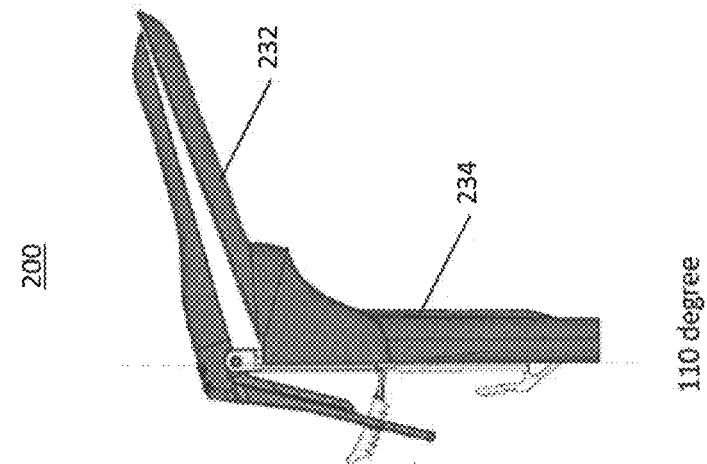
FIGS. 2A-C show examples of an improved speculum with an ergonomic design.
Figure 2B:
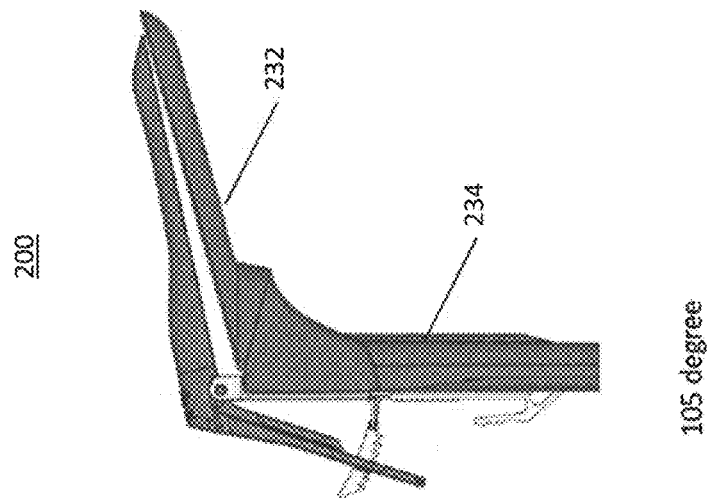
Figure 2A:
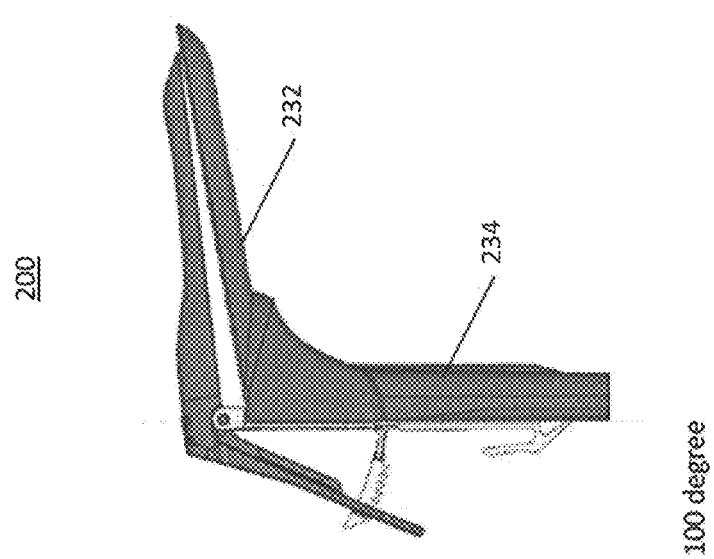

FIGS. 2A-2C show illustrative examples of an improved speculum 200 which has a more ergonomic design. In FIGS. 2A-2C, the lower member is configured so that the angle between the lower blade 232 and the handle 234 is greater than 90 degrees. In FIG. 2A, the angle between the lower blade 232 and the handle 234 is 100 degrees. In FIG. 2B, the angle between the lower blade 232 and the handle 234 is 105 degrees and in FIG. 2C, the angle between the lower blade and the handle is 110 degrees. In other configurations, the angle between the lower blade 232 and the handle 234 may be between 95 degrees and 120 degrees.

Figure 3A:
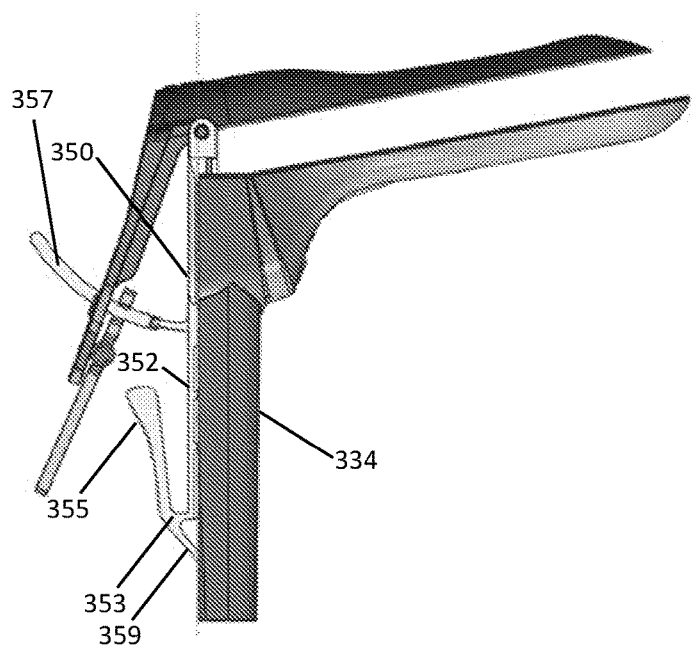
FIGS. 3A-3B show a speculum with an exemplary angular adjustment mechanism of the present invention and a first embodiment of a vertical adjustment mechanism of the present invention.
Figure 3B:
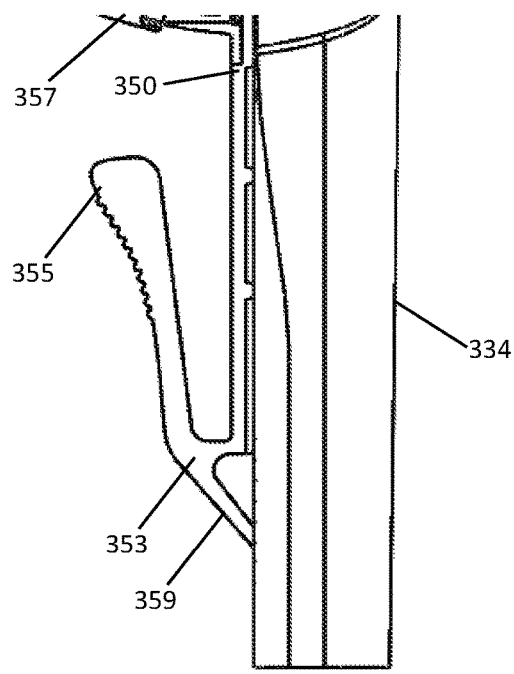

FIGS. 3A and 3B show additional modifications to the speculum 300 in accordance with the present invention. As shown in FIGS. 3A and 3B, the linear support member 350 has an elongated body 352 with a lip 353 extending outwardly from a bottom portion of the elongated body. In FIGS. 3A and 3B, an elevation leg 355 extends vertically in a substantially upward direction from the lip 353, while a locking tooth 359 extends from the lip 353 downwardly at an angle and engages with stop tabs formed on the surface of the handle 334. The total height or length of the elevation leg 355 is optimized for ergonomic contact between a doctor's thumb and the elevation leg 355, and the height or length of the elevation leg 355 is greater than in conventional configurations. In certain illustrative embodiments, the height of the elevation leg 355 is greater than ½ of the height of the elongated body 352 portion extending between the lip 353 and a guiding arm 357. In the illustrative embodiments shown in FIGS. 3A and 3B, the height of the elevation leg 355 is around ⅔ of the elongated body 352 portion extending between the lip 353 and the guiding arm 357. The height of the elevation leg 355 may be varied, depending on the length of the elongated body and the position of the lip 353. In some illustrative embodiments, the distance between the top end of the elevation leg 355 and the guiding arm 357 directly above the elevation leg 355 is about 1-1.5 inches.

Moreover, as shown more closely in FIG. 3B, the elevation leg 355 is ergonomically contoured in order to encourage disengagement of the locking tooth 359 during translational adjustment. Specifically, the thickness of the elevation leg 355 is increased in an upward direction by flaring the shape of the elevation leg 355 outwardly from about midway to the top of the elevation leg 355. This configuration retains the flexibility of the bottom portion of the elevation leg 355 so that the locking tooth 359 can be lifted from engagement. At the same time, the outwardly flaring shape of the top portion of the elevation leg 355 forms an angled surface which enables easy translational adjustment using one finger.

By adjusting the height of the elevation leg, the contact point for translational adjustment is changed, making it easier to perform disengagement of the locking tooth 359 from the stop tabs on the handle and simultaneous vertical adjustment of the linear support member 350 using one finger. As a result, the translational adjustment can be performed silently without sacrificing the user's comfort.

The present invention also includes multiple embodiments of angular adjustment mechanisms for use in speculums. FIGS. 4A-4G show a first embodiment of an angular adjustment mechanism for use in speculums. As shown in FIGS. 4A-4G, the angular adjustment mechanism can be used with the improved translational adjustment mechanism shown in FIGS. 3A and 3B. However, the angular adjustment mechanism of FIGS. 4A-4G may also be used in speculums with conventional translational adjustment mechanisms. In addition, the angular adjustment mechanism of FIGS. 4A-4G may be implemented in speculums shown in FIGS. 2A-2C that have a larger than a 90 degree angle between the lower blade and the handle.

Figure 4B:
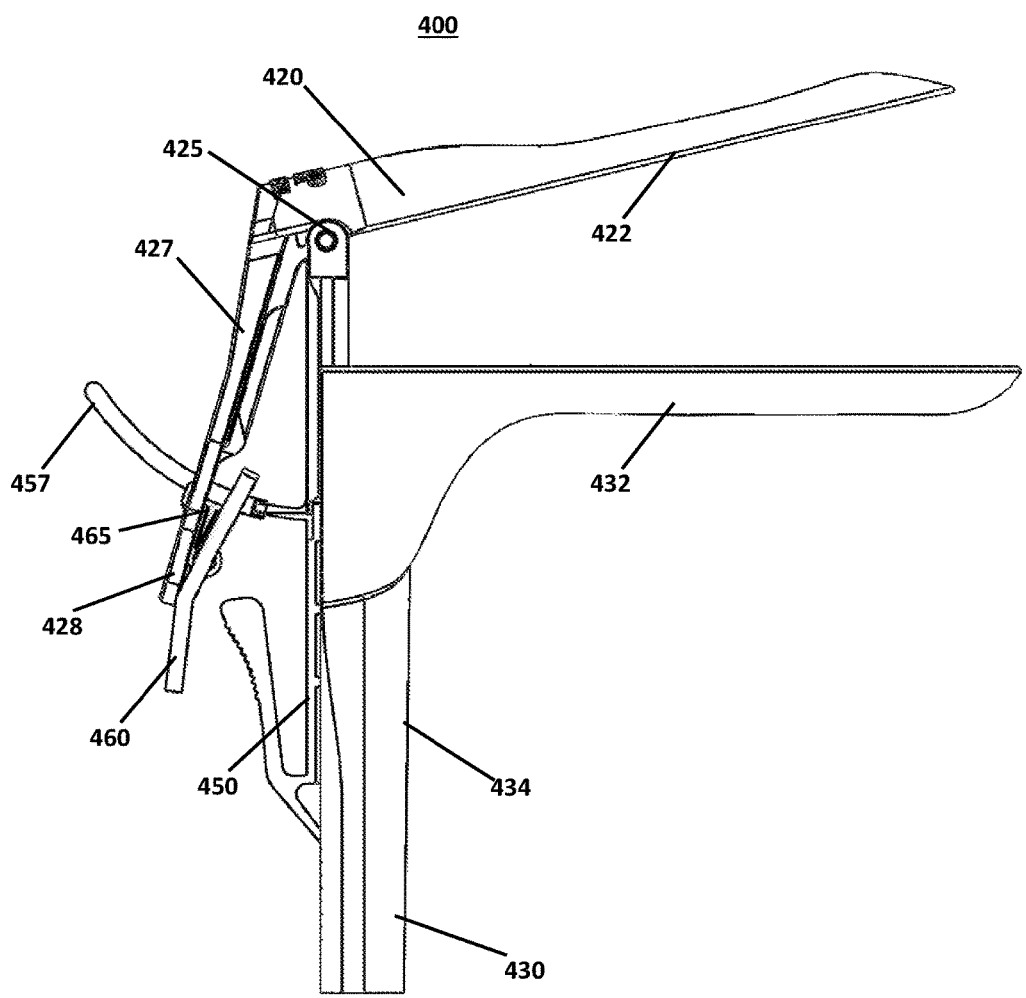

FIGS. 4A and 4B show exemplary speculums 400 that include the angular adjustment mechanism 410 of the present invention. In FIG. 4A the speculum is shown in a closed state while in FIG. 4B, the speculum is shown in an open state using both translational and angular adjustment mechanisms. As shown, the speculum 400 includes an upper member 420, a lower member 430 and a linear support member 450 pivotably engaged with the upper member 420 and slidably engaged with the lower member 430. The upper member 420 includes an upper blade 422, a hinge assembly 425 that pivotably engages with a top portion of the linear support member 450 and an operating mechanism 427 that can be operated by a user for angular adjustment of the upper blade 422 relative to a lower blade 432. The components of the upper member 420 may be integrally formed by injection molding, 3D printing or other known techniques. The lower member 430 includes the lower blade 432 and a handle 434. The components of the lower member 430 may be integrally formed by injection molding, 3D printing or other known techniques. The linear support member 450 includes a translational adjustment mechanism at its lower end, which is described above with respect to FIGS. 3A and 3B, and a guiding arm 457, which may be straight or curved and which engages with the operating mechanism 427 and a rocker 460 for angular adjustment. The guiding arm 457 may be integrally formed with the remaining parts of the linear support member 450.

The angular adjustment mechanism 410 of the speculum includes the guiding arm 457 extending from the linear support member 450, the operating mechanism 427 extending from the upper blade, the rocker 460 and a biasing member 465, such as a spring. In the angular adjustment mechanism 410, the operating mechanism 427 and the rocker 460 are pivotably engaged with one another, and are also slidably engaged with the guiding arm 457. The biasing member 465 biases the operating mechanism 427 and the rocker 460 to pivot away from one another and into a locked state with respect to the guiding arm 457, so that in the locked state, the operating mechanism 427 and the rocker 460 are prevented from sliding relative to the guiding arm 457. This locked state retains the corresponding angular adjustment position of the upper blade relative to the lower blade of the speculum. The rocker is also adapted to be operated by a user so as to release the locked state, preferably by causing compression of the biasing member 465, so that the rocker 460 and the operating mechanism 427 can slide relative to the guiding arm 457 (released state) to allow for angular adjustment of the upper blade relative to the lower blade of the speculum in either direction. Moreover, the angular adjustment mechanism is configured so that the operating mechanism 427 can be operated to increase the angle between the upper and lower blades, without additional operation of the rocker to release the locked state, and upon completion of the adjustment, the rocker and the operating mechanism 427 automatically lock into the locked state.

FIGS. 4C-4G show the details of the exemplary embodiment of the angular adjustment mechanism 410. As shown, the operating mechanism 427 comprises a yoke structure extending out and down from the upper blade and includes an opening or recess 426 for receiving the guiding arm 457. When the operating mechanism 427 is operated by the user, the guiding arm 457 slides through the recess 426, which prevents lateral movement by the guiding arm 457. The recess 426 may be disposed on the right side or the left side of the operating mechanism 427. However, in other embodiments, the recess may be positioned centrally. The operating mechanism 427 includes an angular adjustment tab 428 which extends outwardly from the lower edge of the operating mechanism 427. In the present illustrative embodiment, the angular adjustment tab 428 is disposed on the same side as the recess 426, and may be aligned with the recess 426. When pressure is applied by the user to the angular adjustment tab 428, the operating mechanism 427 and the rocker 460 slide relative to the guiding arm 457, which causes the upper blade 422 to hinge relative to the linear support member 450 so as to increase the angle between the upper blade 422 and the lower blade 432.

As shown in FIGS. 4C-4G, the rocker 460 is a substantially chevron-shaped member including a first leg 461a and a second leg 461b disposed at an angle, and preferably, at an obtuse angle, with respect to one another. In the illustrative embodiment shown, the first leg is longer than the second leg. The first leg 461a of the rocker pivotably engages with the operating mechanism 427 via a pivot mechanism 429, which is described in more detail below. The first leg 461a of the rocker 460 also engages with the guiding arm 457 via a locking recess 464, which receives the guiding arm 457 therein and allows the guiding arm 457 to slide therein during angular adjustment, i.e., in the released state. A second leg 461b of the rocker 460 forms a release tab which is used for releasing the locked state of the rocker 460.

Figure 4D:
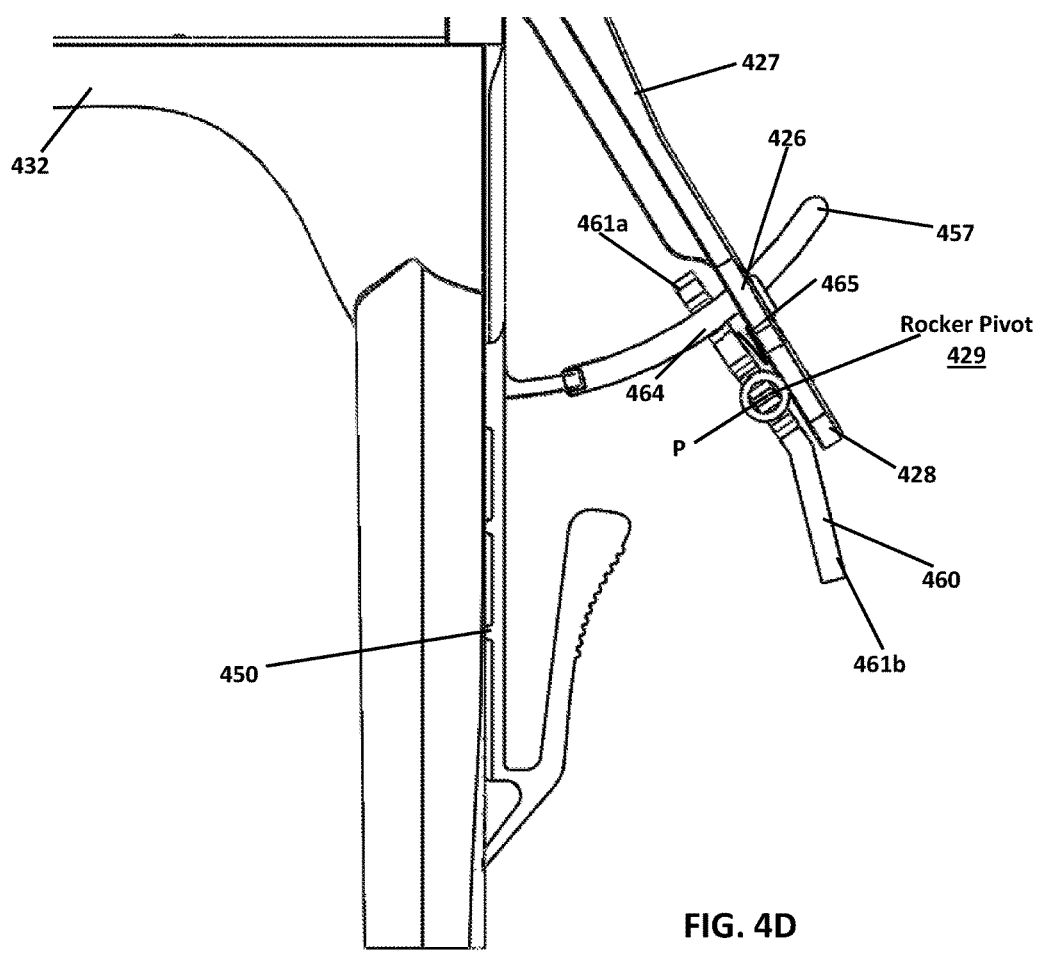
Figure 4E:
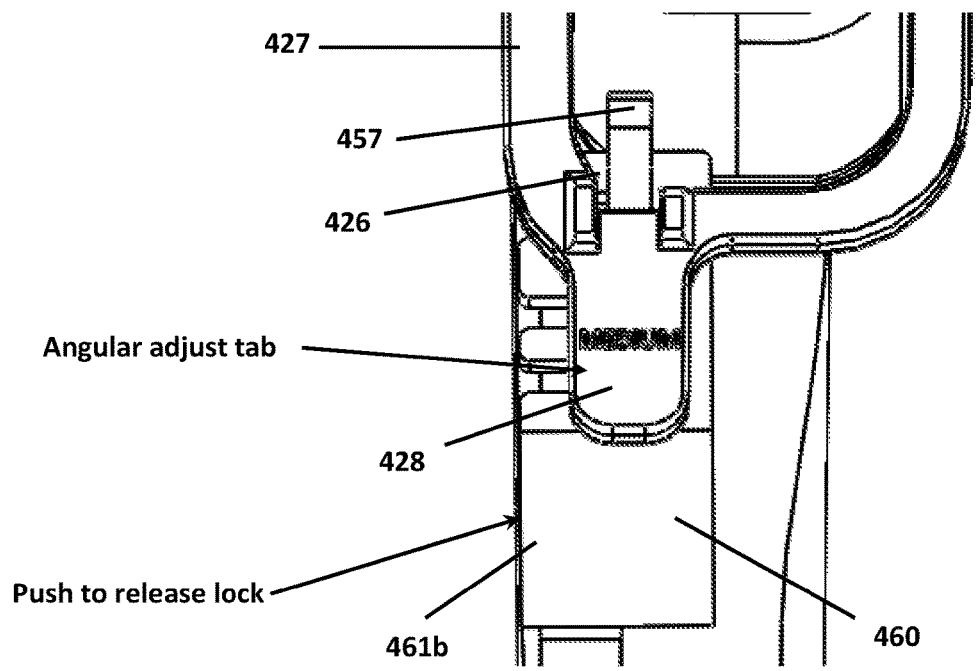

The biasing member 465 is provided in a space formed by the angular adjustment tab 428, the first leg 461a of the rocker 460 and the guiding arm 457. In the illustrative embodiment shown in FIGS. 4A-4G, the biasing member 465 is provided near the pivot mechanism 429 and between the points of engagement of the first leg 461a with the guiding arm 457 and with the operating mechanism 427, i.e., in a triangularly-shaped space formed by the angular adjustment tab 428, the first leg 461a of the rocker and the guiding arm 457. In the illustrative embodiment shown in FIGS. 4A-4G, the biasing member 465 is a V-shaped spring or a leaf spring. However, helical compression springs, torsion springs and other types of springs are suitable for use as the biasing member. The biasing member 465 biases the angular adjustment tab 428 and the first leg 461a of the rocker 460 to pivot in a direction away from one another so as to force the angle between the angular adjustment tab 428 and the first leg 461a of the rocker to increase. This biasing force forces the rocker 460 to pivot relative to the adjustment tab 428 and relative to the guiding arm 457 into the locked state as shown in FIGS. 4C and 4D. As a result, when the user is not pressing down on the adjustment tab 428 and the second leg 461b of the rocker is not operated, the locked state is achieved automatically as a default state.

In the locked state, even when a load is applied to the upper and lower blades of the speculum, the lock formed by the angular adjustment mechanism prevents sliding of the operating mechanism 427 and of the rocker 460 relative to the guiding arm 457, thus maintaining the angular positions of the upper and lower blades relative to one another. The locked state can be released by pushing down on the second leg 461b of the rocker, which compresses the biasing member 465 and causes the rocker 460 to pivot in a direction opposite to the biasing force of the biasing member 465. As a result, the operating mechanism 427 and the rocker 460 can easily slide relative to the guiding arm 457 in either direction for angular adjustment of the blades in either direction. Alternatively, when a user presses down on the adjustment tab 428 of the operating mechanism 427, the rocker 460 is caused to pivot in the direction opposite to the biasing force, reducing the angle between the adjustment tab 428 and the first leg 461a of the rocker and allowing the operating mechanism 427 and the rocker 460 to slide in a direction toward the handle of the speculum, so as to increase the angle between the upper and lower blades of the speculum. In this case, when the user releases the adjustment tab 428, the biasing force of the biasing member 465 causes the rocker 460 to pivot back into the locked state automatically.

It is noted that in any of the locked state, the unlocked/released state and when the user operates the operating mechanism 427 by pressing down on the adjustment tab, the engagement between the guiding arm 457 and the operating mechanism 427, and in particular, the engagement of the guiding arm 457 with the recess 426 of the operating mechanism, is maintained. Therefore, in any of these states, there is no disengagement between the guiding arm 457 and the operating mechanism 427, i.e., the guiding arm 457 is not movable from an engaged position to a disengaged position. Thus, operation of the angular adjustment mechanism 410 is performed without requiring an additional operation by the user to disengage the guiding arm 457 from the operating mechanism 427 in order to provide silent and click-free angular adjustment.

Figure 4F:
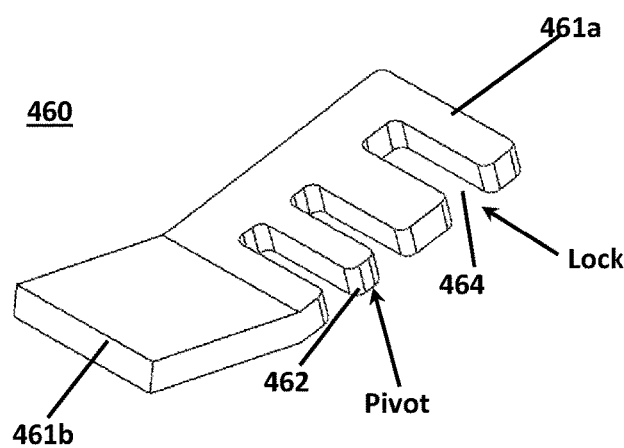
Figure 4G:
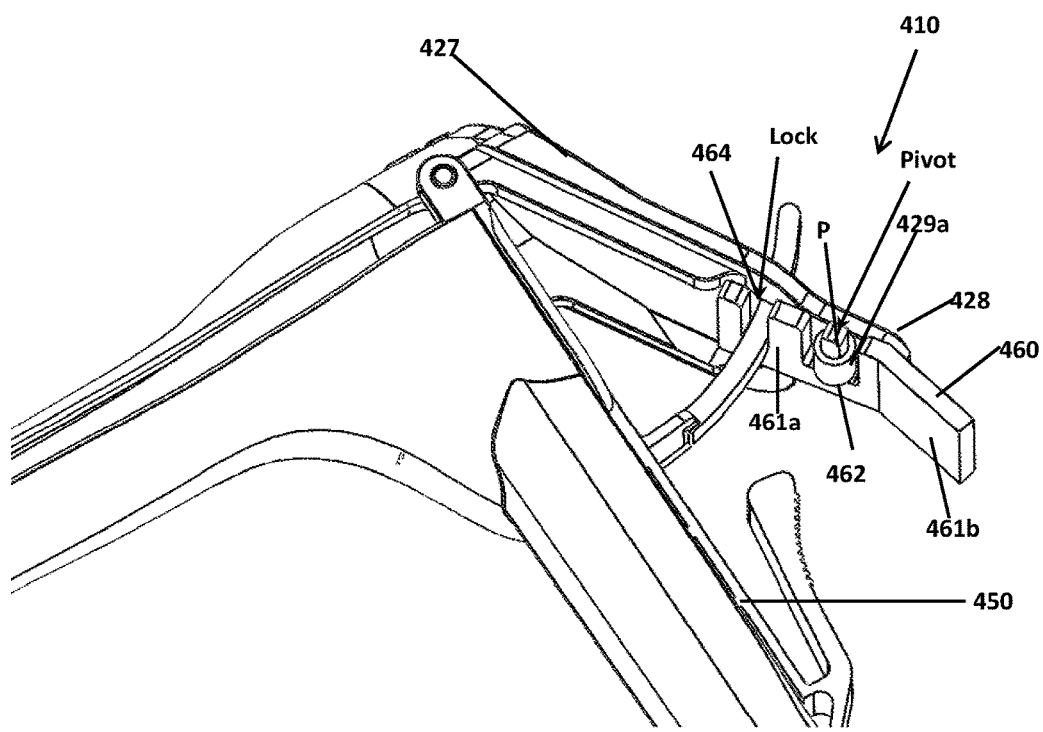

FIG. 4F shows an illustrative configuration of the rocker 460 in more detail and FIG. 4G shows the engagement of the rocker 460 with the operating mechanism 427 and with the guiding arm 457 in more detail. As shown in FIG. 4F, the first leg 461a of the rocker includes a plurality of cutouts, two of which form an arm or a shaft 462 therebetween for engaging with the operating mechanism 427, and a third cutout forming the locking recess 464 for receiving the guiding arm 457. The width of the locking recess 464 is slightly greater than the thickness of the guiding arm 457 so as to allow the rocker 460 to pivot relative to the guiding arm 457 between the locked state and the released state. The rocker is formed from a rigid and non-elastic material, which may be plastic, polymer or metallic material. In some embodiments, the rocker 460 includes a metallic insert or plate (not shown) attached thereto to surround the locking recess 464. The metallic plate may be attached to the surface or a portion of the surface of the rocker and have a recess that corresponds to the locking recess 464 or a recess which may be slightly smaller than the locking recess 464. The metal plate interacts with the guiding arm 457 so as to prevent any sliding of the guiding arm 457 within the locking recess 464 when in the locked state. The metal plate may be attached to one surface of the rocker, e.g., the surface that faces or abuts the operating mechanism 427, or in other embodiments, metal plates may be attached to both surfaces of the rocker.

As shown in FIG. 4G, a bushing 429a is formed on a surface of the operating mechanism 427 facing the linear support member 450 and the shaft 462 of the rocker 460 is inserted into the bushing 429a for pivotable engagement. In the illustrative embodiment of FIG. 4G, the bushing 429a is formed on the surface of the angular adjustment tab 428 facing the linear support member 450. However, the position of the bushing 429a may be adjusted depending on the configuration of the rocker 460 and the configuration of the operating mechanism 427.

In certain embodiments, the bushing and the shaft are configured so that the shaft can be snapped into the bushing so as to prevent disengagement of the rocker 460 from the operating mechanism 427, while allowing pivoting of the rocker 460 relative to the operating mechanism 427. This configuration may be achieved by providing one or more protrusions around an inner surface of the bushing and one or more corresponding recesses around the surface of the shaft portion. Alternatively, one or more protrusions may be provided around the surface of the shaft portion and one or more corresponding recesses may be provided around the inner surface of the bushing. Other snap-in configurations may be provided for preventing disengagement of the rocker 460 from the operating mechanism. Moreover, although the illustrative embodiment shows the bushing being formed on the operating mechanism and the shaft being formed in the rocker, in other embodiments, the shaft may be formed on the operating mechanism while the bushing is formed on the rocker. Other pivotable arrangements may also be used and are not limited to those shown.

As shown in FIG. 4G, the rocker 460 also engages with the guiding arm 457 via the locking recess 464 which receives the guiding arm 457 therein. In the embodiments shown FIGS. 4C-4G, the locking recess 464 is open at one end and the guiding arm 457 is inserted into the locking recess 464, which partially surrounds the guiding arm 457. However, in other embodiments, the locking recess 464 may fully surround the guiding arm 457 on all four sides. As mentioned above, the width of the locking recess 464 is preferably slightly larger than the thickness of the guiding arm 457 so as to allow the guiding arm 457 to easily move during adjustment of the angular adjustment mechanism 410 and to allow for pivoting of the rocker 460 relative to the guiding arm 457.

The locked and unlocked states of the angular adjustment mechanism are described in more detail below with respect to FIGS. 5D-5G, which show a variation of the angular adjustment mechanism 410. As described in more detail below, in the locked state, the rocker 460 is pivoted about a pivot point P of the pivot mechanism 429 so that upper and lower walls of the locking recess 464 in the rocker 460 engage with the guiding arm 457. The biasing member 465 biases the first leg 461a of the rocker 460 to rotate away from the operating mechanism 427, thus keeping the rocker in the locked state as a default position. The engagement between the walls of the locking recess 464 of the rocker and the guiding arm 457, together with the biasing force of the biasing member 465, prevents the operating mechanism 427 and the rocker 460 from sliding relative to the guiding arm 457. When the locked state is released, the rocker 460 pivots or rotates relative to the guiding arm 457 to release the engagement between the walls of the recess 464 and the guiding arm 457, thus allowing the operating member 427 and the rocker to slide relative to the guiding arm 457. As mentioned above, when the second leg 461b is pushed down, the biasing member 465 is compressed, facilitating the pivoting of the rocker and disengagement of the recess walls from the guiding arm 457.

The embodiment shown in FIGS. 4A-4G allows for continuous and silent, i.e., click-free, angular adjustment of the upper blade relative to the lower blade. Since the angular adjustment mechanism 410 does not use ratchet teeth or similar protrusions on the guiding arm, the number of lock positions along the guiding arm is unlimited. The lack of the ratchet teeth contributes to silent angular adjustment. These features result in additional comfort for patients as well as doctors.

Additionally, since the positioning of the angular adjustment tab 428 is not changed from the previous designs, doctors would not require additional training to use the speculum shown in FIGS. 4A-4G, resulting in cost savings and increased proper operation of the angular adjustment mechanism. Since doctors are already used to the positioning and operation of the angular adjustment tab 428, they would not require an adjustment period for comfortable and proper use of the speculum of the present invention. The positioning of the release tab 461b of the rocker directly beneath the angular adjustment tab 428 makes it easy for doctors to access the release tab using the same finger as for the angular adjustment tab 428. The overall ergonomic design of the speculum of the present invention facilitates easier and more comfortable use.

Furthermore, the speculum shown in FIGS. 4A-4G is disposable and is made substantially from plastic materials. In some embodiments, the biasing member 465 may be formed from metallic materials or coated metallic materials, while in other embodiments, a plastic or polymer-based material is used for the biasing member. Exemplary plastic materials that may be used for constructing the speculum of the present invention include, but are not limited to, polypropylene, polystyrene, and any composite of more than one of these plastics and polymers. The upper and lower members may be molded from a colorless transparent plastic material, such as acrylic plastic, polycarbonate or the like. The rocker may be made from the same or similar materials as the speculum or from metallic materials. The linear support member may be formed from a polyester or polyamide material, such as nylon, or the like. All of these components may be formed by injection molding or extrusion or using a 3D printer. In certain embodiments, the materials for forming the speculum, including the rocker and/or the linear support member, of the present invention include glass-fiber reinforced polymers, polyacrylamide compounds, thermoplastic crystalline polymers, thermoplastic crystalline polymers of aromatic diamines and aromatic dicarboxylic anhydrides, glass-fiber reinforced polyacrylamides, and other materials having sufficient rigidity and strength. Due to the low cost of manufacturing the speculum of the present invention, the speculum of the present invention can be cost-effectively made disposable so that there is no need to sterilize the speculum after each use. This greatly reduces the time and cost associated with sterilization procedures and prevents cross-contamination.

FIGS. 5A-5G show variations of the speculum 400 shown in FIGS. 4A-4G. Most of the components of the speculum 400 in FIGS. 5A-5G are the substantially same as the speculum shown in FIGS. 4A-4G and thus, the same reference numbers are used for the same or similar components in FIGS. 5A-5G. Detailed description of the same components of the speculum in FIGS. 5A-5G is omitted. Moreover, the benefits and advantages of the speculum shown in FIGS. 5A-5G are the same as or similar to those of the speculum in FIGS. 4A-4G, and the materials and methods used for manufacturing the speculum of FIGS. 5A-5G are the same as or similar to those for manufacturing the speculum of FIGS. 4A-4G. Therefore, description thereof will be omitted.

Figure 5A:
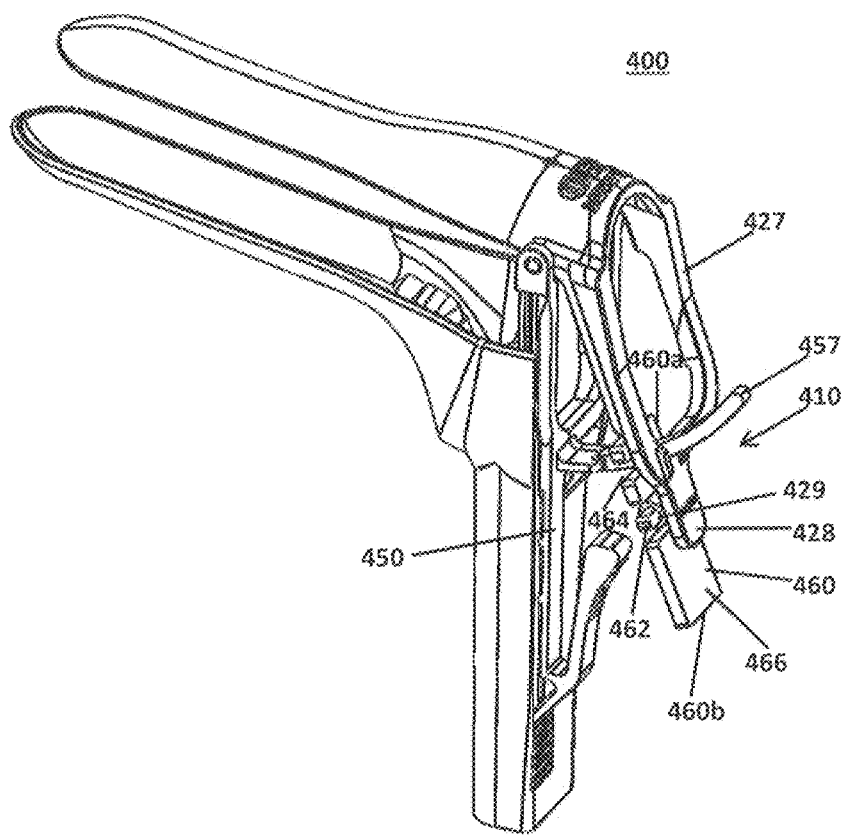
FIGS. 5A-5G show the speculum of FIGS. 4A-4G with a modified first embodiment of the angular adjustment mechanism of the present invention and details of the modified angular adjustment mechanism.
Figure 5B:
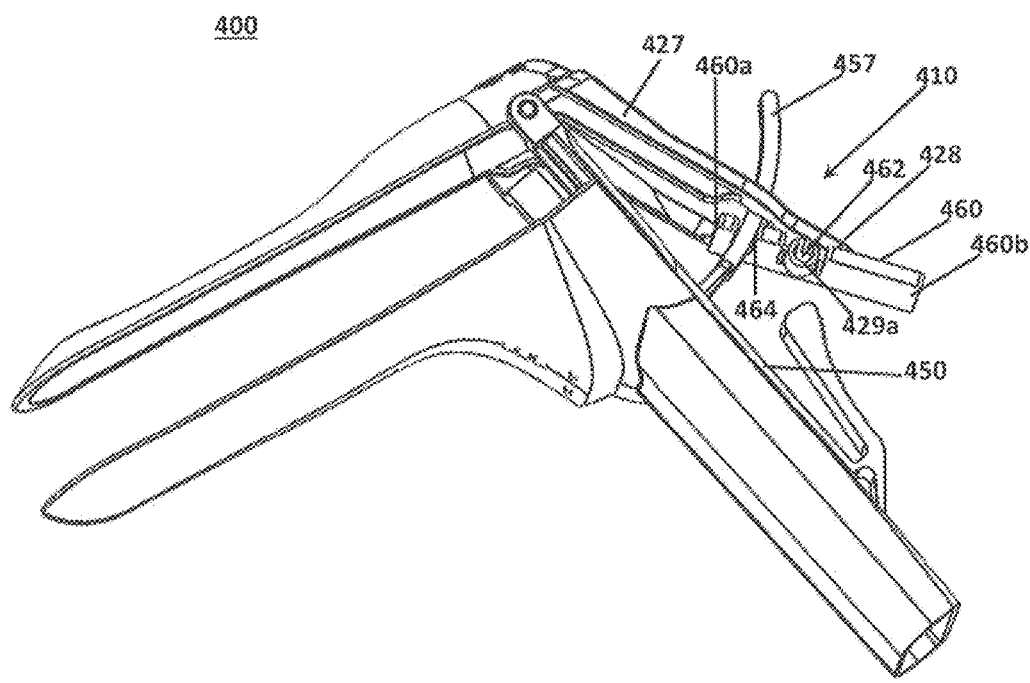
Figure 5C:
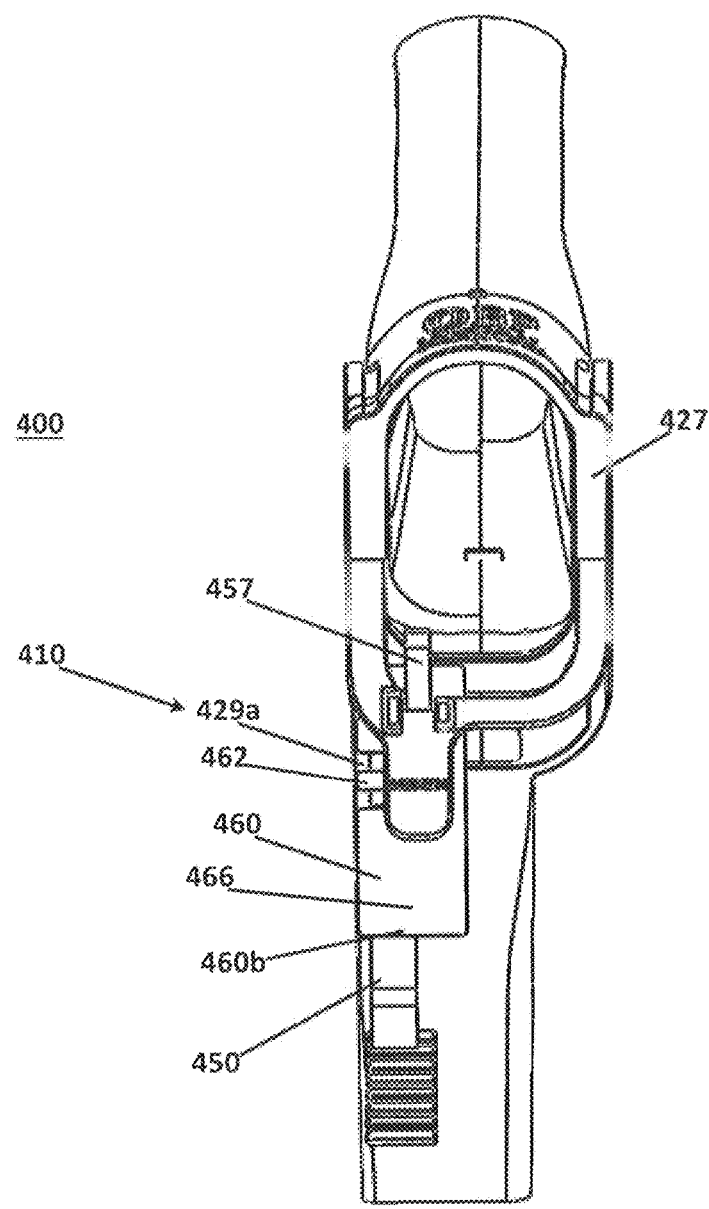

FIGS. 5A-C show views of the speculum from different points of view. In the variations of FIGS. 5A-5G, the rocker 460 of the angular adjustment mechanism 410 is substantially planar or flat, instead of a chevron-shaped member of FIGS. 4A-4G. The rocker 460 of FIGS. 5A-5G has a first end 460a and a second end 460b, and includes a plurality of cutouts in a portion of the rocker 460 closer to the first end 460a, which form an arm or shaft 462 and a locking recess 464. Similar to the speculum of FIGS. 4A-4G, in FIGS. 5A-5G, the shaft 462 is formed between two cutouts in the rocker 460 and is used for engaging with the operating mechanism 427 (e.g., with an angular adjustment tab 428 of the operating mechanism 427) via a bushing 429a of a pivot mechanism 429. The configuration of the pivot mechanism 429 is substantially the same as in the speculum of FIGS. 4A-4G, and thus, the detailed description thereof is omitted. The locking recess 464, which is formed as a third cutout in the rocker 460, receives the guiding arm 457 of the angular adjustment mechanism 410. As in the speculum of FIGS.

4A-4G, the width of the locking recess 464 in FIGS. 5A-5G is slightly greater than the thickness of the guiding arm 457 so as to allow the rocker 460 to pivot relative to the guiding arm 457 between the locked state and the released/unlocked state. As in the previous embodiment, the rocker 460 may include one or more metal plates or metal inserts attached to one or more surfaces thereof around the locking recess 464 so as to ensure that slipping of the guiding arm is prevented when the rocker is in the locked state. The pivoting of the rocker 460 relative to the guiding arm 457 between the locked state and the released/unlocked state are shown in more detail in FIGS. 5D-5G, which are described in more detail below.

Although not visible in FIGS. 5A-5C, the angular adjustment mechanism 410 also includes a biasing member 465, such as a spring, for biasing the angular adjustment tab 428 or another portion of the operating mechanism 427 and a portion of the rocker 460 closer to the first end 460a in a direction away from one another so as to force the angle between the angular adjustment tab 428 and the rocker to increase. As described above with respect to FIGS. 4A-4G, this biasing force causes the rocker 460 to pivot relative to the adjustment tab 428 and also relative to the guiding arm 457 into the locked state.

Figure 5D:
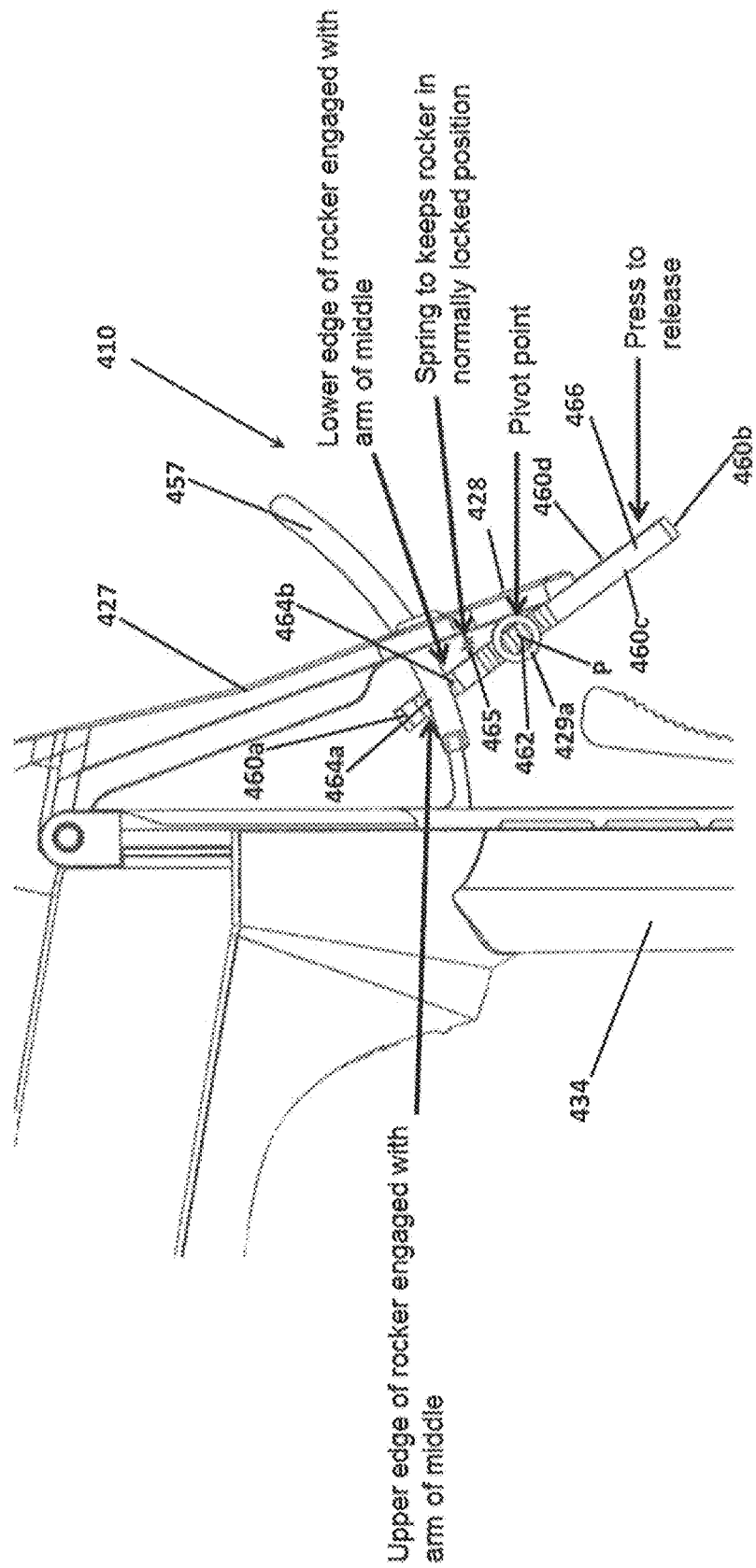
Figure 5E:
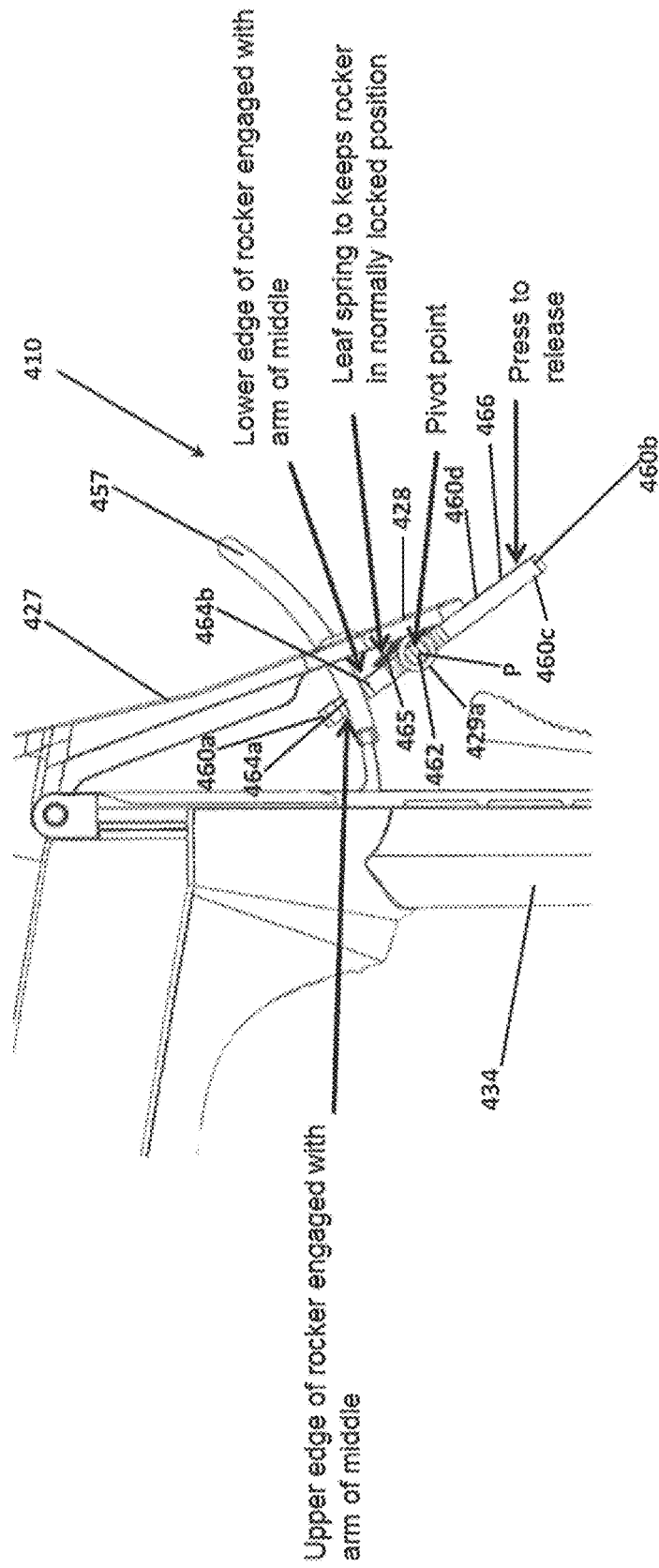
Figure 5F:
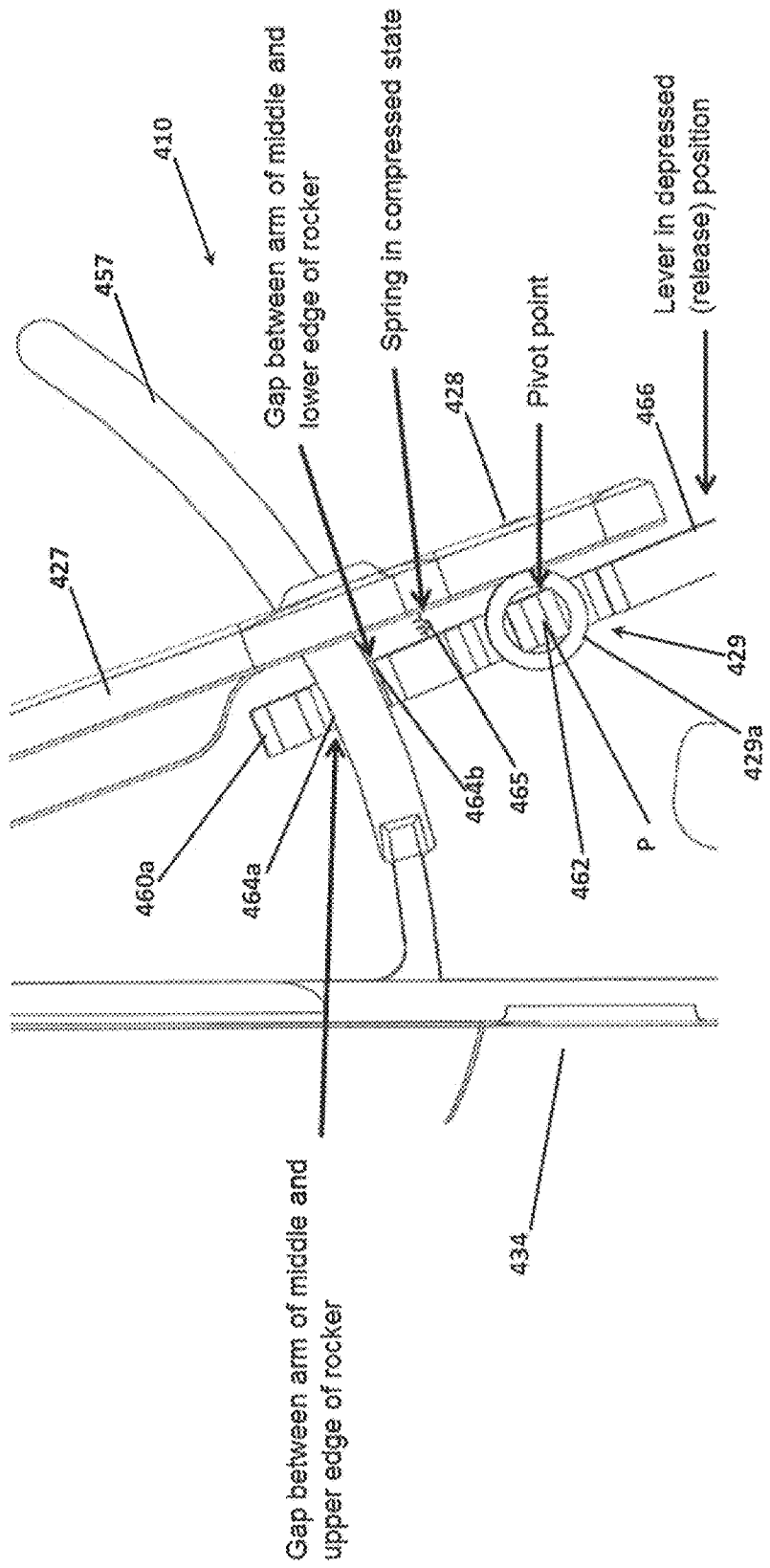
Figure 5G:
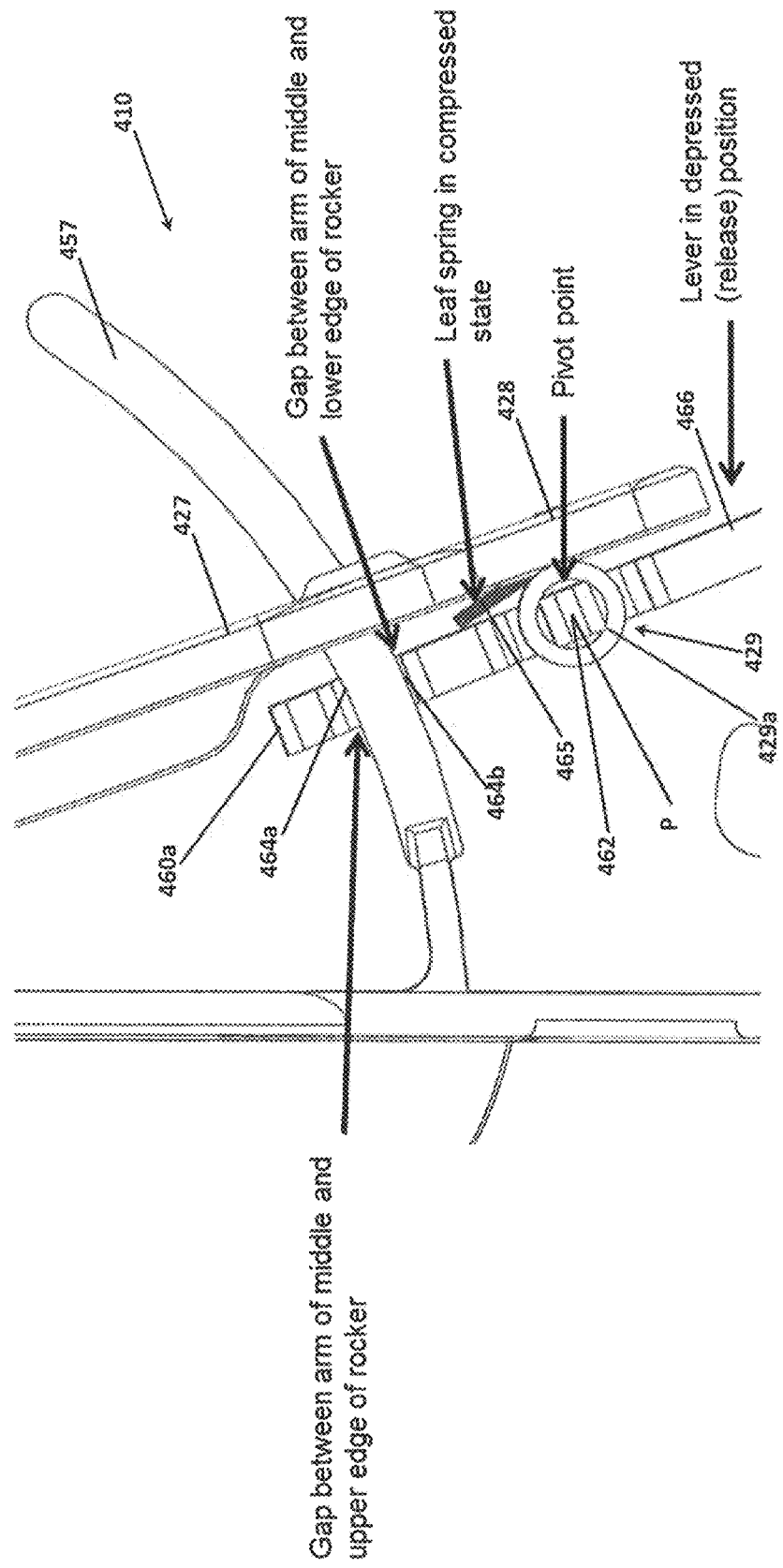

Examples of the speculum 400 of FIGS. 5A-5C in the locked state are shown in FIGS. 5D and 5E, and examples of the speculum 400 of FIGS. 5A-5C in the released/unlocked state are shown in FIGS. 5F and 5G. The main difference between the angular adjustment mechanism of FIGS. 5D and 5F and of FIGS. 5E and 5G is the type of spring used as the biasing member 465. In the angular adjustment mechanism 410 of FIGS. 5D and 5F, a helical spring or the like is used as the biasing member 465 while in FIGS. 5E and 5G, a leaf spring or the like is used as the biasing member 465. It is contemplated that other types of springs are suitable for use as the biasing member 465.

As shown in FIGS. 5D-5G, the rocker 460 has a first surface 460c facing substantially in a direction of the handle 434 of the speculum 400, and a second surface 460d facing substantially in a direction of the operating mechanism 427. In the illustrative embodiments of FIGS. 5D-5G, the biasing member 465 is provided between the second surface 460d of the rocker and the angular adjustment tab 428 of the operating member in an area of the rocker 460 between the shaft 462 and the first end 460a. The biasing member 465 biases against the second surface 460d of the rocker and against the angular adjustment tab 428 so as to pivot the rocker 460 about a pivot point P using the pivot mechanism 429 into the locked state. Thus, the biasing member 465 normally keeps the rocker 460 in the locked state or locked position.

The locking recess 464 of the rocker includes an upper wall 464a and a lower wall 464b and in an unlocked/released state, the upper wall 464a can slide along an upper surface 457a of the guiding arm 457 while the lower wall 464b can slide along a lower surface 457a of the guiding arm 457. As shown in FIGS. 5D-5E, in the locked state, the rocker 460 is pivoted relative to the guiding arm 457 so that the upper wall 464a of the locking recess engages with the upper surface 457a of the guiding arm 457 and the lower wall 464b of the locking recess engages with the lower surface 457b of the guiding arm 457. In the illustrative example of FIGS. 5D-5E, an edge of the upper wall 464a adjacent to the first surface 460c of the rocker engages with the upper surface 457a of the guiding arm 457 and an edge of the lower wall 464b adjacent to the second surface 460d of the rocker engages with the lower surface 457b of the guiding arm 457. The engagement of the locking recess walls 464a, 464b with the guiding arm 457 together with the biasing force of the biasing member 465 keeps the angular adjustment mechanism 410 in the locked state or locked position, preventing the operating member 427 and the rocker 460 from sliding along the guiding arm 457. In addition, in the locked state, the second surface 460d of the rocker 460 also engages with the operating tab 428 at a position closer to the second end 460b of the rocker. This engagement can further strengthen the lock formed by the angular adjustment mechanism 410.

In order the release the locked state shown in FIGS. 5D and 5E, the user can press down on a tab 466 or lever formed at the second end 460b of the rocker. As shown in FIGS. 5F and 5G, when the tab 466 is pressed, the rocker 460 is rotated about the pivot point P of the pivot mechanism 429 to bring the first end of the rocker 460a closer to the operating member 427 and to compress the biasing member 465. This causes the rocker 460 to rotate relative to the guiding arm 457 so that the engagement between the locking recess walls 464a, 464b and the guiding arm 457 is released and the engagement between the second surface 460d of the rocker 460 and the operating tab is also released. As can be seen in FIGS. 5F and 5G, in the unlocked/released state, there is a gap between the upper wall 464a of the recess 464 and the upper surface 457a of the guiding arm 457 and a similar gap between the lower wall 464b of the recess and the lower surface 457b of the guiding arm 457. As a result, the operating member 427 and the rocker 460 can be moved easily relative to the guiding arm 457 so as to make angular adjustments between the upper and lower blades of the speculum. When the angular adjustment mechanism 410 is in the unlocked/released state, angular adjustments can be made continuously along the guiding arm 457 and silently without any clicking noises.

Figure 6D:
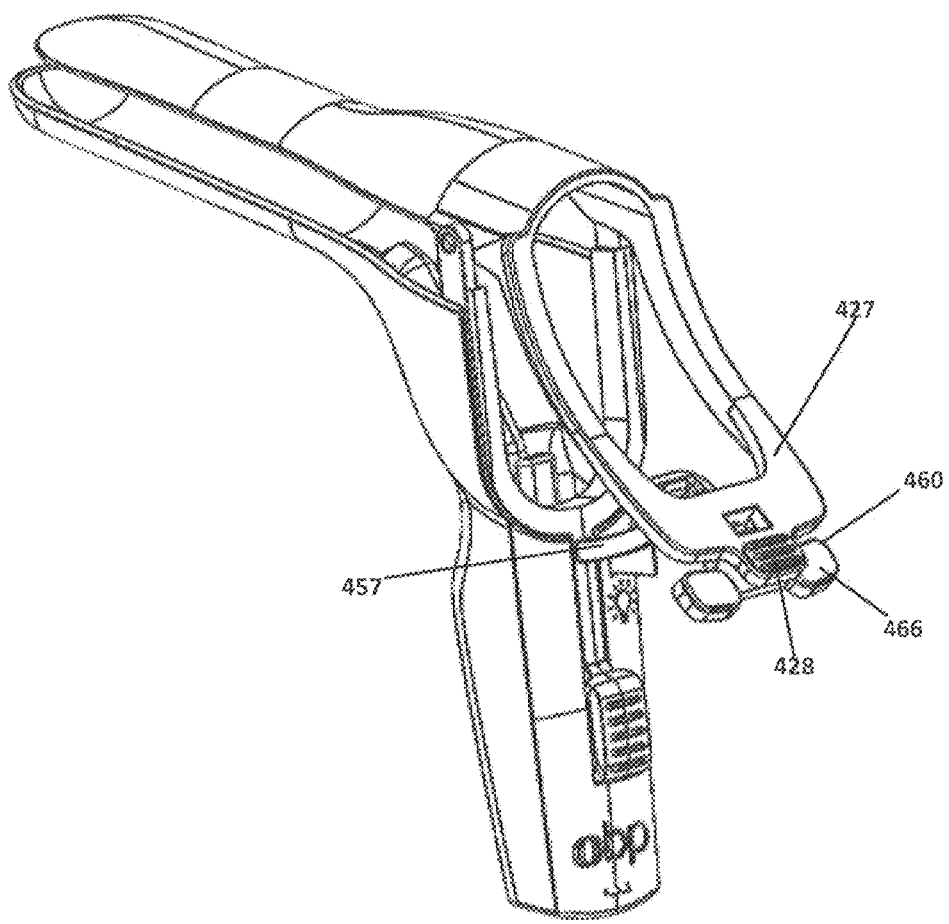
FIG. 6D shows a speculum with the rocker shown in FIGS. 6A-6C.

FIGS. 6A-6C show another configuration of the rocker 460 for use in the speculum shown in FIGS. 4A-5G and FIG. 6D shows the rocker 460 of FIGS. 6A-6C being used in a speculum. As shown, the rocker 460 of this embodiment has a slightly curved shape, includes two through openings or recesses 463 and 464 and one or more tabs or levers 466 provided on one or both sides of the rocker 460. In other variations, the rocker 460 may be planar or may have a greater curvature, e.g., chevron shaped. In the specific embodiment of FIGS. 6A-6C, the rocker 460 includes a first recess 463 which is configured to accommodate a pivot, e.g., a pivot pin or shaft, for pivotably engaging with the operating mechanism 427. Although not shown, the pivot pin would be provided within the first recess 463 between the side walls and would engage with the operating mechanism 427. A projection on the operating mechanism 427 maybe formed, similar to the one shown in the previous embodiments, and the pivot pin would pass through the projection. In addition, the projection may be sized so as to be accommodated within the first recess 463 (as can be seen in FIG. 7B).

The rocker 460 also includes a second through opening 464, which forms a locking recess, for receiving the guiding arm 457 of the speculum, wherein the guiding arm 457 passes through the second opening 464. As in the previous embodiments, the width of the locking recess 464 is slightly greater than the thickness of the guiding arm 457 so as to allow the rocker 460 to pivot relative to the guiding arm 457 between the locked state and the released state. As in the previous embodiments, the body or main portion of the rocker 460 is formed from a rigid and non-elastic material, which may be plastic, polymer or metallic material.

In FIGS. 6A-6C, the rocker 460 of this embodiment includes a tab or lever 466 extending from each side thereof.

Although this illustrative embodiment has a pair of tabs or levers 466 for convenience, in other variations, only one tab/lever may be provided so as to extend from only one side of the rocker 460. The tab or lever(s) 466 are configured to be operated by the user to unlock the locked state of the rocker 460 when a user pushes down on one or both tabs/levers. As can be seen from FIG. 6D, when the rocker 460 is engaged with the operating member 427, the tab(s)/lever(s) 466 are positioned on each side of the angular adjustment tab 428 on the operating member 427. This positioning of the tab(s)/lever(s) 466 provides an ergonomic design wherein the user can operate the angular adjustment tab 428 and the tab(s)/lever(s) 466 with the same finger without requiring additional movements or adjustments of the user's hand holding the speculum.

As shown in FIGS. 6A-6C, the rocker 460 includes a metal insert 467 or metal plate provided around the locking recess 464 so as to prevent any slippage due to plastic to plastic friction between the locking recess 464 and the guide arm 457. The metal insert creates a metal edge to plastic joint between the locking recess 464 and the guide arm 457, thus ensuring that the locked state is retained even when a heavy load is applied to the speculum blades. The assembly of the metal insert 467 with the rocker 460 is demonstrated in FIGS. 6A-6C.

As shown, a partially recessed portion 464c is formed around the locking recess 464 in the surface of the rocker so as to accommodate the metal insert 467 therein. The partially recessed portion 464c also includes one or more projections or ribs 464d at the periphery of the partially recessed portion 464c. The metal insert 467, which comprises a thin metal plate, is inserted into the partially recessed portion 464c so that one or more ribs 464d are adjacent to the periphery of the metal insert 467. The one or more ribs 464d are then heat stacked by heating them so as to melt them and forming them to partially overlap with peripheral edges of the metal insert 467. In this way, the metal insert 467 is held within the partially recessed portion 464c by the heat stacked ribs overlapping therewith. Other methods of attaching the metal insert 467 to secure it within the partially recessed portion 464c, including use of adhesives or molding techniques. Although FIGS. 6A-6C show the metal insert 467 being provided on one side of the rocker, in other embodiments, metal inserts 467 may be used on both sides of the rocker. In yet other embodiments, other rigid, non-metallic, materials may be used instead of metal for the insert 467.

Figure 7A:
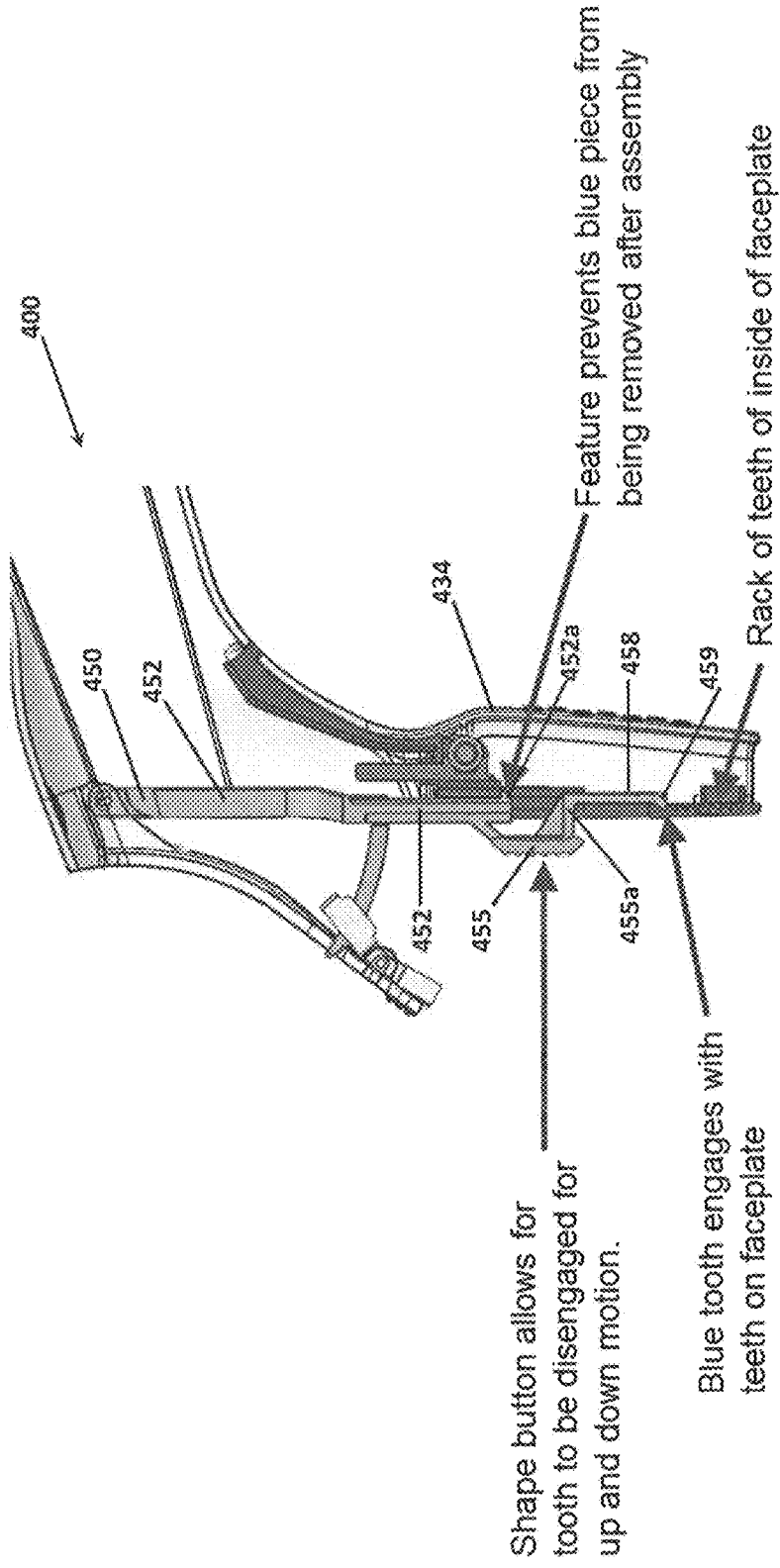
FIGS. 7A-7C show the speculum of FIGS. 4A-4G with a second embodiment of a vertical adjustment mechanism.
Figure 7B:
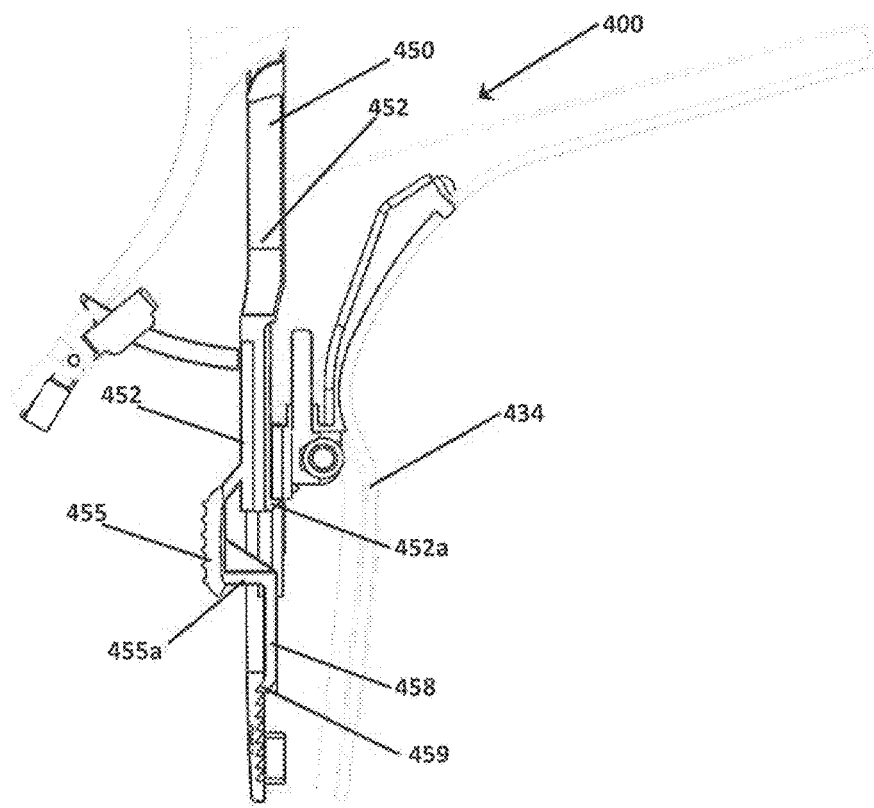
Figure 7C:
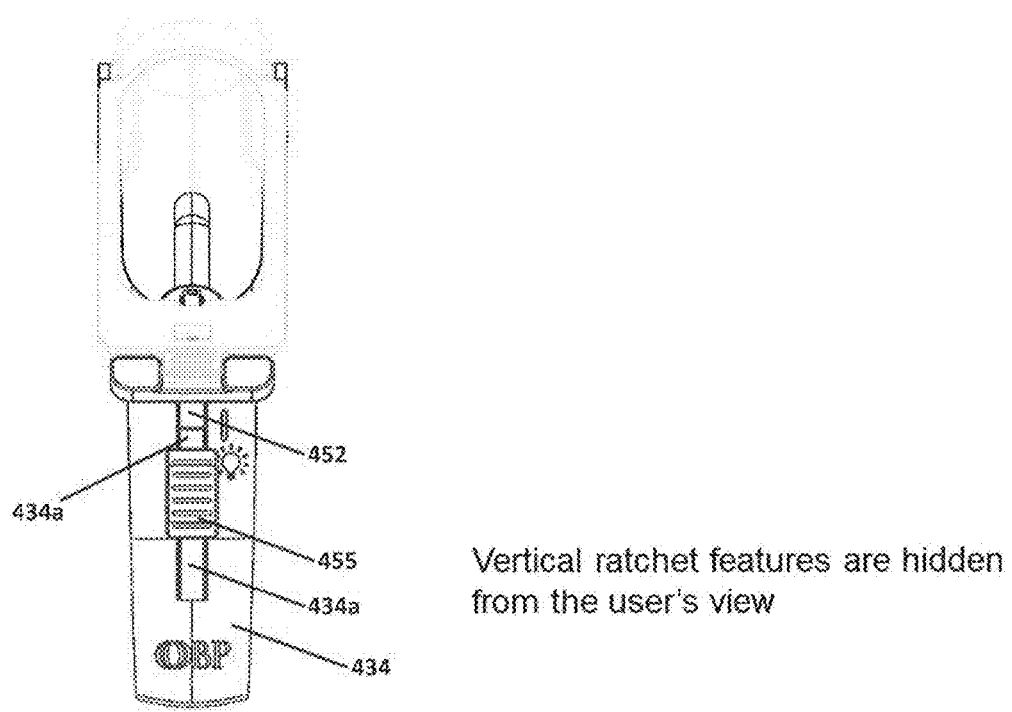

FIGS. 7A-7C show the speculum 400 of FIGS. 4A-5G with a modified vertical adjustment mechanism and using the rocker 460 of FIGS. 6A-6C. FIGS. 7A and 7B show a cross-sectional view of a portion of the speculum 400 to demonstrate ratchet features of the vertical adjustment mechanism, and FIG. 7C shows an external view of the speculum, in which the ratchet features of the vertical adjustment mechanism are hidden from view.

In FIGS. 7A-7C, the speculum 400 includes a modified linear support member 450 having an elongated body 452. In the embodiments of FIGS. 4A-5G, the linear support member is asymmetrical and is provided closer to one side of the handle. However, in the illustrative embodiments of FIGS. 7A-7C, the linear support member 450 is substantially symmetrical and extends substantially centrally with respect to the handle. However, it is contemplated that the embodiments of FIGS. 4A-5G may be modified so that the linear support member is substantially symmetrical and extends centrally relative to the handle, and the embodiment of FIGS. 7A-7C may be modified to make the linear support member 450 asymmetrical and provided closer to one of the sides of the handle.

Moreover, instead of the elevation leg provided in the mechanism of FIGS. 3A-3B, in this embodiment, a lower end of the elongated body 452 has a button 455 extending outwardly relative to the speculum handle 434, and downwardly from the lower end of the elongated body 452. The outer surface of the button may include ridges, protrusions, an in-molded pattern or other three-dimensional elements or frictional elements so as to prevent slipping of the user's finger. The shape of the outer surface of the button 455 may vary and may be configured to be slightly concave and/or to include outwardly protruding rims at the upper and lower ends thereof and/or from the sides thereof so as to improve comfort of the user while performing vertical adjustment.

A lower end of the button 455 has a lip 455a extending in the direction toward the speculum handle 434. In this way, the button 455 is configured to form a step that protrudes outwardly from the lower end of the elongated body 452. In addition, as shown in FIGS. 7A-7B, a vertical engagement arm 458 extends from the lip 455a in a downward direction and includes a locking tooth 459 protruding from its lower end. The locking tooth 459 protrudes outwardly so as to engage with stop tabs formed on the inner surface of the handle. When a user presses the button 455 to move it slightly in a direction toward the handle 434, the locking tooth 459 disengages from the stop tabs to allow for vertical adjustment. After the button 455 is released, the locking tooth 459 again engages with the stop tabs on the handle's inner surface and thus prevents further vertical movement of the linear support member 450 relative to the handle.

As also shown in FIGS. 7A and 7B, the lower end of the elongated body 452 includes a retaining projection 452a protruding in a direction towards the handle and opposite to the direction of the button 455. The retaining projection 452a is configured to engage with the handle 434 to prevent vertical movement of the linear support member 450 beyond a predetermined position. The engagement of the retaining projection 452a with the handle 434 prevents removal and disengagement of the linear support member 450 from the handle 434. In FIGS. 7A and 7B, the linear support member 450 is positioned at the predetermined position, in which the retaining projection 452a is engaged with the handle 434 and the upper and lower blades are at a maximum vertical adjustment position. From this position, the linear support member 450 is prevented from moving vertically in an upward direction relative to the handle 434 to further increase the vertical adjustment between the upper and lower blades, but can be moved vertically in a downward direction relative to the handle 434 to reduce the vertical adjustment between the upper and lower blades.

When the linear support member 450 is assembled with the handle 434, the elongated body 452 slides into a recess 434a formed in the handle 434 or in a rear faceplate forming a back wall of the handle 434 to engage with sidewalls forming the recess 434a until the engagement tooth 452a engages with the handle. At the same time, the engagement arm 458 is inserted into a lower portion of the recess 434a in the handle and is pushed down so that it extends along the inner surface of the handle wall. As shown in FIGS. 7A-7C, in the assembled state, the elongated body 452 is engaged with the sidewalls forming the recess 434a in the handle, the button 455 protrudes outside the handle, the engagement arm 458 extends inside the handle along the inner surface of the handle wall and the tooth 459 engages with the stop tabs formed on the inner surface of the handle wall. As can be seen in FIGS. 7A-7B, the retaining projection 452a engages with an inner structure within the handle and prevents the linear support member 450 from moving beyond the predetermined position relative to the handle so as to prevent disengagement of the linear support member from the handle.

Figure 8A:
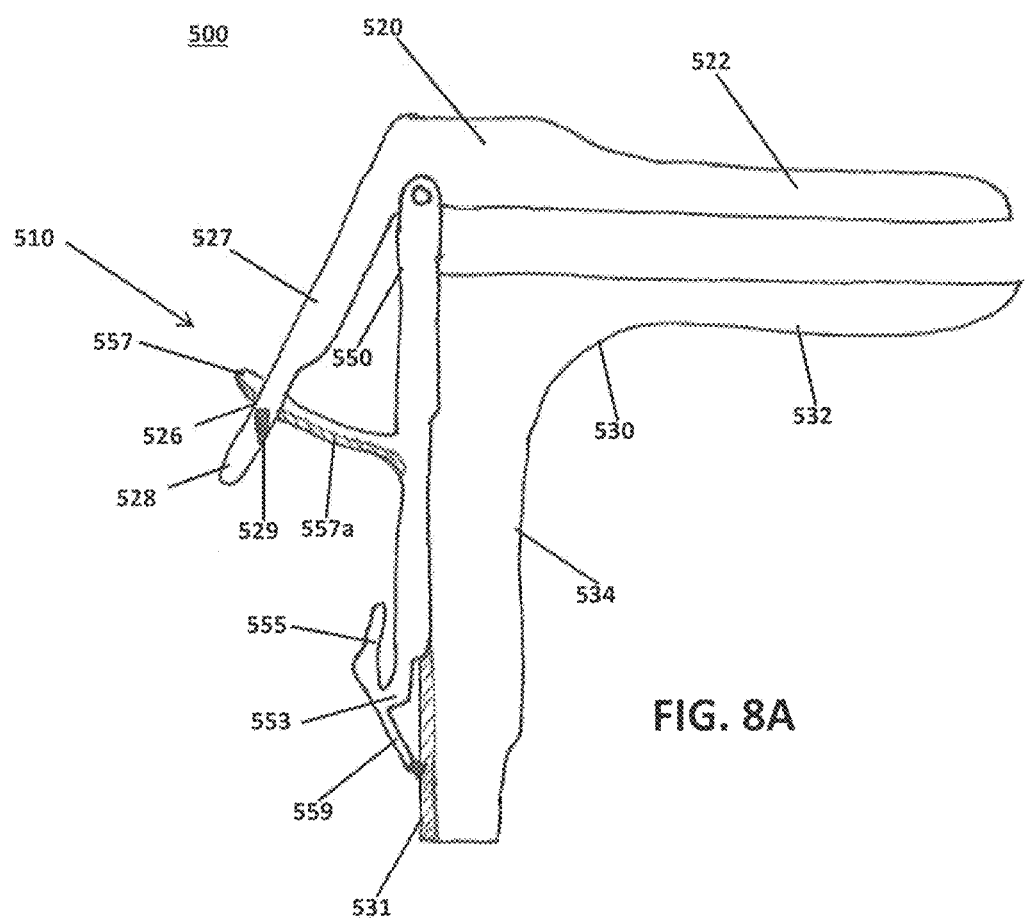
FIGS. 8A-8B show a speculum with a second embodiment of an angular adjustment mechanism.
Figure 8B:
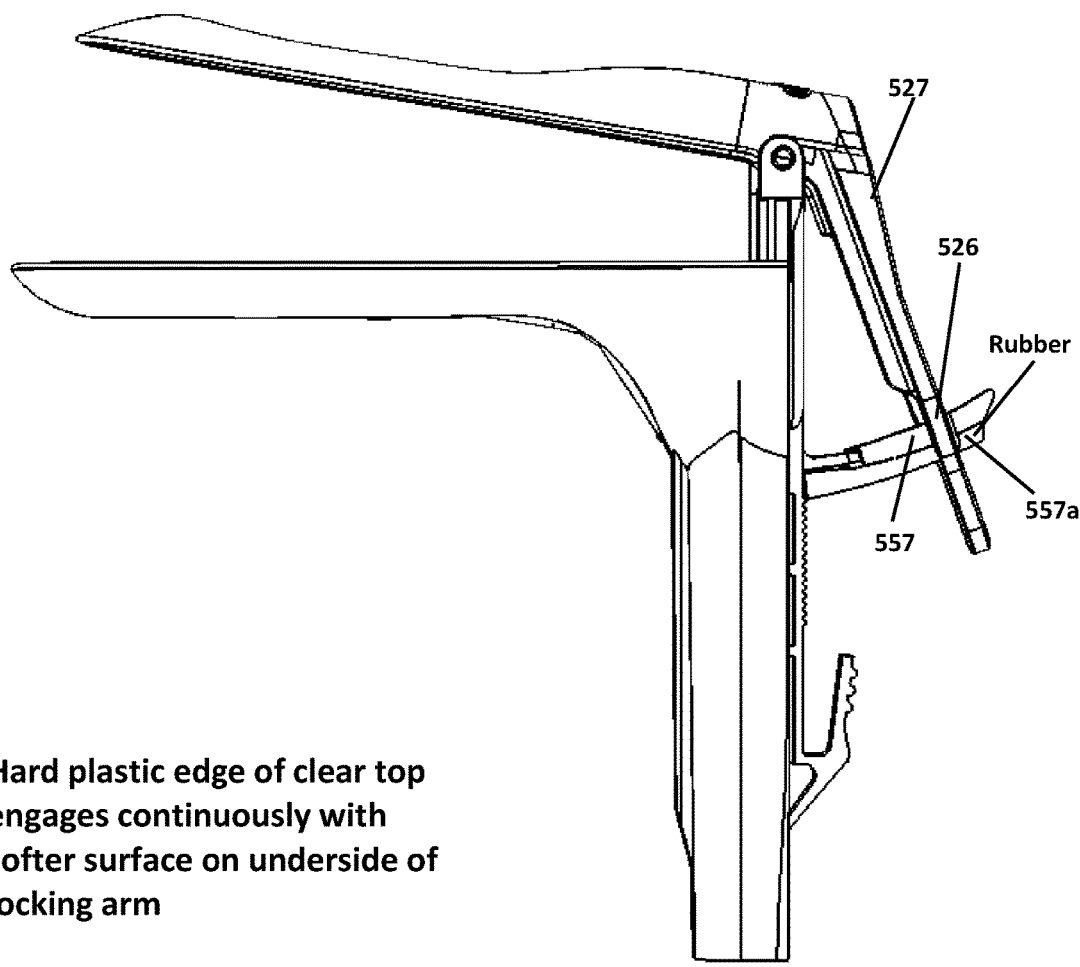

FIGS. 8A-8B show a speculum 500 that includes another embodiment of a continuous angular adjustment mechanism 510. In FIGS. 8A-8B, the speculum 500 includes an upper member 520 with an upper blade 522 and an operating mechanism 527 extending outwardly and downwardly from a proximal end of the upper blade 522. The speculum 500 also includes a lower member 530 with a lower blade 532 and a handle 534, and further includes a linear support member 550 with a guiding arm 557 extending from about a midpoint thereof, a lip 553 extending from a lower end thereof, and an elevation leg 555 and locking tooth 559 extending from the lip 553. The top of the linear support member 550 is hinged to the upper member 520 and an elongated body 552 of the linear support member 550 is slidably engaged with the lower member 530. The angular adjustment mechanism 510 of this embodiment includes the guiding arm 557 and the operating mechanism 527, which can be moved along the length of the guiding arm 557 and lockably engage with the guiding arm 557. In the present invention, the guiding arm 557 does not include ratchet teeth for engagement with the operating mechanism. As a result, continuous angular adjustment is achieved, without clicking sounds during the adjustment.

In the present illustrative embodiment, the operating mechanism 527 includes an opening 526 through which the guiding arm 557 passes and an angled tooth 529 disposed in the opening 526 with which the guiding arm 557 engages into a locking state. In some embodiments, the opening 526 may be open at one end into the yoke portion of the operating mechanism 527, as in the conventional speculum, or may be configured to fully surround the guiding arm 557. The opening 526 includes the angled tooth 529, which is angled in a direction toward an outer end of the guiding arm 557. The angled tooth 529 may be angled at about a 45-degree angle relative to the lengthwise plane of the operating mechanism 527. However, in other embodiments, the angle of the angled tooth 529 will vary so as to optimize engagement with the guiding arm 557.

In the present illustrative embodiment, the lower surface (underside) of the guiding arm 557 is formed from a softer material, such as softer plastics and polymers, rubber, silicone, and the like. The softer material may be provided as a coating 557a on the surface or partial surface of the guiding arm 557. The softer material may be adhered or bonded to the surface or partial surface of the guiding arm 557, or may be embedded into the surface of the guiding arm 557.

When the operating mechanism 527 is operated by a user by pressing down on the tab 528, the operating mechanism 527 slides relative to the guiding arm 557, and when the operation is completed, the angled tooth 529 digs into the softer material 557a on the surface of the guiding arm 557, preventing movement of the operating mechanism 527 relative to the guiding arm 557 in a reverse direction. Thus, the user can increase the angle between the upper and lower blades by pressing down on the tab 528 and automatically lock the operating mechanism 527 in the adjusted position relative to the guiding arm 557. If the user desires to release the locking state between the operating mechanism 527 and the guiding arm 557, the user would need to press up on the outer end of the guiding arm 557, thus disengaging the angled tooth 529 from the softer material 557a.

As shown in FIG. 8A, the translational mechanism may be similarly configured by replacing the stop tabs formed on a lower surface of the handle with similar softer material 531. A locking tooth 559 on the linear support member 550 includes a sharp tip and engages with the softer material 531 by digging into the softer material so as to prevent movement in a reverse direction after translational adjustment is made. The locking tooth 559 may be made from polymer or plastic materials, from metallic materials or any other suitable materials. In order to disengage the locking tooth 559 from the softer material 531, the elevation leg 555 is pressed so as to lift the locking tooth 559 from the softer material 531. Although in FIGS. 8A and 8B, the elevation leg 555 has a conventional configuration, in other variations of this embodiment, the elevation leg 555 has a configuration as shown in FIGS. 3A-3B and described above for more comfortable operation. Alternatively, the vertical adjustment mechanism described above and shown in FIGS. 7A-7C may be used.

As in the previous embodiment, this embodiment allows for silent and continuous operation due to the lack of ratchet teeth. In addition, the embodiment of FIGS. 8A-8B does not require disengagement of the guiding arm 557 from the operating mechanism 527 in order to increase the angle between the upper and lower blades silently and continuously. As in the prior embodiments, most if not all of the components of the speculum are formed from plastic and/or polymer materials, thus reducing manufacturing and materials costs. This allows for cost effective manufacture of disposable speculums which do not have to be sterilized after each use, thus further reducing costs associated with cleaning and sterilizing equipment and preventing cross-contamination between patients. Furthermore, since the angular adjustment operations by the doctors in this embodiment are similar to what the doctors are used to, there is no need for additional training to use the speculum of this embodiment, thus further reducing training costs.

Figure 9D:
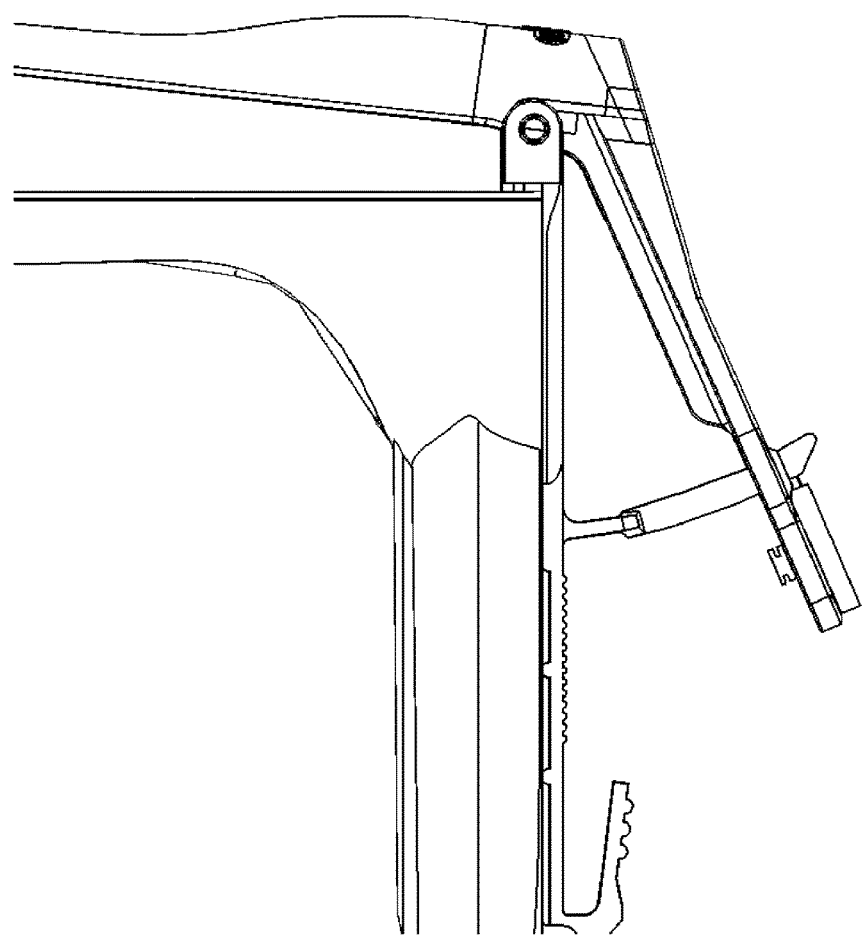

FIGS. 9A-9C schematically show another speculum 600 with another embodiment of a silent angular adjustment mechanism 610. FIG. 9D shows a photograph of the speculum 600 of FIGS. 9A-9C. The general configuration of the speculum 600 is similar to those of the previous embodiments, with the exception of the angular adjustment mechanism 610, which includes a guiding arm 657 of the linear support member 650, an operating mechanism 627 of the upper member 620 and a sliding lock 665. As in the other embodiments, the operating mechanism 627 includes an opening 626 (not visible) for slidably engaging with the guiding arm 657, and the opening 626 may be partially open or may surround the guiding arm 657 on all sides. The operating mechanism 627 also includes an angular adjustment tab 628, wherein the sliding lock 665 is slidably engaged with the angular adjustment tab 628. In other embodiments, the sliding lock 665 may be provided on other portions of the operating mechanism 627.

As shown in FIGS. 9A-9C, the guiding arm 657 includes a plurality of slots or openings 657a, which define different angular adjustment steps. Although the openings 657a are shown as through openings that extend through the entire thickness of the guiding arm 657, in other variations, the openings 657a may extend through only a portion of the thickness of the guiding arm 657. The sliding lock 665 includes a locking tip which is adapted to pass through or pass into the openings 657a. Although the openings are shown as being rectangular in shape, other shapes are contemplated. In certain embodiments, slit openings are provided with small intervals between them so as to increase the number of predetermined steps of angular adjustment and to decrease the size of each step. In such embodiments, the locking tip of the sliding lock 665 would be sized so as to fit into each of the slit openings, e.g., the locking tip may be a flat tab-shaped tip or a pin shaped tip.

Although FIG. 9C shows the steps being at regular intervals, in some embodiments, the intervals may vary along the length of the guiding arm. For example, the intervals near the outermost end of the guiding arm may be greater, so as to enable larger steps of angular adjustment at the beginning of adjustment, and may become smaller in a direction toward the handle of the speculum.

In operation of the angular adjustment mechanism 610, the user slides the sliding lock 665 in a downward direction away from the guiding arm 657 to disengage a locked state between the operating mechanism 627 and the guiding arm 657. This allows the user to move the operating mechanism 627 relative to the guiding arm 657 so as to angularly adjust the upper blade relative to the lower blade. After adjusting the operating mechanism 627 relative to the guiding arm 657, the angular adjustment is locked by releasing the sliding lock 665 so that its locking tip engages with one of the openings 657a. The locking operation may be performed by the user by actively sliding the sliding lock 665 into one of the openings 657a. Alternatively, the sliding lock 665 may be biased by a biasing member, such as a spring, to force the sliding lock 665 to return to the locked state, so that when the user releases the sliding lock 665, it automatically returns to the locked state and is inserted into one of the openings 657a.

Although the speculum in FIGS. 9A-9B has a limited number of predefined locked positions, the angular adjustment mechanism 610 can be operated silently and without requiring disengagement of the guiding arm 657 from the opening 626 in the operating mechanism 627. In addition, as before, all or substantially all of the components are formed from plastic or polymer materials, and the speculum is preferably a one-time use disposable speculum. Furthermore, the operation of the angular adjustment mechanism is simple and does not require additional training.

Figure 10:
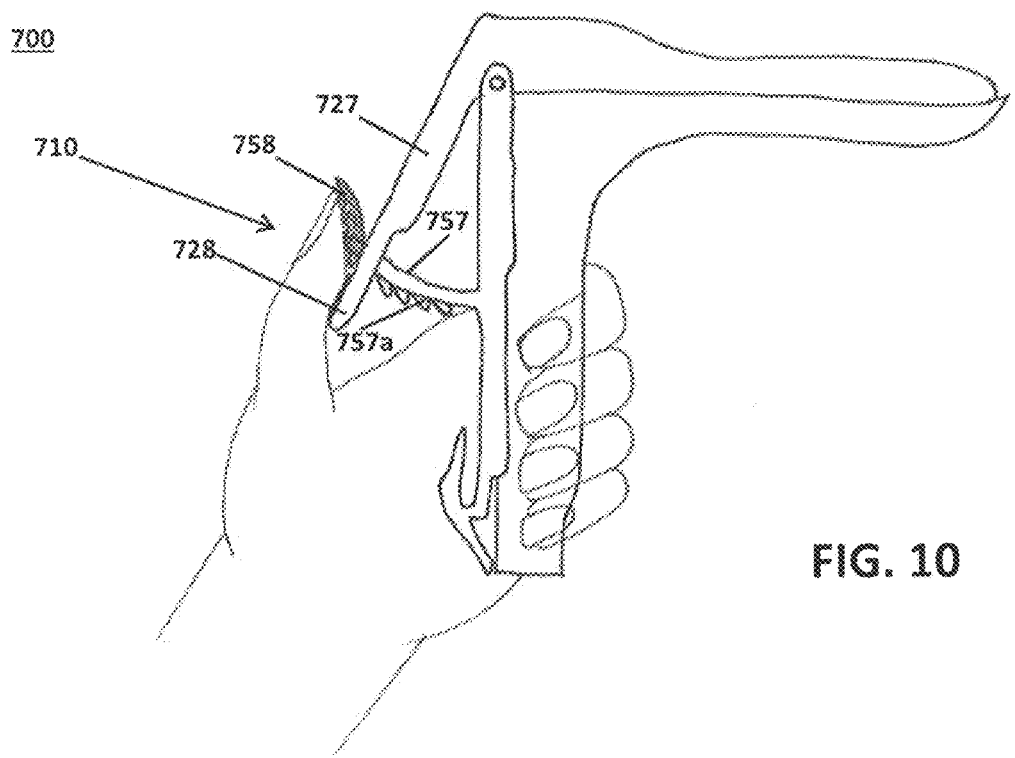
FIG. 10 shows a speculum with a fourth embodiment of an angular adjustment mechanism.
Figure 11:
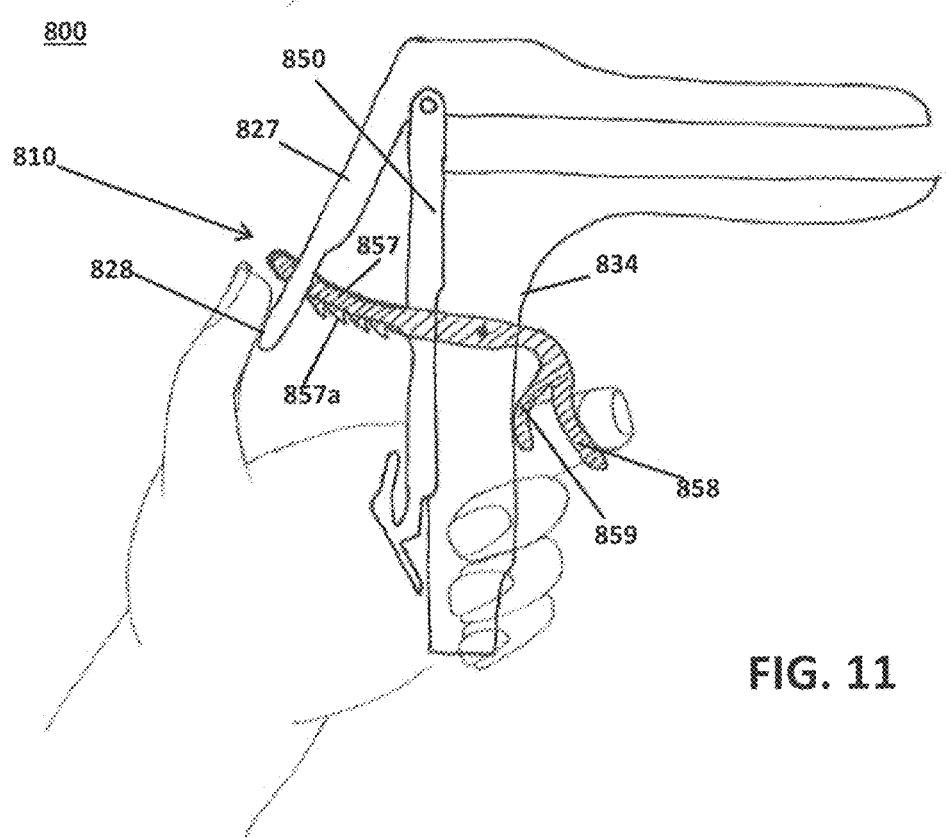
FIG. 11 shows a speculum with a fifth embodiment of an angular adjustment mechanism.

Other embodiments that use ratchet teeth on the guiding arm with stepped angular adjustment are also contemplated by the present invention. In FIGS. 10 and 11, the angular adjustment mechanism 710, 810 of the speculum includes a guiding arm 757, 857 with ratchet teeth 757a, 857a provided thereon for engaging with the operating mechanism 727, 827. Specifically, the guiding arm 757, 857 is preferably slidably disposed within an opening in the operating mechanism 727, 827 and the ratchet teeth 757a, 857a engage with an end wall of the opening or with a locking portion formed in the opening. The angular adjustment mechanism 710, 810 in the embodiments of FIGS. 10 and 11 can be operated so as to disengage the ratchet teeth 857a, 857a of the guiding arm 757, 857 from the end wall or locking portion of the opening during angular adjustment.

In FIG. 10, a release tab 758, such as a paddle-shaped tab, is provided on the end or tip of the guiding arm 757. Operating the release tab 758, e.g., by pressing on it, causes the guiding arm 757 to be lifted so as to disengage the ratchet teeth 757a from the operating mechanism 727. At the initial stage of angular adjustment, i.e., when the operating mechanism 727 is near the tip of the guiding arm 757 and the blades are in a closed state, the release tab 758 is positioned to be adjacent to or near an angular adjustment tab 728 on the operating mechanism 727. In the illustrative embodiment shown, the release tab 758 is directly above the angular adjustment tab 728. In this way, the release tab 758 can be operated simultaneously with pressing down on the angular adjustment tab 728 using only one finger so that the user can disengage the ratchet teeth 757a from the operating mechanism 727 while moving the operating mechanism 727 along the guiding arm 757 for angular adjustment.

In FIG. 11, the guiding arm 857 is formed separately from the linear support member 850 and either passes through an opening in the linear support member and/or an opening in the handle or extends outside of the linear support member and the handle, e.g., on one side of the linear support member and the handle. The guiding arm 857 is pivotably engaged with the handle 834 or with the linear support member 850 and includes a release tab 858 that can be operated to release the engagement between the ratchet teeth 857a on the guiding arm 857 and the operating mechanism 827. The release tab 858 extends in front of the handle 834 so that it can be operated by a doctor's index finger while the doctor's thumb operates an angular adjustment tab 828 for angular adjustment. In certain embodiments, a biasing arm 859 is provided on the guiding arm 857 that requires sufficient force to be applied to the release tab 858 in order to move the guiding arm 857. The biasing arm 859 prevents accidental disengagement of the ratchet teeth 857a from the operating mechanism 827. In other variations, the biasing arm 859 may be replaced by other mechanism(s) that prevent accidental disengagement of the ratchet teeth.

Although the angular adjustment mechanisms of FIGS. 10 and 11 use ratchet teeth and require disengagement of the ratchet teeth from the operating mechanism 727, these angular adjustment allow for silent and click-free operation of the angular adjustment mechanism. In addition, these mechanisms have a relatively simple construction and do not require many additional parts or a complex arrangement thereof. All or most of the components can be formed from plastic or polymer materials, and the specula of these embodiments may be made disposable specula. Furthermore, the ergonomic designs of these embodiments take advantage of usual contact points to force the doctor to disengage the ratchet teeth before making angular adjustments.

Figures 12A, 12B:
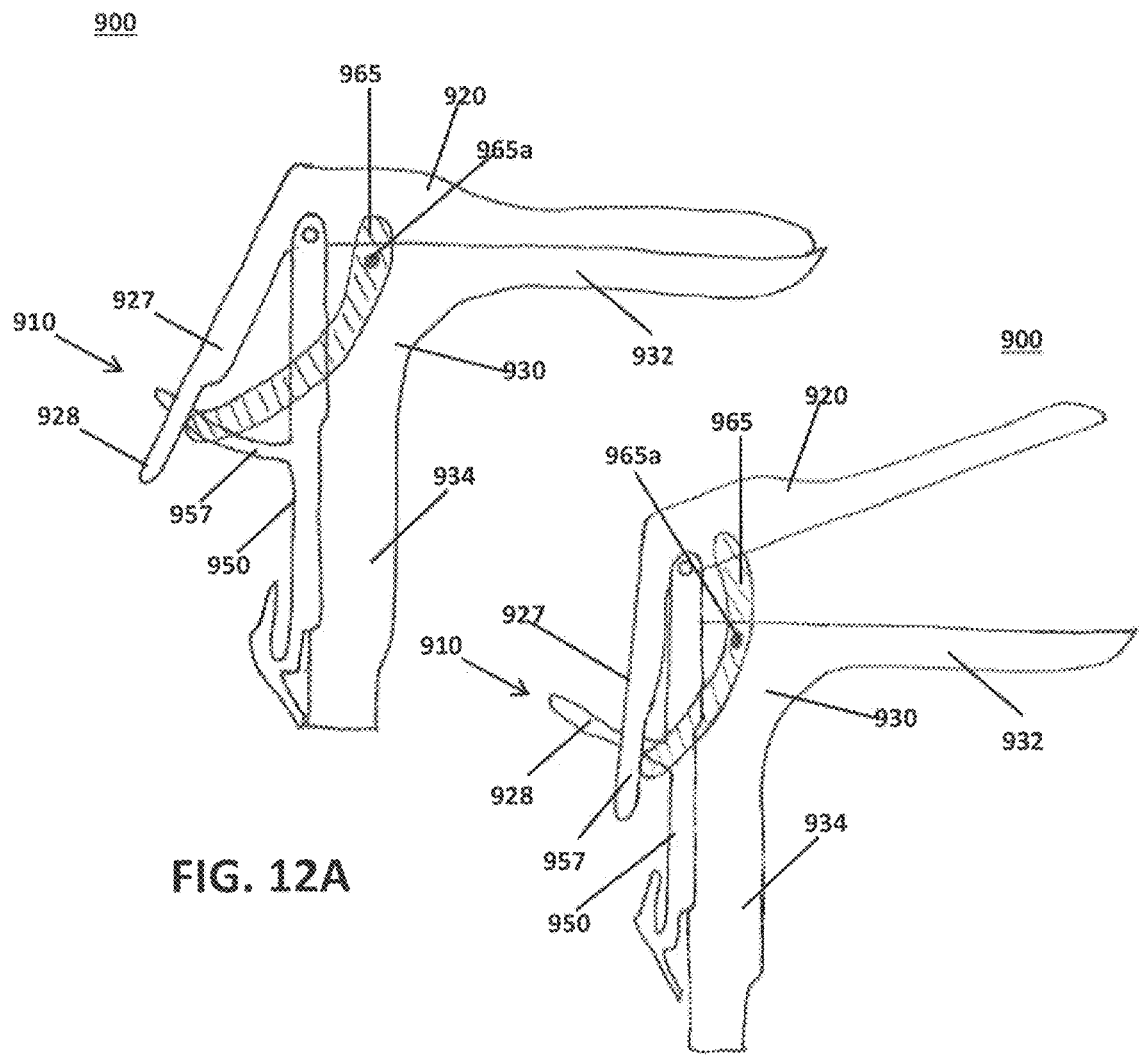
FIGS. 12A-12B show a speculum with a sixth embodiment of an angular adjustment mechanism.

Other possible variations of silently operating angular adjustment mechanisms are shown in FIGS. 12A-12B and 13A-13B. FIGS. 12A and 12B show a single actuation adjustment mechanism 910 which is used for simultaneous angular and translational adjustment of the upper blade relative to the lower blade. An additional translational mechanism may be provided similar to those shown in the other embodiments described herein above. As shown in FIGS. 12A and 12B, the single actuation mechanism 910 includes a guiding arm 957 of the linear support member 950, an operating mechanism 927 including an opening for slidably engaging with the guiding arm 957, and a locking arm 965, which is used for controlling the adjustment of the upper blade and for locking the adjustment position of the operating mechanism 927 relative to the guiding arm 957.

The locking arm 965 has a curved shape and is coupled with at least one of the operating mechanism 927 and the upper blade 920 and is further slidably engaged with the lower member 930 of the speculum. In certain embodiments, one end of the locking arm 965 is coupled to the operating mechanism 927. In other embodiments, the opposing end of the locking arm 965 is coupled to the upper blade 922 of the upper member. In yet other embodiments, the locking arm 965 is coupled with both the operating mechanism 927 and the upper blade 922. The slidable engagement of the locking arm 965 and the lower member 930 allows the locking arm 965 to slide relative to the point of engagement 965a, and upon completion of adjustment, to lock at the point of engagement. A locking mechanism provided at the point of engagement 965a may use one or more biasing members or may include locking protrusions or teeth or the like.

In operation, when a doctor presses down on an adjustment tab 928 of the operating mechanism 927, the operating mechanism 927 slides relative to the guiding arm 957 and causes the locking arm 965 to slide relative to the lower member at the point of attachment 965a. This operation causes the upper blade to move vertically relative to the lower blade and to also increase the angle between the upper and lower blades. As a result, a single operation by the doctor would result in both translational and angular adjustments of the upper blade relative to the lower blade. After making the adjustment, the locking mechanism at the point of engagement 965a locks the position of the locking arm 965, thereby preventing movement of the operating mechanism 927 relative to the guiding arm 957. Operation of the locking mechanism upon completion of adjustment may be automatic or may require an additional action by the doctor.

Figures 13A, 13B:
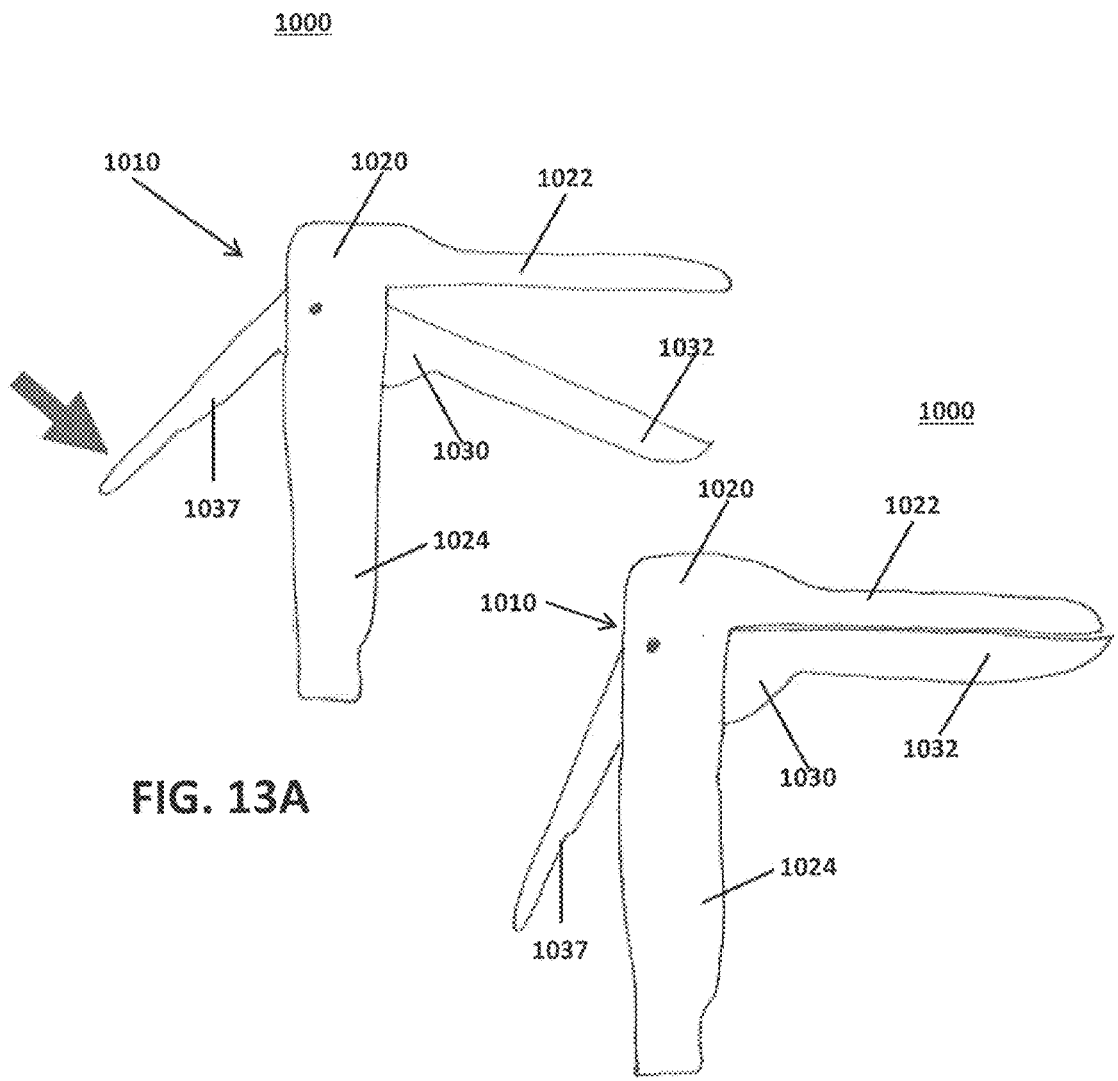
FIGS. 13A-13B show a speculum with a seventh embodiment of an angular adjustment mechanism.

FIGS. 13A and 13B show another angular adjustment mechanism 1010 which is operated silently. In FIG. 13A, the speculum 1000 is in an open position, while in FIG. 12B, the speculum 1000 is in a closed position. In the illustrative embodiment of FIGS. 13A and 13B, the speculum 1000 includes an upper member 1020, which includes an upper blade 1022 and a handle 1024, and a lower member 1030 which includes a lower blade 1032 and an operating mechanism 1037 extending from a proximal end of the lower blade 1032. The lower member 1030 is pivotably engaged with the upper member 1020. In certain embodiments, the pivotal engagement between the lower and upper members 1030, 1020 is near the proximal end of the handle and near the proximal end of the operating mechanism. The position of the pivotal engagement may be adjusted depending on the shape and configuration of the upper and lower members.

In FIGS. 13A and 13B, a biasing member, such as a spring, is used to force the upper and lower blades 1022, 1032 in an open position. Therefore, a force is required to be applied in order to close the blades by moving the lower blade 1032 in a closed position. During operation, a doctor would push or squeeze the operating member toward the handle so as to lift the lower blade 1032 and to close the lower blade. After the speculum 1000 is inserted vaginally, the doctor would release the operating member causing the lower blade 1032 to open relative to the upper blade 1034 by the biasing force of the biasing member. Since the angle is not adjustable due to the biasing member having one load, speculums with different biasing members having different loads may be provided. In addition, although not shown, a translational adjustment mechanism, as described herein above, may be provided in the speculum of this embodiment.

Figure 14:
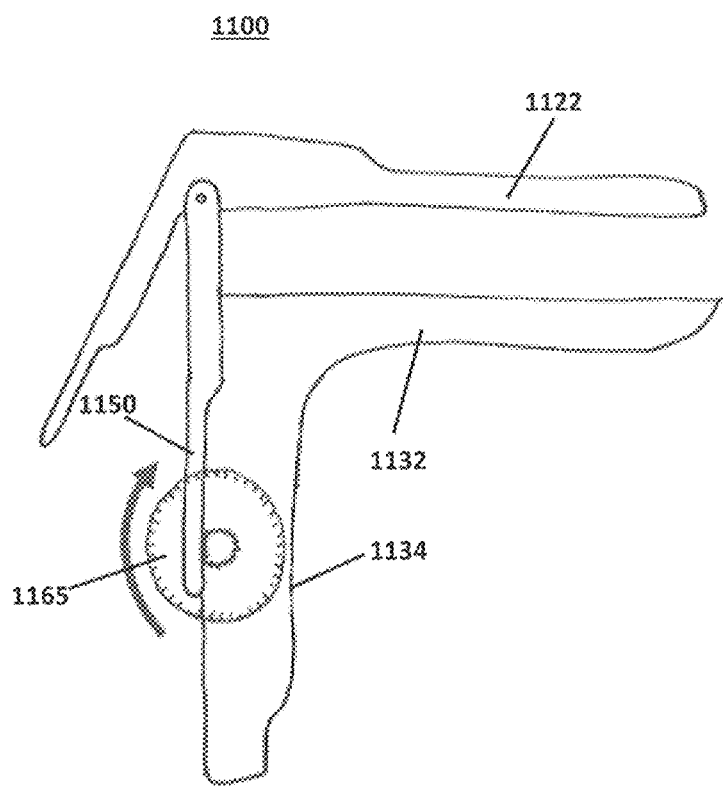
FIG. 14 shows a speculum with a third embodiment of a vertical adjustment mechanism.

FIG. 14 shows an alternative mechanism for translational adjustment. Instead of using a lock tooth on the linear support member and stop tabs on the handle, a gear 1165, or pinion, is provided on the handle 1134 of the speculum for engagement with the linear support member 1150. The linear support member 1150 includes a toothed surface (not visible) that forms a rack for engaging with the gear 1165. Since the linear support member 1150 is slidably engaged with the handle 1134, rotational force applied to the gear 1165 causes the linear support member 1150 to move vertically relative to the handle 1134. During operation, a doctor would spin the gear using his or her thumb so as to adjust the vertical position of the upper blade 1122 relative to the lower blade 1132.

The gear 1165 may be a self-locking gear that automatically locks the position of the linear support member 1150 relative to the handle, thus locking the vertical position of the upper blade relative to the lower blade. Alternatively, a lock may be provided for locking the gear 1165 in position after adjustment. In addition, a release mechanism to allow reverse translational adjustment may be provided to allow the doctor to release the translational adjustment and to lower the upper blade relative to the lower blade.

Although the gear and rack mechanism in FIG. 14 is employed in the translational adjustment mechanism of the speculum, this mechanism may also be adapted for use in the angular adjustment mechanism. In such case, the translational mechanism may either be the gear and rack mechanism of FIG. 14 or the mechanisms shown in FIGS. 3A and 3B or FIGS. 7A-7C.

In the above-described embodiments, the adjustment mechanisms are silent and click-free during adjustment and are easy to use. In addition, the adjustment mechanisms are suitable for use in disposable one-time use specula, and all or most of the parts of the specula are formed from plastics and/or polymer materials. As mentioned above, glass fibers may be added to plastic and/or polymer materials in order to increase their strength and rigidity.

Battery Removal for Illuminated Specula

All of the above-described embodiments may be used in illuminated specula, which include an illumination assembly for providing illumination during examination. Examples of illumination assemblies and specula with illumination assemblies are described in U.S. Pat. No. 9,307,897 and application Ser. No. 14/316,787 (US Pub. No. 2014/0309499) and Ser. No. 14/748,435 (US Pub. No. 2015/0289757), all of which are incorporated herein by reference.

As mentioned above, the illumination assembly of a cordless disposable speculum uses batteries, and it is preferable to separately dispose of or recycle these batteries. Conventional illumination assemblies do not provide for safe removal of the batteries from the speculum. As shown in FIGS. 15-28 and described below, the present invention contemplates several embodiments of battery removal mechanisms, which can be used in illuminated specula with the adjustment mechanisms described above.

Figure 15:
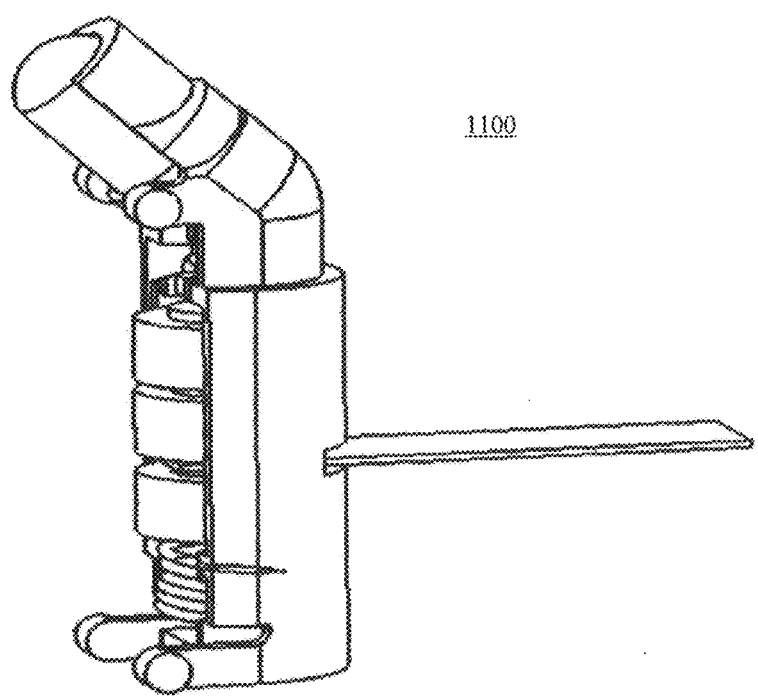
FIG. 15 shows a conventional illumination assembly for use with a disposable speculum.

In accordance with various embodiments of the present invention as set forth herein, an illumination assembly is defined by a structure (e.g., a housing or a casing) that retains at least a light source and a power supply. The illumination assembly in some instances may further contain one or more conducting/non-conducting circuit elements, one or more energization/de-energization switch elements, engagement/retention elements, etc. FIG. 15 shows an exemplary prior art illumination assembly. Further structural and operational details regarding these types of illumination assemblies are described in at least U.S. patent application Ser. No. 14/316,787 (US Pub. No. 2014/0309499) and Ser. No. 15/178,744 (US Pub. No. 2016/0310121), both of which are incorporated herein by reference in their entireties.

As shown in FIG. 15, the housing that defines the illumination assembly is a semi-enclosed (or partially enclosing) structure having at least one open side allowing access to or removal of its constituents. For example, the illumination assembly is configured to fully retain and securely hold the batteries and the contained light source upon placement of the illumination assembly onto a surface of a blade. Typically, the surface upon which the illumination assembly is placed (e.g., the speculum blade) provides the final, missing support for a full and complete retention.

As further shown in FIG. 15, the illumination assembly is configured to attach to a speculum blade via suitable engagement means (e.g., clips, adhesives, slots and tabs, etc.). The position of attachment of the illumination assembly along the blade varies from anywhere between a distal end of the blade and a proximal end of the blade, or within or extending along a curved portion (transition into handle portion) of the blade. In some prior art devices, the illumination assembly is contained entirely within the handle portion of the speculum and the light is directed to a desired area, e.g., the distal end of the speculum blade, via use of light guiding means such as a light pipe. In other prior art devices, at least of a portion of the illumination assembly is external to the device or positioned on an exterior surface thereof, e.g., on the exterior surface of the speculum blade.

The various embodiments of the present invention incorporate a similar illumination assembly but are not necessarily limited to use of the illumination assembly as shown in FIG. 15. In particular, the embodiments of the present invention as described herein, as well as their respective variants, are compatible with illuminating means of any size, shape or structure. Furthermore, although the embodiments described below are used in a speculum, it is also contemplated that the embodiments of the present invention are applicable to any medical or surgical device in which one or more of the entire medical or surgical device, the illuminating means, or the batteries are configured to be discarded after use.

Referring now to an exemplary embodiment of the present invention, a speculum apparatus having at least one blade and at least one an illumination assembly is provided, the illumination assembly being attached to the blade or handle and further having a bottomless battery compartment. The phrase "bottomless battery compartment" as used herein refers to a compartment within an illumination assembly for retaining one or more batteries in which the compartment does not completely permanently enclose the retained batteries. It is understood that the embodiments described below may be adapted for use with other medical and surgical devices, including but not limited to laryngoscopes, anoscopes, suction devices, electrocautery devices, and any other medical or surgical devices which use portable power sources, such as batteries or power packs.

As shown in FIG. 16A, a speculum apparatus 1200 comprises a blade 1210, a handle, and an illumination assembly 1220 attached to the blade 1210. Only the lower member of the speculum is shown in the figures. In this embodiment, the illumination assembly 1220 includes a bottomless battery compartment that retains one or more batteries 1230. As described herein, the bottomless battery compartment does not provide any retaining support for the batteries along at least one of its sides, e.g., the bottom side of the compartment that comes in contact with the surface of the blade 1210.

In one version, the illumination assembly 1220 is a self-contained and standalone illumination assembly in which all of the batteries are at least loosely retained within the battery compartment by a small force (e.g., adhesive, spring, electromagnetic, etc.). In this version, a small outside force (e.g., shake, turbulence, push, jerk, etc.) applied to the illumination assembly or the apparatus causes the batteries to break loose via the open side of the battery compartment. In another version, the illumination assembly 1220 firmly retains the batteries within the battery compartment and requires a force exceeding a certain threshold to cause the batteries to break loose via the open side of the battery compartment.

In accordance with this embodiment, the blade 1210 comprises an opening 1240 that is aligned with the attachment position of the illumination assembly 1220. The opening 1240 of the blade 1210 is typically defined by a size or a hole that is sufficiently large to allow at least the batteries 1230 contained in the battery compartment to pass through and to be disposed. In one version, the opening 1240 may permit the entire illumination assembly to pass through and be disposed.

In accordance with this embodiment, the blade 1210 further comprises a cover 1250. The cover 1250 is typically provided on the external surface of the blade and covers the opening 1240. As shown in FIG. 16B, during a normal use of the apparatus 1200, the opening 1240 is sealed by the cover 1250. The cover 1250 in this state may be referred to herein as the "closed" position.

In one version, the cover 1250 is provided via an adhesive that allows the cover 1250 to be peeled off when disposal of the batteries is desired. For example, the cover 1250 is a sticker that is placed over the opening 1240 to secure the batteries 1230 against its surface. The sticker may be coated so that the batteries 1230 do not stick thereto but the sticker can be adhesively secured to the blade 1210. In another version, the cover 1250 is made of plastic material (e.g., same or similar substance as the blade). The plastic cover may be attached to the blade 1210 via adhesives, hinges, latches, clips, rails, screws, snaps or using other suitable techniques. The plastic cover may be articulated from the closed position to an "open" position by, for example, pressing onto the plastic cover, sliding the plastic cover, peeling the plastic cover, turning or rotating the plastic cover, etc. In some versions, a button may be used for releasing the cover when pressed. In a further version, the cover 1250 is formed as part of the blade 1210 itself. For example, the cover 1250 is a hinged door that opens/closes the opening 1240 or a slide door that exposes the opening 1240 for battery disposal. FIG. 16C shows an example of the cover 1250 in its "open" position.

As variations to one or more of the versions of this embodiment, the illumination assembly 1220, the opening 1240 and the cover 1250 may be positioned at the distal (front) end of the blade 1210, the center of the blade 1210, the proximal (rear) end of the blade 1210, or within the handle, or extends along two or more of these portions of the blade. Regardless of position, the operation of the illumination assembly with respect to the opening and the cover remains the same or substantially similar.

In accordance with this embodiment of the present invention, once the cover 1250 is either removed, peeled, or otherwise in the open position, the user can apply a force, such as shaking, pressing or bumping the apparatus, to "pop" the batteries 1230 out from their retained position. Upon such force, the batteries 1230 and/or the illumination assembly 1220 can be detached from the blade 1210 or the handle and can be disposed separately and safely from the rest of the apparatus 1200. In certain versions, no force is necessary to remove the battery(ies) and, in such versions, the batteries fall out when the cover 1250 is removed, peeled or otherwise in the open position. In yet other versions, a ribbon or the like may be passed behind the batteries and when the cover is removed, the ribbon can be pulled to dislodge and release the batteries.

Another embodiment of the present invention is provided with reference to FIGS. 17A-17D. In this embodiment, a speculum apparatus 1300 includes a blade 1310, an illumination assembly 1320 with one or more batteries 1330, an opening 1340 and a battery compartment 1350 for holding the one or more batteries. Again, only the lower member of the speculum is shown for ease of understanding. The structure and operation of the apparatus and the illumination assembly are the same as those described in reference to FIG. 16A, and thus, further description thereof will be omitted. It is understood that although FIGS. 17A-17D show the illumination assembly 1320 being disposed in the proximal end of the blade or in the area that joins the blade to the handle, in other embodiments, the illumination assembly may be provided in other areas of the blade, e.g., closer to the distal end, or in the handle portion of the apparatus in combination with a light guide or a similar device.

In accordance with this embodiment, the battery compartment 1350 houses the one or more batteries used in the illumination assembly and is inserted into the opening 1340 in the apparatus 1300. The battery compartment 1350 includes an opening 1350a at one end which allows the batteries 1330 to be electrically coupled with a light source of the illumination assembly when the battery compartment 1350 is in a closed state, and allows for removal of the batteries when the battery compartment 1350 is in an open state. In the closed state, the battery compartment 1350 acts as a cover for the opening wherein the outer wall of the battery compartment 1350 is coextensive with the walls of the blade and/or handle.

Figure 17A:
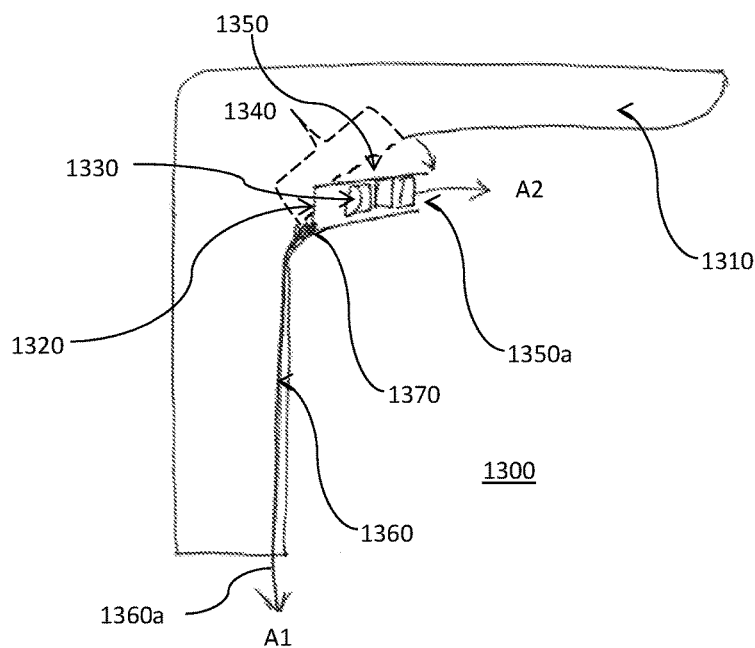
FIGS. 17A-17D show a medical device with a second embodiment of an illumination assembly of the present invention that allows for battery removal.
Figure 17B:
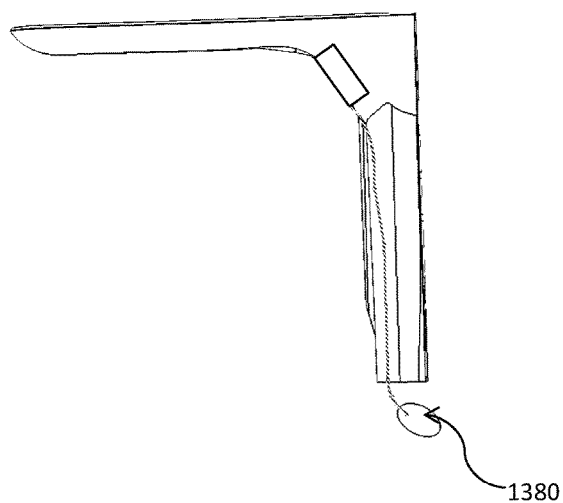
Figure 17C:
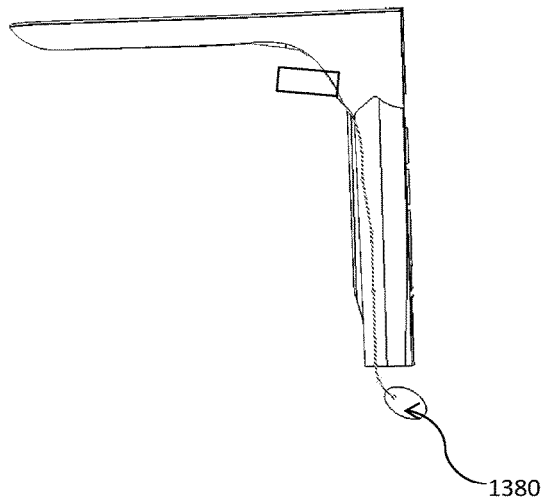

As shown in FIGS. 17A-17C, the battery compartment 1350 is articulated by operating a release mechanism that includes a release tab 1360 that can be moved from a first position in which the release tab 1360 holds the battery compartment 1350 in the closed state and a second position in which the release tab 1360 allows the battery compartment 1350 to drop down into an open state. In this illustrative embodiment, the release tab 1360 is engaged with the battery compartment 1350 at point 1370, but in other embodiments, the release tab 1360 may be engaged with the battery compartment 1350 at other points or other types of release mechanisms to move the battery compartment from the first position to the second position may be used.

As shown in FIGS. 17B and 17C, the release tab 1360 is coupled to a pull-down member 1380 via a connection line 1360a, which extends down through the handle portion of the apparatus. The pull-down member 1380 may be inserted into or engaged with the distal end of the handle so as to form a cap or the like which can be easily removed from the handle by the user and pulled down so as to move the release tab 1360 into the open state.

In operation, the user pulls on the pull-down member 1380 in the direction indicated by the arrow A1, causing the release tab 1360 to move from the first position to the second position so as to cause the battery compartment 1350 to articulate from its closed position to its open position and to cause the batteries 1330 to be disposed in the direction indicated by the arrow A2 through the opening 1350a in the battery compartment. In one version, the release tab 1360 opens a cover 1350 on the blade and only the batteries are disposed through the opening 1350a in the battery compartment. In another variation, the battery compartment may be replaced with an illumination assembly compartment holding the entire illumination assembly so that the entire illumination assembly can be disposed via the opening 1340 when the illumination assembly compartment is in the open state. In another variation, the pull-down member 1380 is connected directly to the battery compartment 1350 or the illumination assembly compartment, and when the pull-down member 1380 is pulled, the battery compartment or the illumination assembly compartment is disengaged from the closed state and the batteries or the whole illumination assembly is disposed.

FIG. 17B shows an example of a pull-down member prior to activation and FIG. 17C shows an example of the pull-down member after activation in which the battery compartment is pushed through the opening of the blade. As shown, the pull-down member may be freely hanging from the handle in some embodiments, while in other embodiments, the pull-down member may be engaged with the distal end of the cap to form an end cap or the like that is removable from the handle. In yet other embodiments, the pull-down member may be replaced by another activation mechanism, such as a switch or a pull-tab provided on the handle of the apparatus. In yet further embodiments, the activation mechanism may be disposed within the interior of the handle and is engaged or otherwise activated by placing a tool or a finger inside the handle from its open end. For example, a switch, a button, a pull-tab, a pull-down member or any other suitable mechanism may be provided on the interior of the handle or on the interior wall of the handle. In such embodiments, the activation mechanism cannot be accidentally triggered.

In the embodiment described above with respect to FIGS. 16A-16C, the battery removal mechanism uses a battery compartment or an illumination assembly compartment which is articulated between the closed position and the open position so as to release the batteries and/or the illumination assembly from the apparatus for disposal. In other embodiments, the battery removal mechanism may use a cover for covering the opening 1340 and for articulating between the first position in which the cover is closed and the batteries and/or illumination assembly are retained in the apparatus and the second position in which the cover is open and the batteries and/or illumination assembly can be removed from the apparatus through the opening 1340 and disposed. The same or substantially similar release mechanism is used for causing the cover to articulate between the first and second positions. In these embodiments, the batteries may be housed within a separately formed battery compartment so that when the cover is opened, the entire battery compartment with the batteries is removed. In other variations, the whole illumination assembly is housed within an illumination assembly compartment so that when the cover is opened, the illumination assembly compartment is removed, thus disposing of the entire illumination assembly. In yet other variations, the batteries are held in a partially open battery or illumination assembly compartment or case, which has an opening coextensive with the cover, so that when the cover is opened, the batteries drop down from the partially open compartment and can be disposed.

Figure 17D:
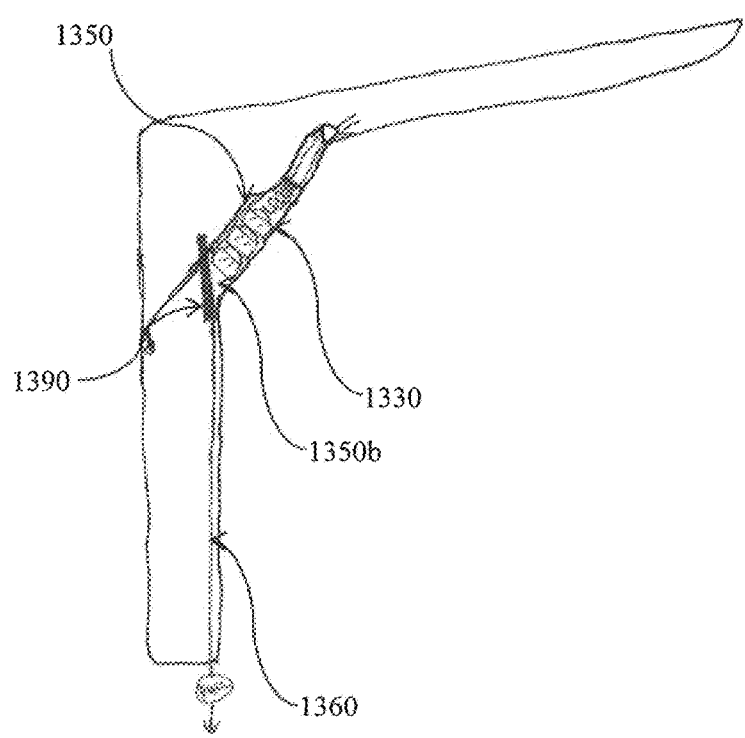

A further variation of this embodiment is shown in FIG. 17D. In this version, the battery compartment 1350 includes one or more batteries 1330 and an opening 1350b that opens into the handle portion of the apparatus. Specifically, in this version, the battery compartment 1350 is further configured with a closing tab (or a "door") 1390 that holds the batteries 1330 within the battery compartment 1350, when the closing tab 1390 is in a closed state. As shown in FIG. 17D, the batteries 1330 rest on the closing tab 1390 in the closed state. In the illustrated example of FIG. 17D, the batteries are disposed in the area that connects the blade to the handle portion on an angle relative to the blade and to the handle portion. However, in other variations, the batteries may be disposed in other areas of the apparatus, such as within the handle or in the blade area and the orientation of the batteries may be varied depending on the construction of the illumination assembly. For example, the battery compartment may be provided in the handle portion in a substantially vertical orientation so that the batteries are supported by the closing tab 390 in the closed state.

In FIG. 17D, for disposal of the batteries, the closing tab 1390 is actuated from its closed state to an open state by pulling on the release tab 1360. For example, the user can pull on the release tab 1360 that hangs loose through the handle portion causing the closing tab 1390 to detach from the battery compartment 1350, allowing the batteries 1330 to drop down through the handle portion of the speculum. In one version, the entire closing tab 1390 is detached. In this version, the closing tab, once detached, is also dropped through the handle portion. In another version, the detachment of the closing tab 1390 is only partial. In this version, pulling of the release tab 1360 partially breaks the attachment of the closing tab 1390 to the battery compartment 1350 and allows the closing tab 1390 to remain partially attached to the battery compartment 1350 (e.g., swinging via a hinge) to release the batteries via the handle portion. In yet other versions, the closing tab may be hingedly, rotatably or slidably connected to the battery compartment 1350 or to the handle portion and may be held in the closed state until the release tab 1360 is pulled. In certain variations, a spring member may force the closing tab 1390 into the closed state, while in other variations, the closing tab 1390 may be mechanically coupled with the battery compartment 1350. Pulling of the release tab 1360 in these versions would cause the closing tab 1390 to rotate or to slide relative to the opening in the battery compartment into the open state so that the batteries can be dropped into and through the handle portion.

Figure 18:
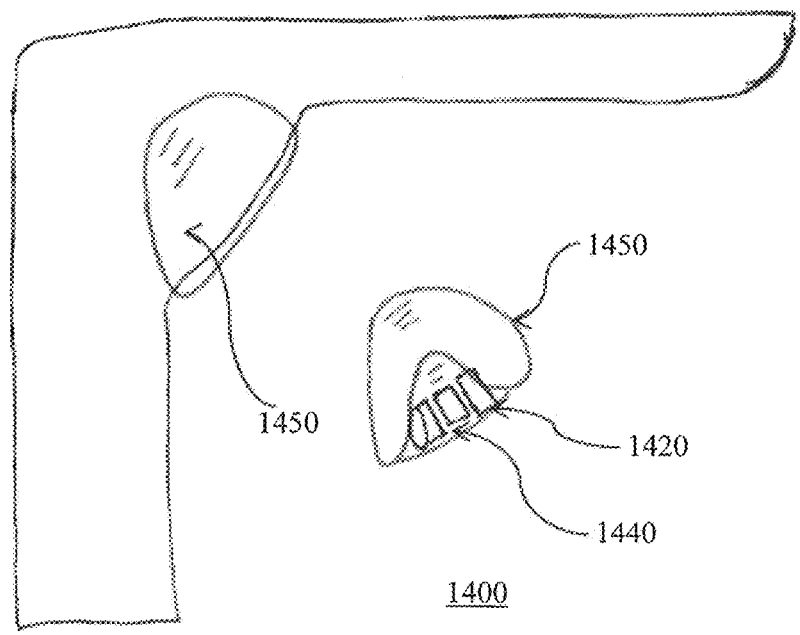
FIG. 18 shows a medical device with a third embodiment of a portion of an illumination assembly of the present invention that allows for battery removal.

A further embodiment of the present invention is shown in FIG. 18. In this embodiment, a speculum apparatus 1400, similar to those described in reference to FIG. 16A, includes similar components such as the blade, the illumination assembly with one or more batteries, an opening formed in the blade or handle, and a cover for the opening. In this embodiment, the illumination assembly 1420 may include a bottomless battery compartment with an opening that corresponds to the opening in the blade or handle. Alternatively, the illumination assembly 1420 may be a self-contained illumination assembly with a housing that partially houses the illumination assembly and in which the one or more batteries are at least loosely retained by the housing by a small force. In such variation, an opening in the housing for the illumination assembly corresponds at least in part with the opening in the blade or handle.

As shown in FIG. 18, the opening in the blade or handle is covered by the cover 1450 which may be formed from a plastic, polymer or rubber material. The cover 1450 is releasably attachable to the handle or blade or the apparatus. Any suitable fastening or attachment mechanism may be used for releasably attaching the cover to the handle or blade of the apparatus, including but not limited to providing protrusions and corresponding recesses or slots on the cover and handle or blade, using an adhesive to attach the cover to the handle or blade, or any suitable fastener. The cover 1450 may be completely removable from the handle or blade of the apparatus or in certain embodiments, the cover 1450 may be hingedly connected to the handle or blade so as to open and close relative to the blade or handle. In yet other embodiments, the cover 1450 may be elastic and squeezable, so that the cover is fitted into the opening in the handle or blade of the apparatus and can be removed by squeezing the cover on the sides to detach it from the opening.

During operation of the apparatus, the cover 1450 covers at least the one or more batteries and retains them in the illumination assembly 1420. After the operation is completed and before disposing the apparatus, the cover 1450 is removed to expose the batteries, and the batteries can then be removed by a small outside force such as a shake, or a jerk, applied to the apparatus. In certain embodiments, the cover 1450 forms an elastic and squeezable layer around a portion of the batteries so that the cover 1450 is depressible or squeezable by the user for releasing the contained batteries. Specifically, pressing on the sides of the squeezable cover 1450 forces the batteries to be released through the opening 1440 and to be removed simultaneously with the cover 1450. The user can then dispose the batteries while holding the cover over the recycling container for the batteries. In another variation, the cover has to be articulated by sliding, rotating or the like so as to cause the batteries to be released and removed together with the cover.

In another exemplary embodiment of the present invention, a speculum apparatus, is provided in which one or more batteries for powering a light source are provided within the handle portion thereof. It is understood that this embodiment may also be applied to another medical device apparatus, such as a retractor, laryngoscope, anoscope, suction device, or the like. In accordance with this embodiment, the illumination assembly is structured such that the batteries for powering the light source are retained in the handle portion and the light source is positioned along the blade or some other component of the apparatus where illumination is needed. The batteries are connected to the light source using wires. In some versions, the illumination assembly is structured such that the batteries and the light source are both retained in the handle portion and the light is directed to the area where illumination is needed, e.g., the distal end of the blade, using a light directing means (e.g., a light pipe, prism, mirrors, etc.).

Figure 19:
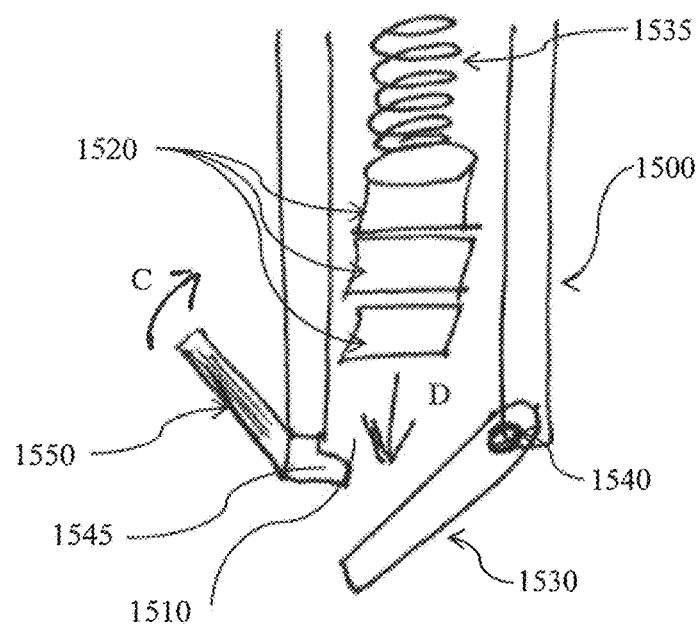
FIG. 19 shows a portion of a medical device with a fourth embodiment of a portion of an illumination assembly of the present invention that allows for battery removal.

Referring now to the battery removal aspect, the apparatus as shown in FIG. 19 includes a handle portion 1500 having an open-bottom receiving end 1510 for receiving and retaining one or more batteries 1520. In accordance with this embodiment, the open-bottom receiving end 1510 of the handle portion 1500 is covered by a platform 1530 that forms an end cap or end wall of the handle portion. The platform 1530 is hingedly (or rotatably) attached to the handle portion 1500 via a hinge 1540, and is locked in place by a tab 1545 and a release switch 1550. When the release switch 1550 is actuated in the direction indicated by the arrow C, the tab 1545 is moved away from a closed position and the platform 1530 drops down and rotates via the hinge 1540, which causes the batteries 1520 retained in the handle portion to be disposed in the direction indicated by arrow D. Although this illustrative embodiment uses a tab 1545 to hold the platform 1530 in a closed position and to release the platform 1530 into the open position, it is contemplated that other mechanisms may be used for retaining the platform 1530 in the closed state and for releasing the platform to allow it to drop down.

In this embodiment, it should be noted that the batteries 1520 are merely resting upon the platform 1530 when the platform is in its "closed" position and a biasing member, such as a spring, may be used to bias the batteries 1520 in a direction of the platform 1530. As shown in FIG. 19, the spring 1535 is provided above the batteries and pushes the batteries toward the platform 1530. As a result, when the release switch 1550 is actuated to open the platform 1530, the batteries are pushed out of the handle by the force of the spring 1535.

In one version, when the entire illumination assembly is positioned within the handle portion of the apparatus, all or a portion of the illumination assembly may be adhesively or mechanically attached to the handle portion. However, the batteries may be held by a bottomless battery compartment with an opening at the bottom covered by the platform 1530, or as shown in FIG. 19, the handle portion may form the bottomless battery compartment that houses the batteries. In either case, when the platform 1530 is opened, the batteries can drop down through the open-bottom receiving end 1510 of the handle portion.

In another version, the light source of the illumination assembly is attached to the blade portion or some other portion of the apparatus where illumination is needed, and the batteries are retained in the handle portion of the apparatus, either in a separate bottomless compartment or in the handle portion itself forming the bottomless battery compartment that houses the batteries. In this version, the batteries may be held in place within the handle portion or within the separate bottomless compartment using a biasing member, an adhesive or some other retention force, but application of an external force to the apparatus causes the batteries to drop out when the platform 1530 is opened. As a variation to this version, the apparatus may further comprise one or more buttons or a separate switch that causes the batteries to drop loose.

As a variation to this embodiment, the apparatus shown in FIG. 20A comprises similar components as the apparatus shown in FIG. 19, but further comprises a pull switch 1650 in place of the tab 1545 and the release switch 1550 as described with reference to FIG. 19. In one version, the handle portion 1600 includes one or more slots or holes near its open-bottom receiving end 1610 through which the pull switch 1650 passes. The pull switch 1650, in its "closed" (or inserted) position, attaches to or otherwise secures to the platform 1630. Although FIG. 20A shows the pull switch 1650 holding the platform 1630 at the top and bottom, in other variations, the pull switch 1650 may hold only the bottom of the platform 1630. In yet other variations, the pull switch 1650 may be inserted into a corresponding opening in the platform 1630 side edge so as to hold it in the closed position, as shown in FIG. 20C. Any other type of engagement between the pull switch 1650 and the platform 1630 may be used to releasably engage the pull switch 1650 with the platform 1630 in the closed state. Moreover, a biasing member, such as a spring member, may be used with the pull switch 1650 to bias the pull switch 1650 in the direction of the closed position. In this way, a predetermined pulling force on the pull switch 1650 would be needed in order to disengage the pull switch 1650 from the platform 1630 so as to prevent accidental opening of the platform 1630.

When the pull switch 1650 is articulated (in direction indicated by arrow E) to its "open" (or pulled) position, the pull switch 1650 separates from the platform 1630 and the platform 1630 drops down and rotates via the hinge 1640. The batteries are disposed in the handle portion in the same manner as discussed herein in reference to FIG. 19 above, and thus, separate discussion thereof is omitted. FIGS. 20B-20C show different perspective views of the apparatus as shown and described in FIG. 20A.

Figure 20D:
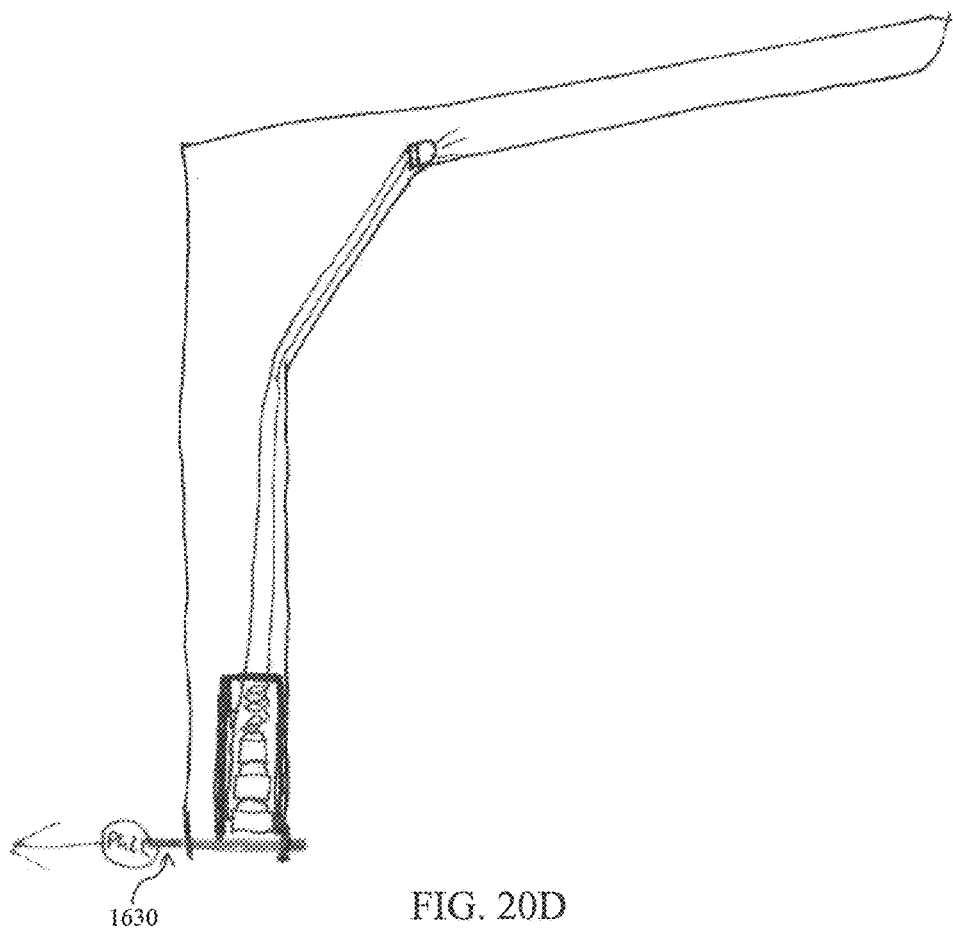

As a further variation of this embodiment, the entire platform 1630 may pass through slots formed in opposing walls of the handle portion. As shown in FIG. 20D, the platform 1630, having a length that traverses the entire width of the handle portion and provides a resting surface for the batteries, is provided in place of the platform-and-the-pull-switch combination shown in FIG. 20A. In this version, corresponding slots are provided in opposing walls of the lower end of the handle portion allowing the platform to be pulled in either direction. In an alternative configuration, the platform may be pulled only in one direction and may be prevented from being pulled in the other direction, e.g., by a flange or the like. Similar to the foregoing versions, once the platform 1630 is removed, the batteries drop through the open end of the handle portion.

As further variations to embodiments as described in reference to FIGS. 19 and 20, the platform may be articulated from its closed position to open position via different methods. For example, the release switch may be an external push button that releases the platform. For instance, a variation that includes a battery holding compartment with a pivotable platform is shown in FIGS. 21A-21G. As shown in FIGS. 21A-21C, a battery holding compartment 1740 is used for housing the batteries therein and for coupling the batteries, e.g., using wires, to the light source or to any other component of the apparatus that requires power supply. As shown in FIG. 21D, the battery compartment 1740 is inserted into an open end at the bottom of the handle portion of the apparatus. Although FIGS. 21A-21C show a separate battery holding compartment 1740 for housing the batteries and for releasing the batteries from the apparatus, in other embodiments, the handle portion may be configured to house the batteries directly therein and a similar pivotable platform mechanism may be used at the bottom of the handle portion as the one shown in FIGS. 21A-21C.

As shown in FIGS. 21A-21C, a bottom end of the battery holding compartment 1740 is provided with an opening 1710, which may be circular in cross section or any other suitable shape, and a mating portion 1720, which in this illustrative example is shown as a protrusion. As more clearly shown in FIG. 21B, a pivotable platform 1730 is provided, with the pivotable platform 1730 having a pivoting end 1730*a* and a mating end 1730*b*. The pivoting end 1730*a* pivotably engages with the opening 1710 formed on the bottom end of the battery holding compartment 1740. The mating end 1730*b* engages with the mating portion 1720 in a closed state so as to lock the pivotable platform 1730 relative to the battery holding compartment 1740. In the illustrative embodiments shown in FIGS. 21B-21D, the mating portion 1720 of the battery holding compartment 1740 is formed as a protrusion extending outwardly from a sidewall of the battery holding compartment 1740. In such embodiments, the mating end 1730*b* of the pivotable platform 1730 includes a locking tooth 1732 that mates with the mating portion 1720 so as to lock the pivotable portion 1730 in the closed state, and further includes an operating tab 1734 which can be operated by a user to release the mating between the locking tooth 1732 and the mating portion 1720. When the operating tab 1734 is actuated by a user (e.g., by pressing), the lock between the locking tooth 1732 of the pivotable platform 1730 and the mating portion 1720 is released and the pivotable platform 1730 may be pivoted into the open state relative to a pivot point at the pivot end 1730*a*. In other illustrative embodiments, the mating portion 1720 may be formed as a recess so that the locking tooth 1732 of the mating end 1730*b* is inserted into the mating portion 1720 recess in the closed state. Other configurations of the mating portion 1720 and the mating end 1730*b* may be used for providing a locking mechanism for locking the pivotable platform 1730 to the battery holding compartment 1740.

As further shown in FIG. 21C, the pivotable platform 1730 in its "closed" position provides a surface on which one or more batteries rest within the battery holding compartment 1740. The batteries are electrically connected to a distantly positioned light source via electrical wires extending through the handle portion. For disposal of the speculum and/or the batteries, the pivotable platform 1730 is released from engagement with the mating portion 1720 via an external force applied to the operating tab 1734 at the mating end 1730*b*. The pivotable platform 1730 then pivots via the pivoting end 1730*a* and permits the batteries to drop through the open bottom of the speculum handle portion. As shown in FIGS. 21C-21D, a spring or another type of biasing member may be provided at the top of the batteries so as to bias the batteries in the direction of the opening in the battery holding compartment, i.e., in the direction of the pivotable platform 1730.

In the embodiment described above and shown in FIGS. 21B-21D, the pivotable platform 1730 is configured together with a battery holding compartment 1740 as a standalone structure. In such version, as shown in FIG. 21D, the battery holding compartment is sized and/or shaped such that it is insertable (or fittable) into the hollow end of the handle portion. In this version, the mating portion is included on the battery compartment 1740. When the standalone structure is received a certain length within the hollow end of the handle portion, the user can actuate, by operating the operating tab 1734, the mating end 1730*b* of the pivotable platform 1730 to pivot the platform to its open position.

FIGS. 21E-21G show respective bottom views of the foregoing examples of FIGS. 21B-21D. As shown in FIGS. 21E and 21G, the battery holding compartment 1740 includes openings or recesses 1710 in opposing walls thereof at the lower end. In FIG. 21E, the pivotable platform 1730 includes a pair of legs or shafts 1736 projecting from the sides of the platform at or near the pivoting end 1730*a*. The legs 1736 are inserted into the corresponding openings or recesses 1710 in the walls of the battery holding compartment 1740. In the illustrative example shown, the openings or recesses 1710 have a smaller cross-section than the thickness of the legs 1736 at an initial point of insertion, with the cross-section increasing to accommodate the thickness of the legs. In this configuration, the legs 1736 of the platform 1730 snap into the openings or recesses 1710, and can be prevented from disengaging from the openings or recesses 1710. As shown in FIG. 21E, the body of the platform may be narrower than the opening in the battery holding compartment 1740 as long as the platform 1730 can retain the batteries within the battery holding compartment 1740. In other variations, the body of the platform 1730 is the same width or wider than the opening in the battery holding compartment 1740.

Figure 22A:
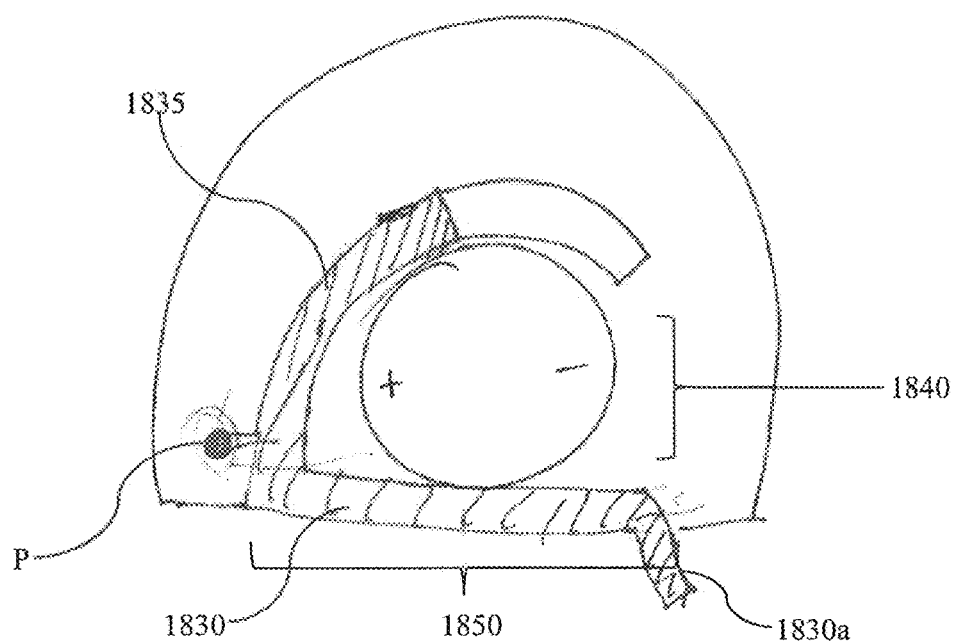
FIGS. 22A-22B show a portion of a medical device with a seventh embodiment of an illumination assembly portion of the present invention that allows for battery removal.
Figure 22B:
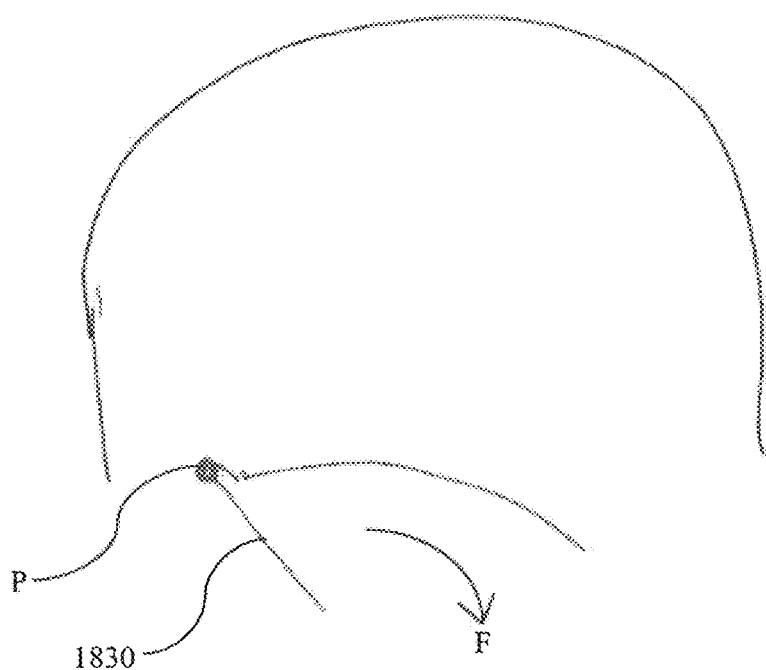

Another embodiment of a battery removal mechanism for removing and disposing batteries from a speculum or retractor apparatus is shown in FIGS. 22A-22B. FIGS. 22A-22B show a cross-sectional view looking axially down a handle portion having a battery ejection mechanism for removing batteries disposed within the handle portion through an opening 1850 formed in a sidewall of the handle portion. The ejection mechanism includes a door 1830 that covers the opening 1850 in the handle portion and includes with an ejection lever 1835 extending partially around the batteries housed within the handle portion. The door 1830 is pivotable around a pivot point P between a closed state, shown in FIG. 22A, and an open state shown in FIG. 22B. The door 1830 also includes an operation tab 1830*a* which can be operated (e.g., by pressing) by a user to open the door 1830 so as to move it from the closed state to the open state. When the door 1830 is opened, the ejection lever 1835, which moves together with the door 1830, pushes the batteries through the opening 1850 in the handle, thereby ejecting the batteries from the apparatus.

More specifically, as shown in FIG. 22A, the door 1830 is in its closed state. The door 1830 and the ejection lever 1835 are structured and/or shaped in a manner such that the one or more batteries can be released (or pulled) through an side opening 1840 formed between the door 1830 and the ejection lever 1835 using a small force or without using any force. In one version, the door 1830 and the ejection lever 1835 may be made of elastic material and the size of the side opening 1840 is smaller than the diameter of the retained batteries. In this version, a small force, such as a tap on the handle or a shake, would be required to release the batteries when the door 1830 is in the open state. In another version, the door 1830 and the ejection lever 1835 are made from plastic or polymer materials and the size of the side opening 1840 is the same or larger than the diameter of the batteries. In this version, no force is needed to release the batteries when the door is in the open state.

When the operation tab 1830*b* on the door is operated by a user, the door 1830 and the ejection lever 1835 rotate around the pivot point P, and as they rotate, the side opening 1840 formed between the door and the ejection lever is exposed through the side opening 1850 in the handle portion, and the batteries are pulled/pushed forward and out the opening 1850 in the handle portion. As discussed above, the batteries may be released through the side opening 1840 with no or little force. FIG. 22B illustrates the batteries being released in the direction indicated by arrow "F." As a variation to the embodiment shown in FIGS. 22A and 22B, a column-shaped structure (hereinafter "structure") with a hollow center and sidewalls for retaining and partially enclosing one or more batteries may be provided in the handle portion. The structure may have a platform for supporting the one or more batteries thereon, with the platform being connected to the sidewalls so as to be movable together with the rest of the structure. The structure is sized to be insertable and pivotable through the opening 1850 in the handle portion of the apparatus relative to the pivot point P. The cross-section of the sidewalls of the structure is substantially the same or similar to that of the door and ejection lever shown in FIG. 22A. Similar to the door and the ejection lever shown in FIG. 22A, the structure includes a circumferential sidewall that covers the opening 1850 in the handle portion of the apparatus and extends around the one or more batteries but does not completely encircle the batteries. For example, the circumferential sidewall includes an opening that allows the retained batteries to be released therethrough when the structure is rotated from the closed state to the open state. The rotation of the structure about the pivot point and the release mechanism for the batteries in the structure are similar to those described with respect to FIGS. 22A and 22B.

Further variations to the embodiments described in reference to FIGS. 19-22 are also contemplated. For example, the release switch shown in FIG. 20A may be an external push button that releases the platform. As another example, the platform shown in FIG. 20D may include further components that can be pushed or pulled to assist in articulation of the platform to its open position.

Figure 23A:
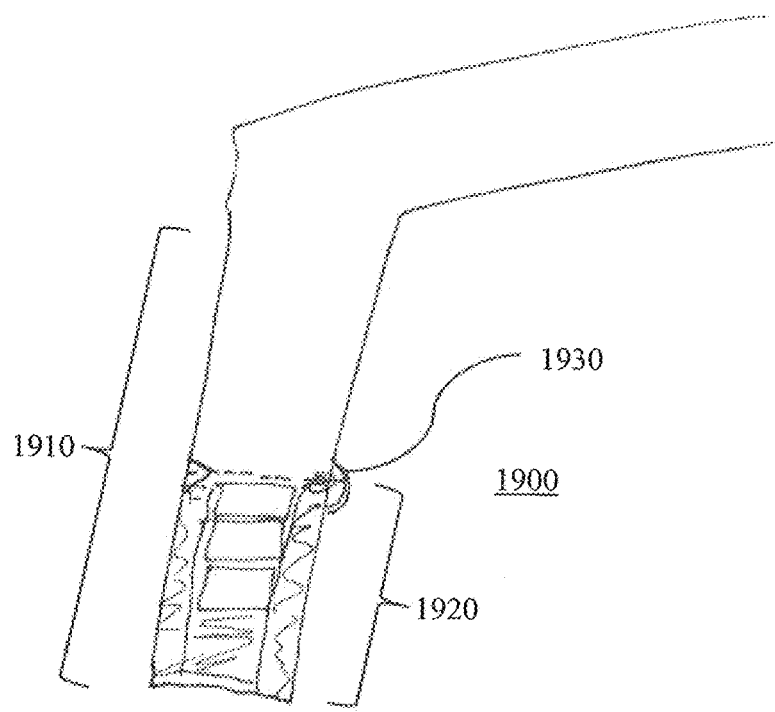
FIGS. 23A-23B show a portion of a medical device with an eighth embodiment of an illumination assembly portion of the present invention that allows for battery removal.
Figure 23B:
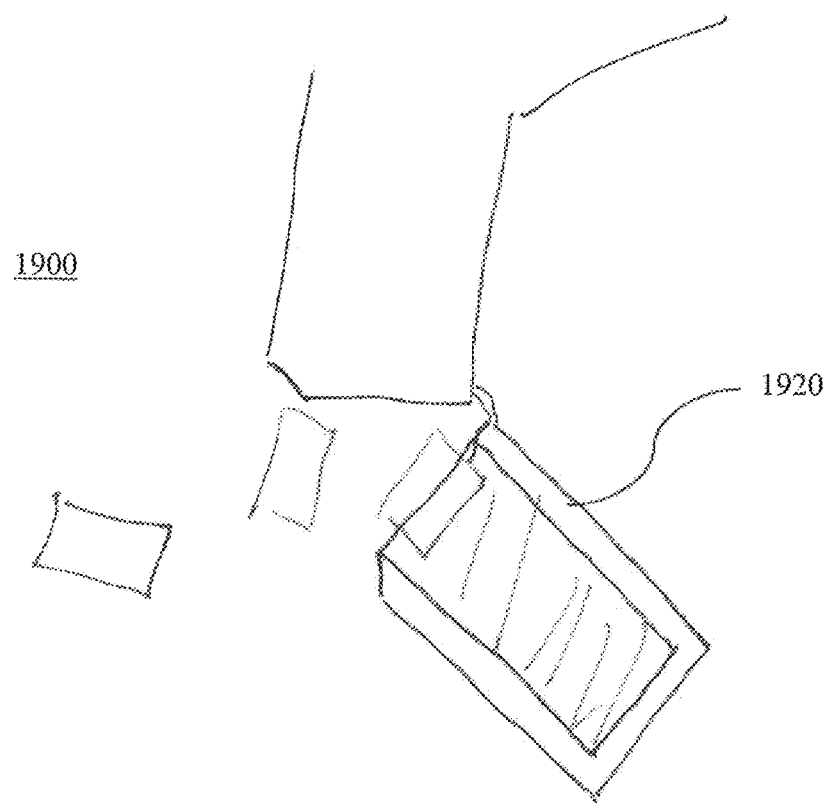

In yet another embodiment of the present invention, the handle portion of the apparatus is configured such that at least a portion thereof is breakable or detachable from the rest of the handle portion. As shown in FIG. 23A, the apparatus 1900 includes a handle portion 1910 in which a lower end portion 1920 is breakable or detachable from the remaining portion of the handle portion 1910. In accordance with this embodiment of the present invention, one or more batteries are retained within the lower end portion 1920 that is breakable or detachable from the rest of the handle portion 1910. In one embodiment, the breakable lower end portion 1920 completely detaches from the rest of the handle portion 1910. In another version, a hinge 1930 is provided between the breakable lower end portion 1920 and the rest of the handle portion 1910 such that when the breakable lower end portion 1920 is articulated to be "broken off" or detached from the handle portion 1910, the breakable lower end portion 1920 hinges via the hinge 1930 and the one or more batteries retained therein are released and can be disposed. FIG. 23B illustrates disposal of the batteries when the breakable lower end portion 1920 is separated from the rest of the handle portion of the apparatus and hinges via the hinge 1930. Actuation of the breakable lower end portion 1920 as described herein may be enabled using a variety of different methods such as manual force (pressing, twisting, pulling, etc.), a pull switch, a push button, or other similar techniques. The embodiments as described herein are intended to present a concept of separate disposal for batteries used in a medical device. In certain embodiments, a platform placed at the bottom end of the handle portion of the speculum apparatus or another medical device is opened in one of many different ways to allow the batteries to be disposed separately and quickly. In certain other embodiments, the blade or handle of the speculum or another apparatus includes an opening through which the batteries held in a bottomless battery compartment of an illumination assembly are disposed separately and quickly. In certain other embodiments, portions of the medical device that retains the batteries are detached completely or partially from the medical device itself. Separate disposal of batteries solves the problems of hazardous contamination and/or pollution of the environment. Furthermore, since the batteries are removed from the speculum at the time of disposal, users need not worry about throwing out lit up speculums in the trash.

FIGS. 24A-28G show another embodiment of a speculum 2000 which includes a battery removal mechanism which uses a battery compartment 2060 (also referred to as a "battery sled") provided in a handle 2034 of the speculum 2000. The battery compartment 2060 holds batteries 2074 within the handle 2034 in a retained state, which is the operating state of the speculum, and allowing the batteries 2074 to be released and disposed through an opening in a bottom of the handle in an ejected state.

Figures 24A, 24B:
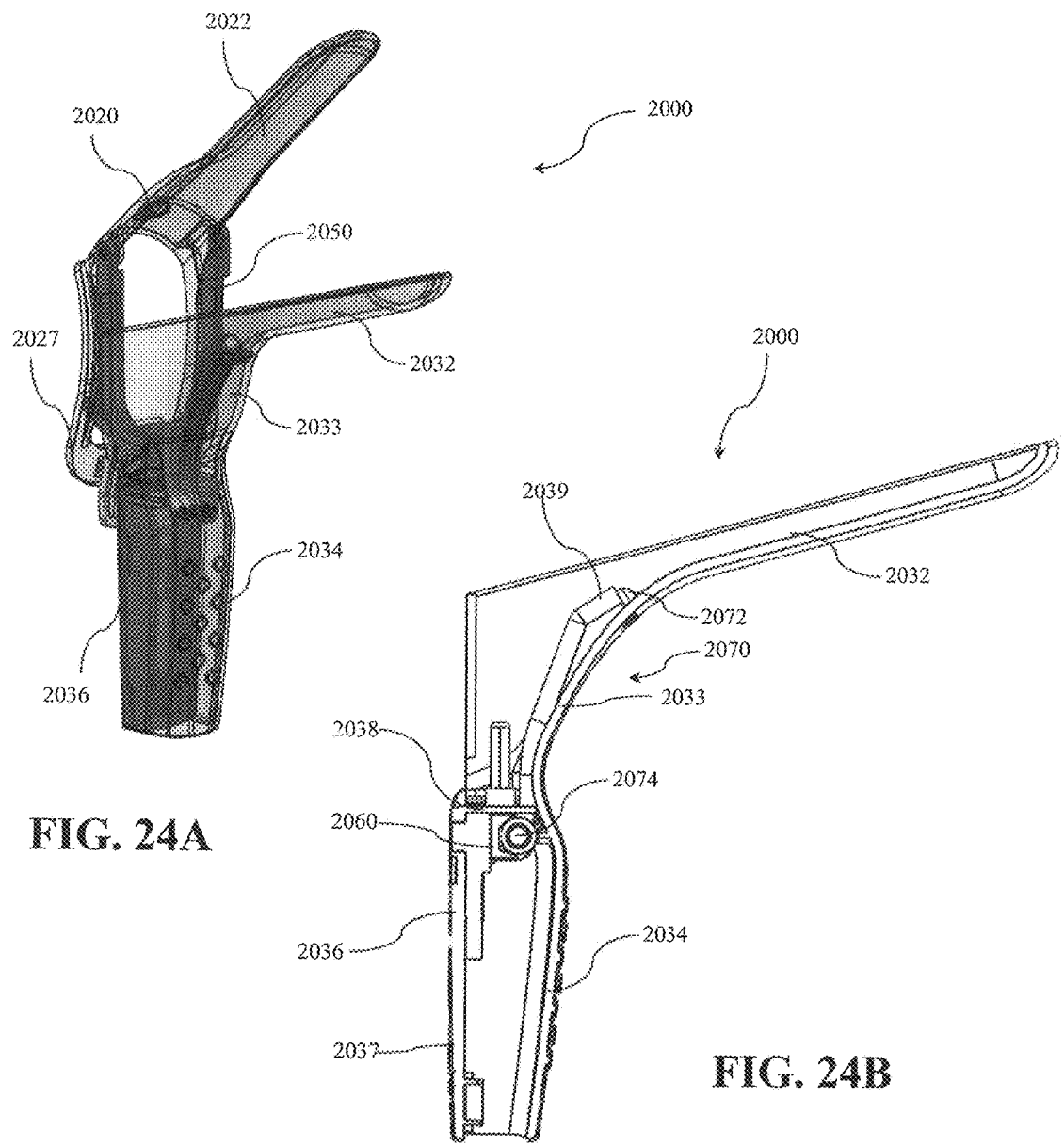
FIGS. 24A-24B show a speculum with a ninth embodiment of an illumination assembly of the present invention that allows for battery removal.

FIGS. 24A-24B show a general assembled configuration of the speculum 2000 of this embodiment. The speculum 2000 includes an upper member 2020 comprising an upper blade 2022 and an operating mechanism 2027, a lower member 2030 comprising a lower blade 2032, a handle 2034 and a rear faceplate assembly 2036 that engages with the handle 2034, and a linear support member 2050 which hingedly engages with the upper member 2020 for angular adjustment between the upper and lower blades, and slidably engages with the rear faceplate assembly 2036 for vertical adjustment between the upper and lower blades. The angular adjustment mechanism is substantially similar to that of FIGS. 4A-5G described herein above, and the vertical adjustment mechanism is shown in FIGS. 7A-7C and described herein above. The speculum 2000 includes an illumination assembly 2070 comprising at least one light source 2072, such as an LED or similar light emitting device, one or more batteries 2074 and wires (not shown) electrically connecting the light source 2072 with the one or more batteries. The illumination assembly may also include an activation device (not shown), which can be in a form of a pull tab, a button, a switch, a motion detector or the like, for activating the light source 2072 from on OFF state to an ON state and vice versa.

Figures 25A, 25B:
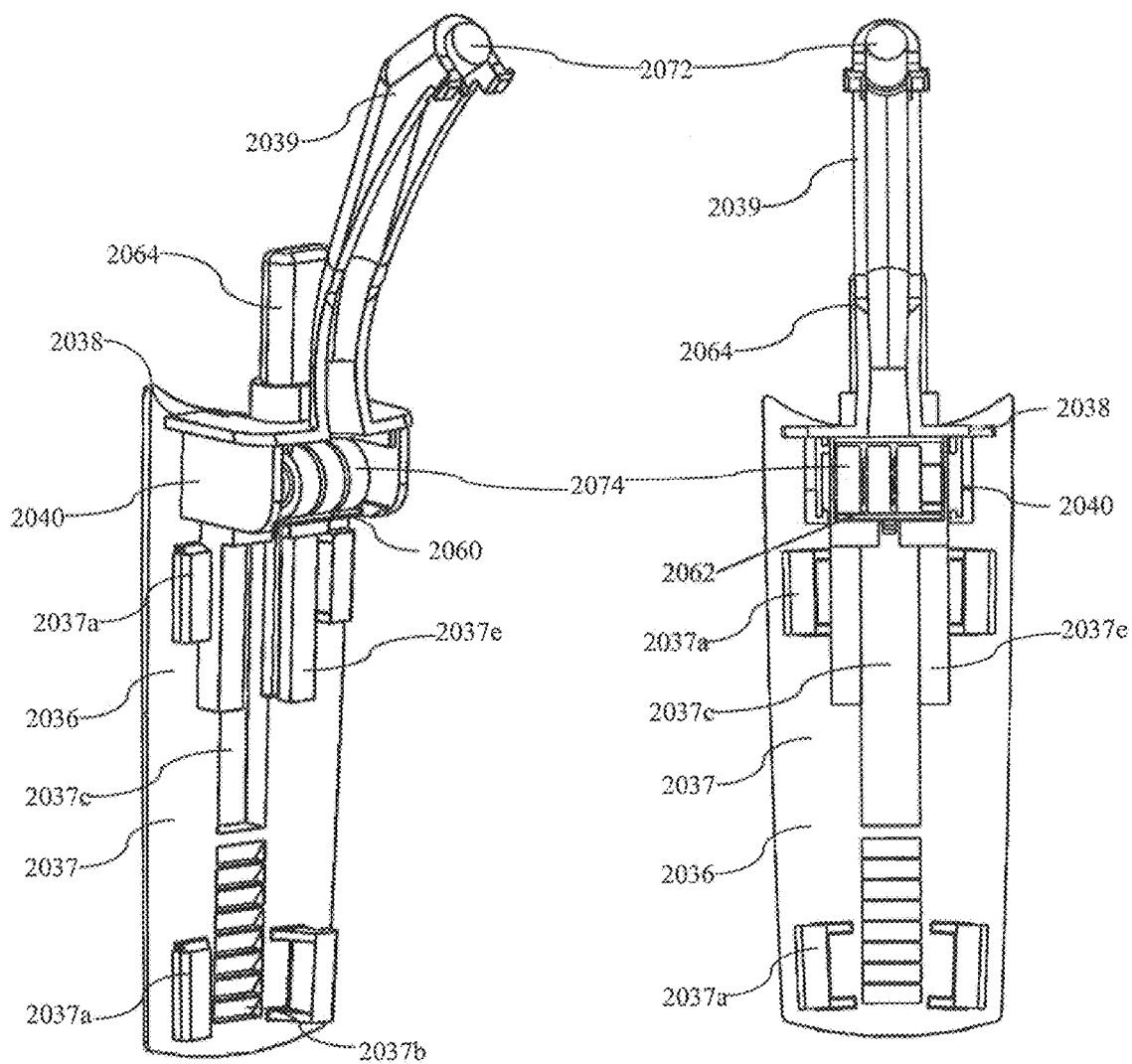
FIGS. 25A-25B show the ninth embodiment of the illumination assembly of FIGS. 24A-24B in more detail with a battery compartment in a retained state.

As shown in FIG. 24B and shown in more detail in FIGS. 25A and 25B, the rear face plate assembly 2036 includes a rear faceplate 2037 that engages with sidewalls of the handle 2034 and forms a rear wall of the handle 2034. The rear faceplate assembly 2036 also includes a shelf portion 2038 which extends from an upper end of the rear faceplate 2037 and an illumination assembly cover 2039 which extends from the shelf portion 2038. The illumination assembly cover 2039 extends along an inner surface of a front wall of the handle 2034 and along a curved portion 2033 that connects the handle and the lower blade 2032. The illumination assembly cover 2039 is open on the side that abuts the inner surface of the handle 2034 and the curved portion 2033, and encloses the wires connecting the batteries 2074 and the light source 2072. In this illustrative embodiment, the illumination assembly cover 2039 also partially encloses the light source 2072, which protrudes from an end of the illumination assembly cover 2039. In the present illustrative embodiment, the illumination assembly cover 2039 is engaged with the curved portion 2033 using tabs formed on the illumination assembly cover that engage with corresponding slots formed in the curved portion 2033. However, in other embodiments, the illumination assembly cover 2039 may engage with the handle 2034 and/or with the lower blade 2032.

In the embodiment shown in FIGS. 24A-24B, the illumination assembly 2070 is configured so that the light source 2072 is positioned adjacent the curved portion 2033 of the lower member. However, in other embodiments, the light source 2072 may be positioned closer to the lower blade 2032 or adjacent the lower blade 2032, at any location along the length of the lower blade 2032. In some embodiments, the illumination assembly cover 2039 may extend further than in the embodiments shown in FIGS. 24A-24B. For example, the illumination assembly cover 2039 may extend along a portion of the lower blade 2032. In some embodiments, the illumination assembly cover 2039 may also function as a smoke evacuation channel and may extend along the lower blade 2032 toward the distal end of the blade 2032.

FIGS. 25A-25D and 26A-26C show the rear faceplate assembly 2036 together with the battery compartment 2060 and the illumination assembly 2070. In FIGS. 25A-25D, the battery compartment 2060 is in the retained or operating state, while in FIGS. 26A-26C, the battery compartment is in the ejected state. In addition, FIG. 27 shows the rear face plate assembly 2036 without the battery compartment.

As shown in FIGS. 25A-25B, 26A and 27, the rear faceplate 2037 includes a plurality of engagement portions 2037a protruding from an inner surface thereof and configured to engage with corresponding protrusions formed on the inner side of the handle sidewalls. In certain embodiments, the protruding engagement portions 2037a may engage with a channel or one or more recesses formed in each of the handle sidewalls. In the illustrative embodiment of FIGS. 24-28, the vertical adjustment mechanism of FIGS. 7A-7C is used, and thus, the inner surface of the rear faceplate 2037 includes a plurality of stop tabs 2037b for engagement with a lock tooth of the linear support member. In other embodiments, however, the vertical adjustment mechanism of FIGS. 3A-3B may be used, and in such embodiments, the rear faceplate 2037 would include a plurality of stop tabs on an opposing, outer surface thereof. As also shown in FIGS. 25A-25B, the rear faceplate 2037 includes a through recess 2037c extending along its length which is used for sliding the linear adjustment member therein so as to provide for vertical adjustment, as described above with respect to FIGS. 7A-7C. In the embodiments of FIGS. 24-28, the rear faceplate also includes rail portions 2037e protruding from the inner surface thereof and extending on each side of the through opening. The rail portions 2037e guide the linear support member 2050 when it is inserted into the through recess 2037c.

The battery compartment 2060 comprises a housing 2062 for holding the batteries 2074 in the retained state, and an operating member 2064, which can be operated by a user to cause the housing 2062 to move from the retained state to the ejected state. In the present illustrative embodiment, the operating member 2064 is a button protruding from the top surface of the housing. When the battery compartment 2060 is assembled with the rear faceplate assembly 2036, the operating member 2064 passes through an opening formed in the shelf 2038 of the rear faceplate assembly 2036. The shelf has a pair of sidewalls 2040 extending from a lower surface of the shelf and surrounding the batteries 2074 held by the battery compartment 2060 in the retained state. The sidewalls 2040, together with the housing 2062 of the battery compartment 2060 hold the batteries 2074 in place and prevent dislodgement of the batteries. One or both of the sidewalls 2040 may include coupling elements attached thereto for electrically coupling the batteries 2074 to the wires. In addition, one or more biasing members, e.g., a spring, may be used to hold the batteries 2074 in place between the sidewalls 2040.

Figure 25C:
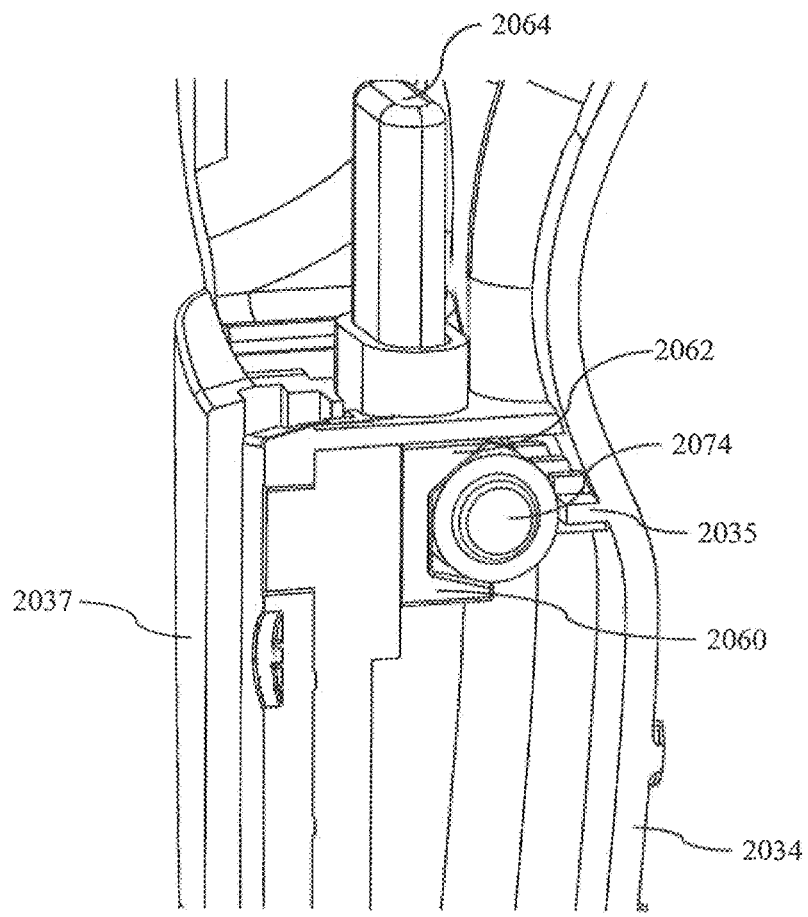
FIGS. 25C and 25D show cross-sectional view of the illumination assembly of FIGS. 25A-25B.
Figure 25D:
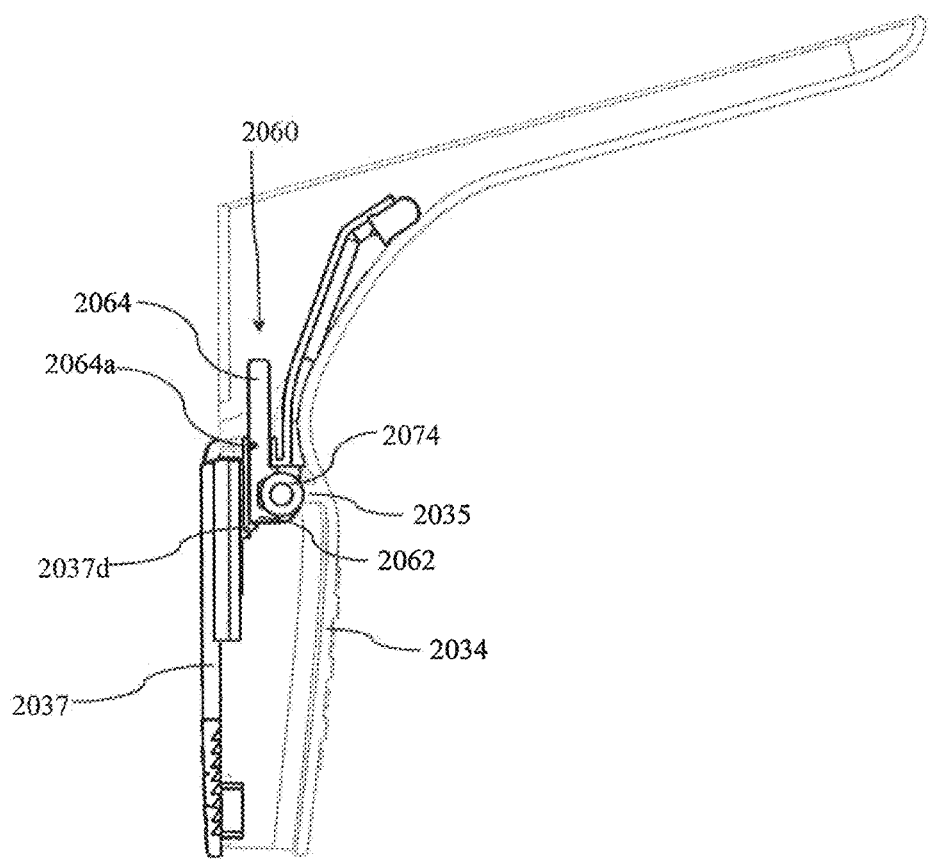

FIGS. 25C-25D show a cross-section of the speculum in which battery compartment 2060 is engaged with the rear face plate assembly 2036 in the retained state. As shown in the close-up view of FIG. 25C, the housing 2062 is a C-shaped housing which has an open side and holds the batteries 2074 against a projection 2035 formed on an inner front surface of the handle. Thus, in the retained state, the batteries 2074 are held in the C-shaped housing 2062 and are supported from the opposite side by the projection 2035 formed on the inner surface of the handle. Moreover, as described above, the batteries 2074 are also retained in their position by the sidewalls 2040 shown in FIGS. 25A-25B. The projection 2035 may be shaped as a beam with a plurality of ribs traversing the beam, as shown in FIGS. 25C and 26B. However, the shape of the projection 2035 may vary depending on the type of batteries used and the arrangement of the batteries in the housing 2062.

As shown in FIG. 25D, in the retained state, the battery compartment 2060 is locked in place relative to the rear face plate 2037 by a locking mechanism. In the illustrative embodiment shown in FIG. 25, the locking mechanism is a snap arm 2037d formed at a top portion of the rear faceplate 2037 which includes an arm having some flexibility/elasticity and a lock tooth which engages with the bottom surface of the battery compartment 2060. In this way, the top surface of the housing 2062 of the battery compartment prevents the battery compartment from moving in an upward direction relative to the rear faceplate 2037 and the snap arm 2037d prevent the battery compartment 2060 from moving in a downward direction relative to the rear faceplate 2037. Alternatively, a notch may be provided in the bottom portion of the battery compartment 2060 for engagement with the snap arm 2037d so as to prevent movement of the battery compartment. FIG. 27 shows a more detailed view of the snap arm 2037d, which is formed in the rear faceplate 2037 and extends into the through recess 2037c in the rear faceplate 2037. In some embodiments, instead of the snap arm or in addition to the snap arm, other mechanical engagements may be used to retain the battery compartment in the retained state and in the ejected state. For example, the button 2064 may include a lip formed at or near its top surface, with the periphery of the lip being greater than the opening in the shelf 2038. The lip would prevent the button 2064 from being pushed through the opening in the shelf 2038 past the lip and from falling out together with the batteries. Other types of retaining means may be used for preventing the battery compartment from falling out when the button is moved to the ejected state.

As also shown in FIG. 25D, the operating member 2064 includes a notch 2064a or a recess in its surface that faces the rear faceplate 2037 when assembled. This notch 2064a engages the snap arm 2037d in the ejected state to prevent removal of the battery compartment 2060 from the speculum. When sufficient force is applied to the operating member 2064 in the retained state, the snap arm 2037d disengages from the bottom of the housing 2062 and the battery compartment 2060 is moved from the retaining state to the ejected state shown in FIGS. 26A-26C.

Figure 26A:
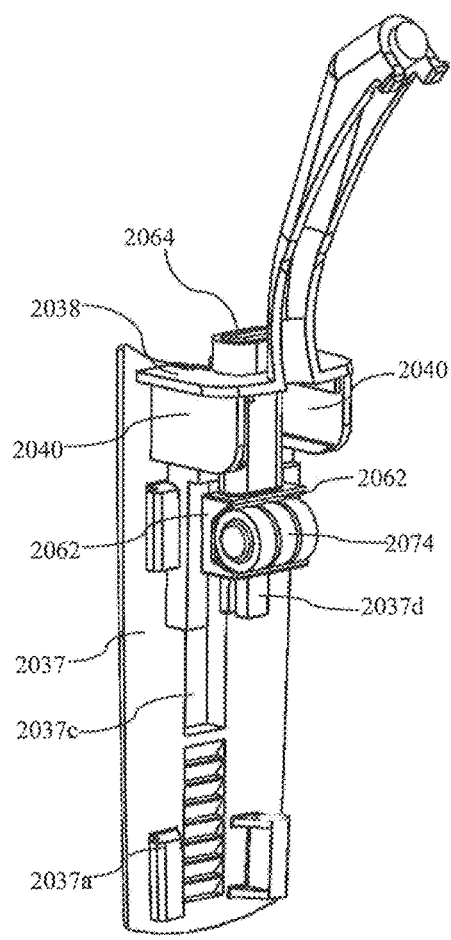
FIGS. 26A-26C show the illumination assembly of FIGS. 25A-25D with the battery compartment in an ejected state.
Figure 26B:
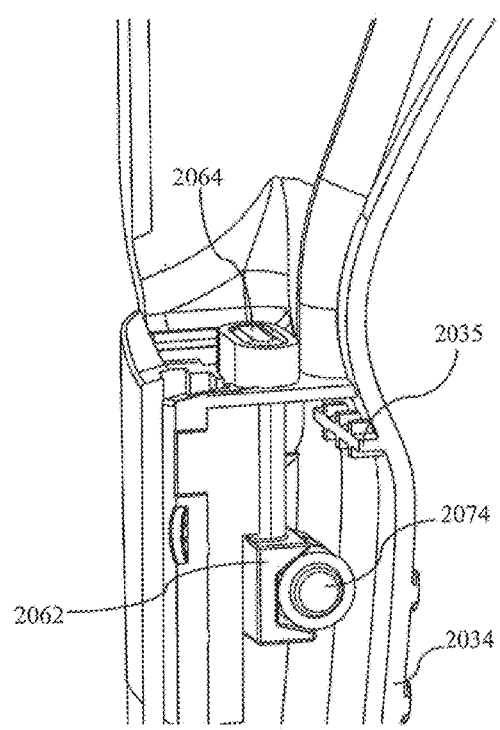
Figure 26C:
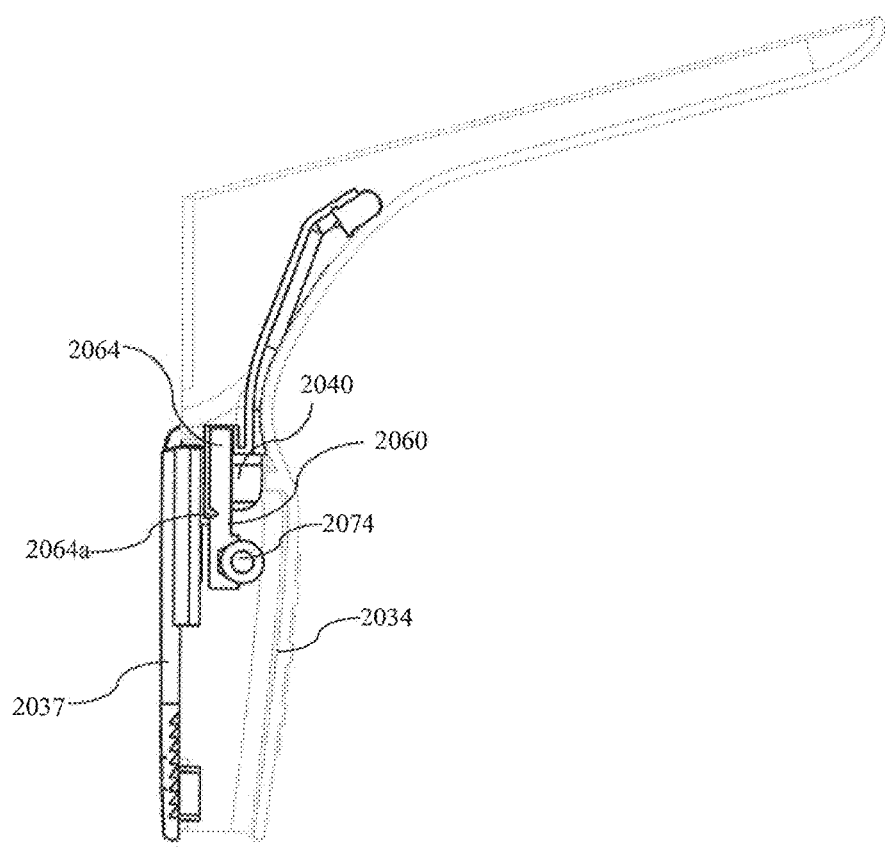
Figure 27:
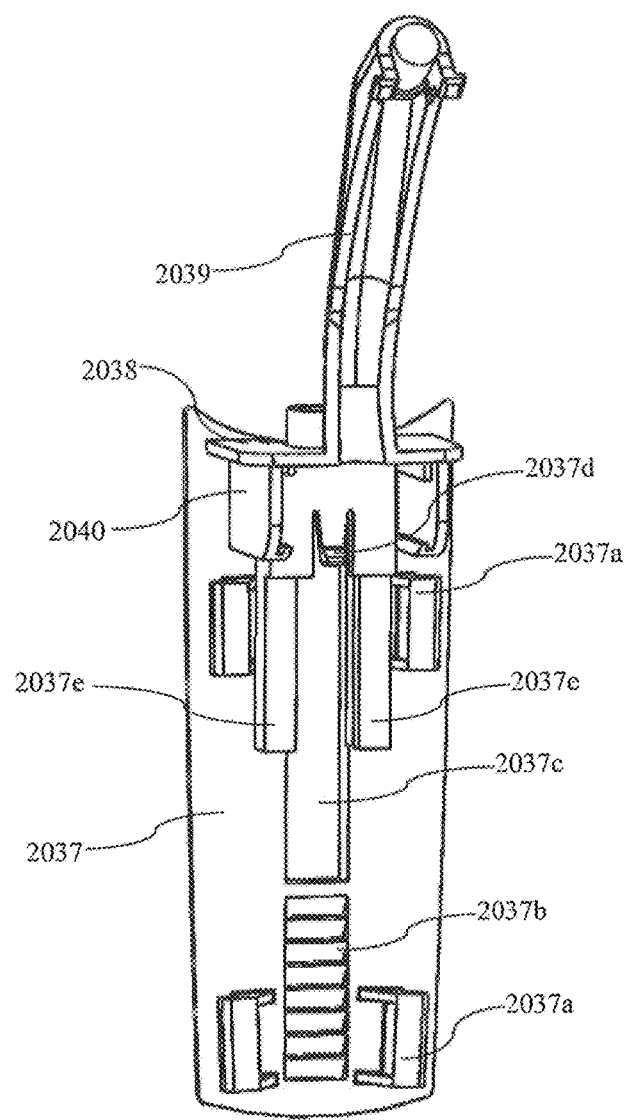
FIG. 27 shows a rear faceplate portion of the illumination assembly of FIGS. 25A-25D without the battery compartment.

FIG. 26A shows the rear face plate assembly 2036 together with the battery compartment 2060 in the ejected state, and FIGS. 26B-26C show a cross-sectional view of the speculum 2000 with the battery compartment 2060 in the ejected state. As can be seen in FIGS. 26A-26C, in the ejected state, the batteries 2074 are no longer pressed against the projection 2035 on the inner surface of the handle and are removed from the space between the sidewalls 2040 that extend from the shelf 2038. Since the batteries are no longer retained on all sides by the housing 2062, the sidewalls 2040 and the projection 2035, they can be easily dislodged from the housing 2062 and removed from the open bottom end of the handle 2034. In the present illustrative embodiment, the handle 2034 is shaped so that the handle is smaller in circumference in the area of the projection 2035 and larger in circumference in the area below the projection 2035. As shown in FIGS. 26B and 26C, the front wall of the handle protrudes outwardly below the projection 2035. This configuration provides additional space for releasing the batteries from the housing 2062 and for allowing the batteries to easily fall through the handle to be removed from the bottom opening in the handle.

Moreover, as can be seen in FIG. 26C, the battery compartment 2060 is locked in place in the ejected state by the snap arm 2037d, which is engaged with the notch 2064a in the operating member 2064. This prevents removal of the battery compartment 2060 together with the batteries, which could contaminate the batteries with biological materials and would require subsequent separation of the battery compartment from the batteries to be recycled.

Although the batteries in the embodiment of FIGS. 24-26 are removed though the open bottom end of the handle, other variations are also contemplated. For example, the batteries may be removed from a cutout formed in one of the sidewalls of the handle 2034 or from a cutout formed in the rear faceplate 2037. In addition, the operating member 2064 in the embodiments of FIGS. 24-26 is configured as a push-button. In other embodiments, a pulling mechanism may instead be used to pull the battery compartment 2060 downward so as to release the batteries from the battery compartment.

Moreover, although FIGS. 24-26 show the battery removal mechanism being used in a speculum, it is understood that this mechanism may be adapted for use in other devices, such as retractors, laryngoscopes, anoscopes, suction devices, and other medical devices. For example, the battery removal mechanism may be adapted for use in a surgical retractor by omitting the upper member 2020 and the linear support member 2050 and using a substantially the same mechanism for battery removal in a retractor that includes a handle 2034, a retractor blade extending at an angle with respect to the handle and the rear faceplate assembly 2036 as described above (similar to FIG. 24B). In another example, the battery removal mechanism may be adapted for use in an anoscope by omitting the upper member 2020 and the linear support member 2050 and by modifying the shape of the lower blade.

Figure 28A:
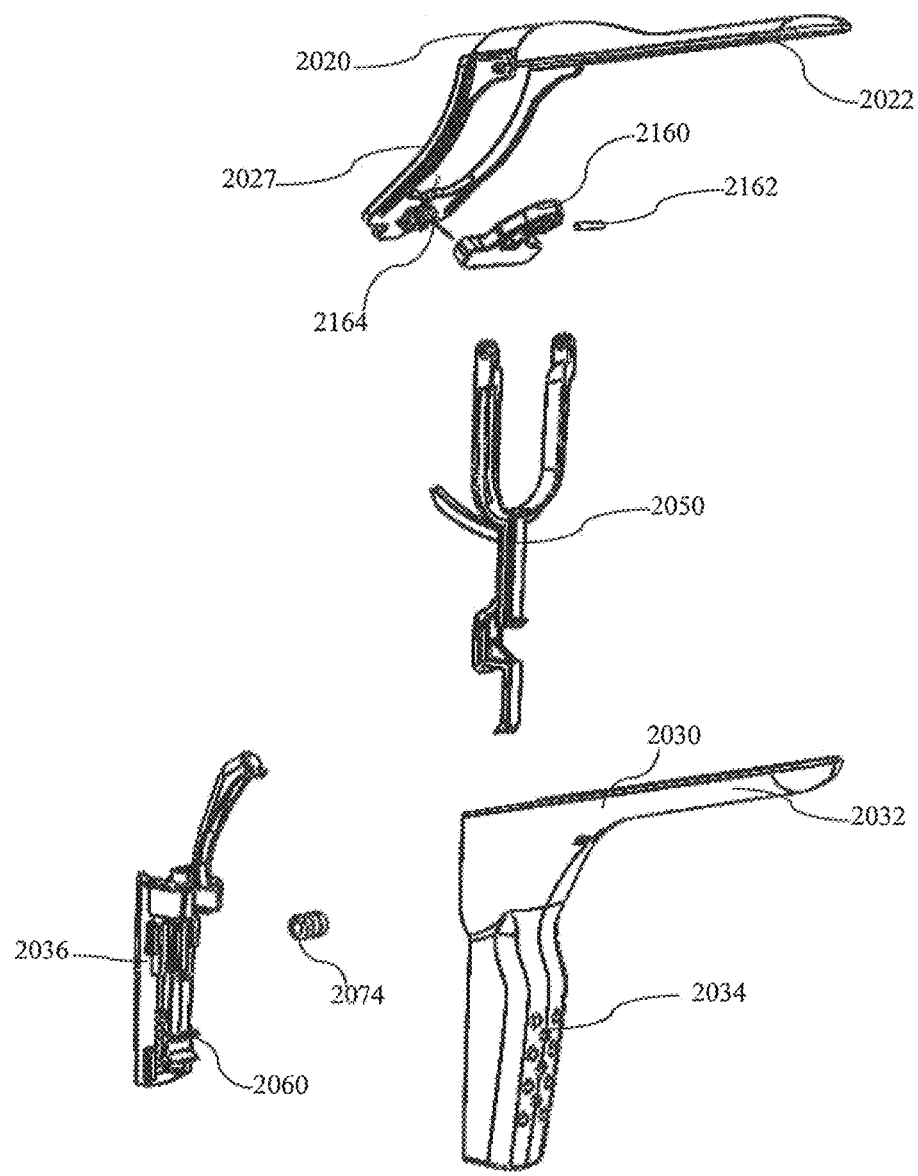
FIG. 28A shows an exploded view of the speculum of FIGS. 24A-27.

The illustrative embodiment of the speculum in FIGS. 24-27 is assembled as shown in FIGS. 28A-28G. FIG. 28A shows an exploded view of the speculum, which includes the lower member 2030 with the handle 2034 and the lower blade 2032, the upper member 2020 with the upper blade 2022 and an operating member 2027, the linear support member 2050, the rear faceplate assembly 2036 together with the battery compartment 2060, batteries 2074, a rocker 2160 for angular adjustment as described above with respect to FIGS. 4-5, a biasing member 2164 and a pivot pin 2162 for attaching the rocker 2160. FIGS. 28B-28G show an illustrative sequence of assembling the speculum of FIGS. 24-27.

Figure 28B:
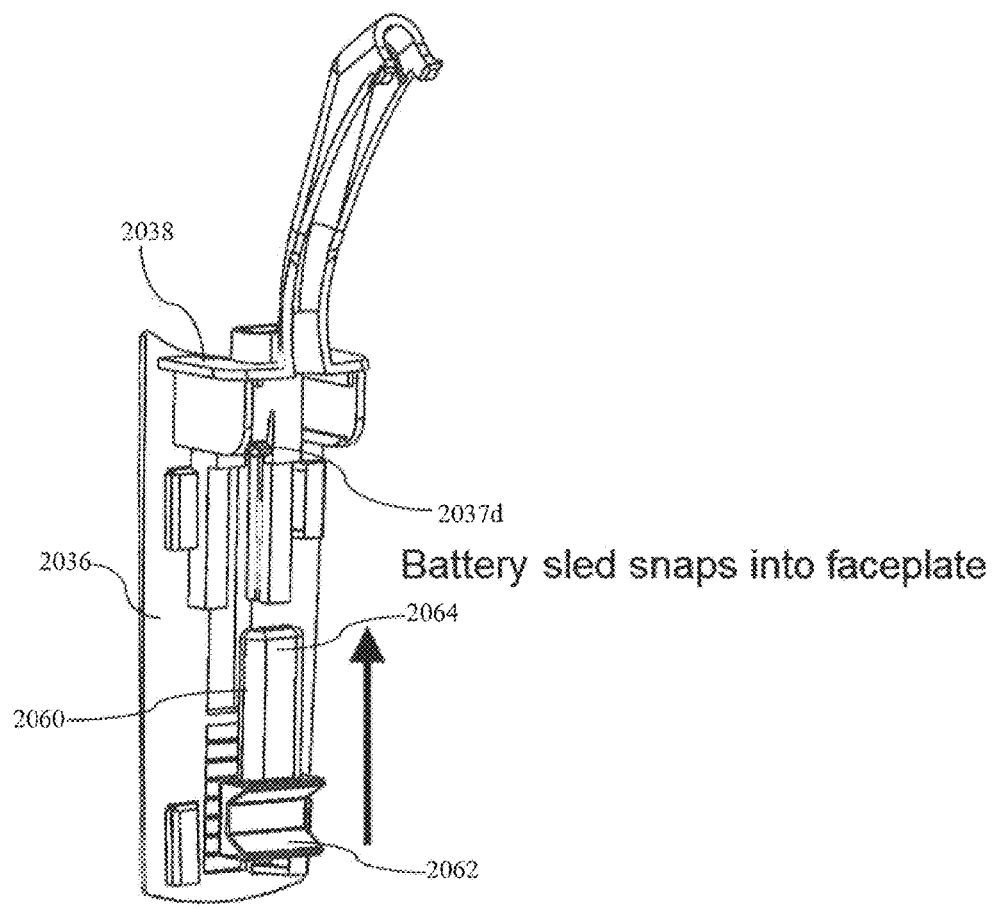
FIGS. 28B-28G show an illustrative sequence of assembling the speculum of FIGS. 24A-27.
Figure 28C:
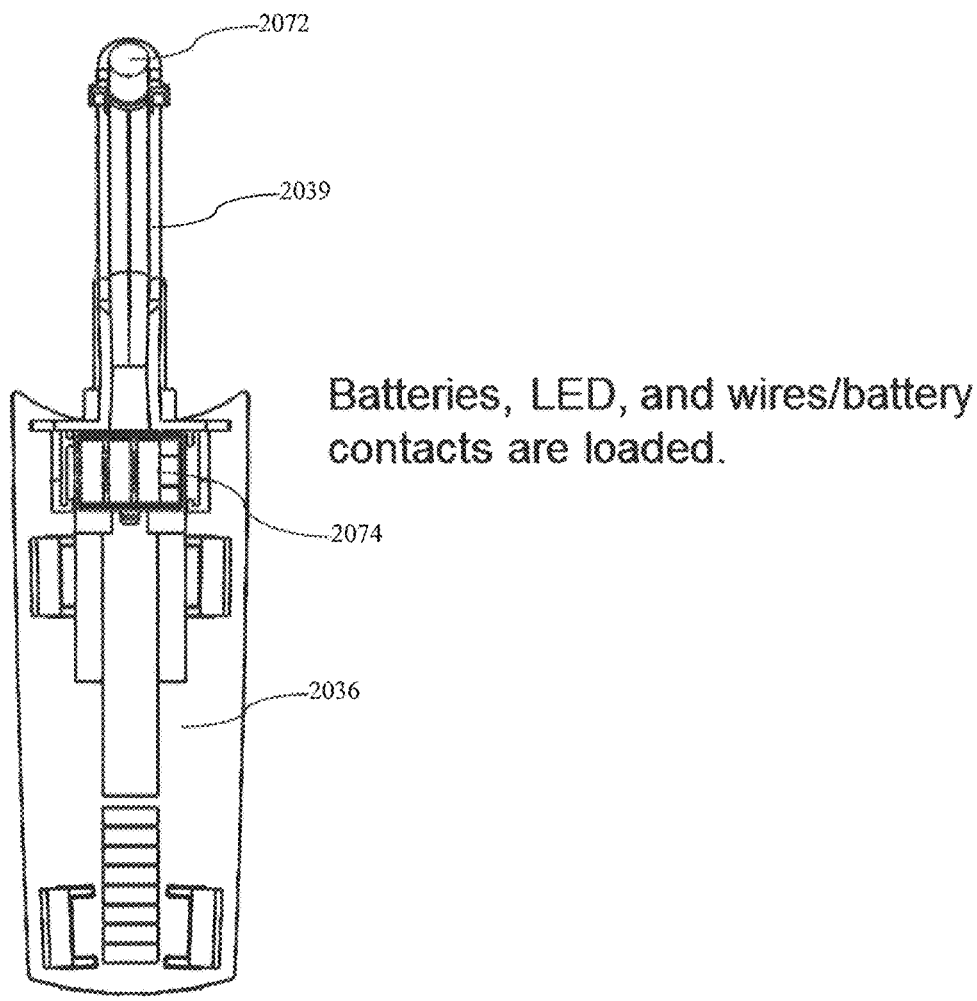

As shown in FIG. 28B, the battery compartment 2060 is assembled with the rear faceplate assembly 2036 by inserting the button 2064 into the opening in the shelf 2038 of the rear faceplate assembly 2036. When the button 2064 is fully inserted into the opening in the shelf 2038, the snap arm 2037d engages with the bottom surface of the housing 2062. After the battery compartment 2060 is snapped in to engage with the rear faceplate assembly 2036, the batteries 2074 are inserted into the housing 2062, as shown in FIG. 28C, and are held by the housing and between the sidewalls 2040 extending from the shelf 2038. At the time of, or prior to, positioning the batteries, battery contacts are loaded to allow for connection of the batteries to wires. In addition, as shown in FIG. 28C, the light source 2072 is positioned to be held by the end of the illumination assembly cover 2039 and the wires are loaded to connect the light source 2072 to the battery contacts and to be enclosed by the illumination assembly cover 2039. As shown in FIG. 28C, the illumination assembly 2070 is assembled together with the rear faceplate assembly 2036 and the battery compartment 2060.

Figure 28D:
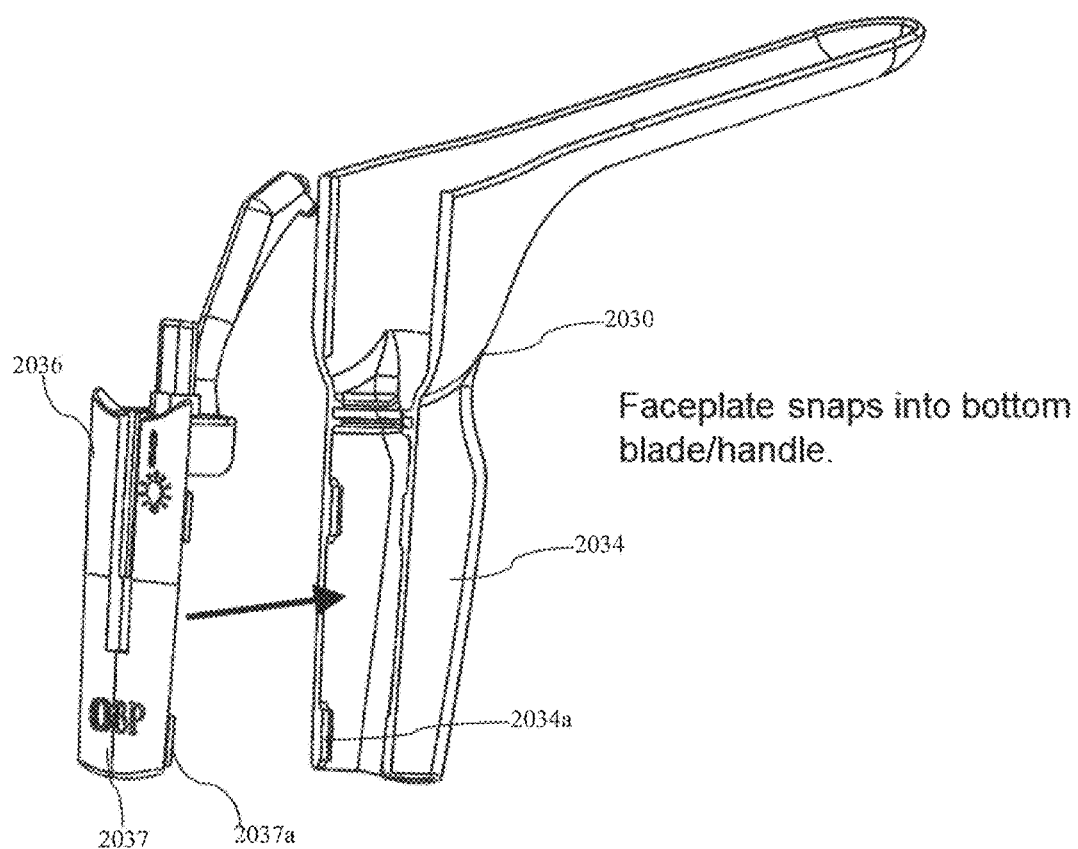

As shown in FIG. 28D, the resulting assembly of FIG. 28C is then assembled together with the lower member 2020. In the illustrative embodiment of FIG. 28D, the rear faceplate assembly 2036 snaps into the rear of the handle 2034 of the lower member 2020 to form the rear wall of the handle 2034. As described above, the engagement protrusions 2037a on the inner surface of the rear faceplate 2037 snap to engage with corresponding protrusions 2034a formed on the inner surface of the handle sidewalls. In other embodiments, other types of engagement may be used for assembling the rear faceplate assembly 2036 with the lower member 2020. For example, the sidewalls of the handle may include channels formed on the inner surfaces thereof for engagement with the engagement protrusions 2037a on the rear faceplate 2037 by sliding the engagement protrusions 2037a into the channels. In other embodiments, the sidewalls of the handle may include recesses for engaging with the engagement protrusions 2037a. In yet other embodiments, the sidewalls of the handle may include protrusions that engage with corresponding recesses formed in the rear faceplate 2037. Other types of engagements may be used for coupling the faceplate assembly 2036 with the lower member 2020.

Figure 28E:
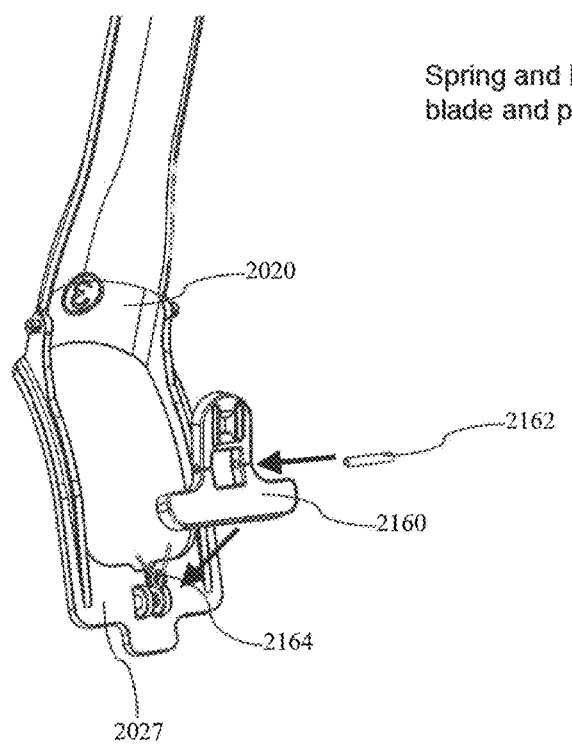

As shown in FIG. 28E, the rocker 2160 of the angular adjustment mechanism is assembled with the operating member 2027. Specifically, the rocker 2160 is positioned with openings therein to align with corresponding openings in the operating member 2027 and a spring 2164 or any other suitable biasing member is positioned between the operating member and the rocker 2160 so as to bias the rocker 2160 in a direction away from the operating member 2027. The pin 2162 is then inserted into the openings in the rocker 2160 and the corresponding openings in the operating member 2027. The ends of the pin 2162 may be flattened or capped to prevent removal of the pin. The biasing member 2164 may be positioned between the operating member 2027 and the rocker 2160 either before or after insertion of the pin to hold the rocker 2160 and the operating member 2027 together.

Figure 28F:
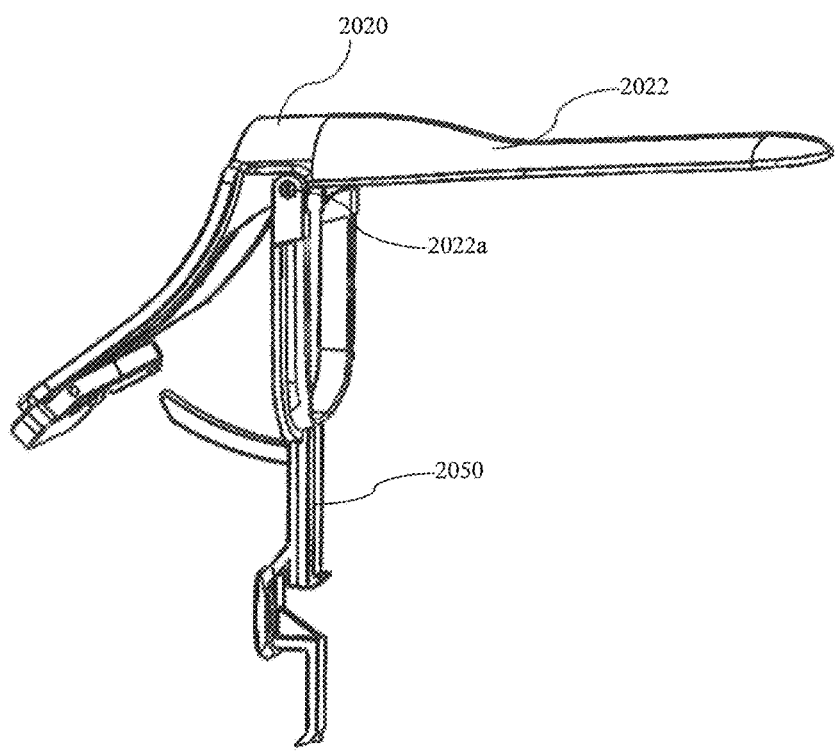
Figure 28G:
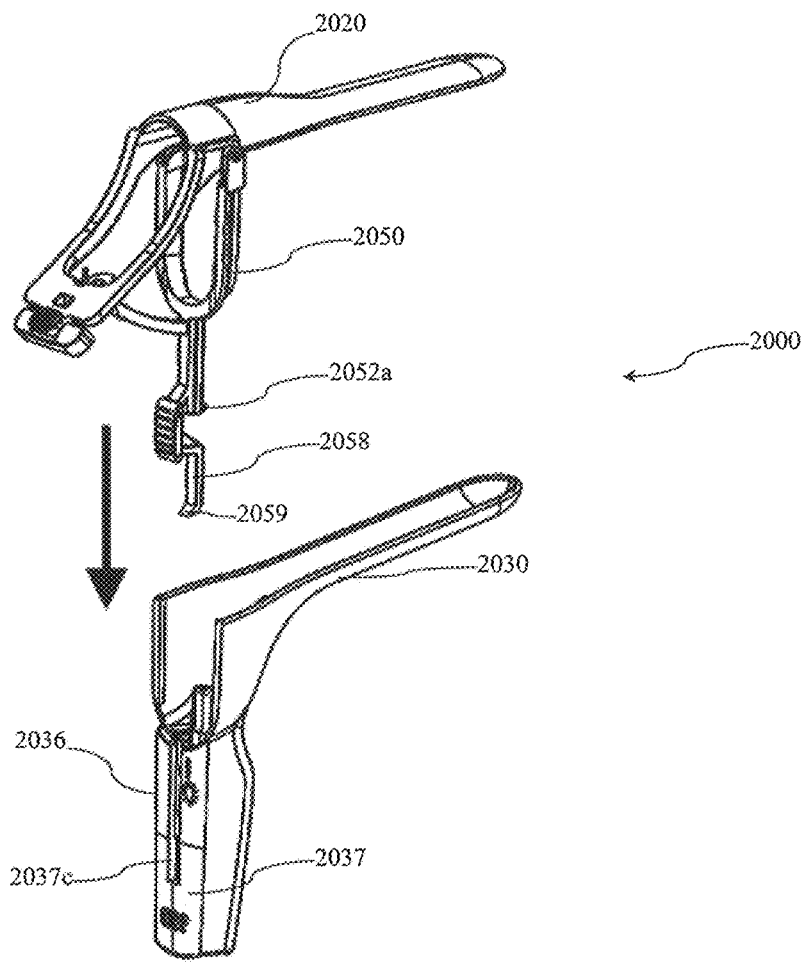

As shown in FIG. 28F, the top member 2020 is assembled together with the linear support member 2050. In the embodiment of FIG. 28F, hinge protrusions 2022a are formed on the outer sides of a proximal end of the upper blade 2022. The linear support member 2050 includes a yoke portion (U-shaped portion) extending from its elongated body with each leg of the yoke portion including an opening for engaging with the corresponding hinge protrusion 2022a. To assemble the upper member 2020 with the linear support member, the hinge protrusions 2022a are snapped into corresponding openings in the yoke portion for a hinge coupling therebetween. In other embodiments, the legs of the yoke portion may include inwardly facing protrusions and the proximal end of the blade 2022 may include corresponding openings for insertion of the protrusions on the yoke portion. Other types of couplings may be used to form a hinge coupling between the upper member 2020 and the linear support member 2050. As shown in FIG. 28G, the top assembly formed in FIG. 28F is then assembled together with the bottom assembly formed in FIG. 28D by inserting the linear support member 2050 into the through recess 2037c formed in the rear faceplate 2037. When the linear support member 2050 is inserted into the through recess 2037c, the engagement arm 2058 of the linear support member 2050 is inserted into the through recess 2037c and slid below the through recess 2037c so that the locking tooth 2059 on the engagement arm 2058 engages with stop tabs formed on the inner surface of the rear faceplate 2037. Also, when the linear support member 2050 is inserted into the through recess 2037c beyond the predetermined position, the retaining projection 2052a on the elongated body 2052 of the linear support member 2050 engages with the rear faceplate assembly 2036 to prevent removal and disengagement of the linear support member 2050 from the rear faceplate assembly 2036. The resulting disposable speculum 2000 has mechanical engagements between the different elements, which makes the speculum easy to assemble and which are sufficiently strong to withstand in-use conditions. The order in which the elements of the speculum 2000 are assembled are not limited to the order shown in FIGS. 28B-28G, and may be varied.

The materials used for forming the speculum of FIGS. 24-28 are similar to those of other speculums shown in other figures and described above. In certain embodiments, the speculum components are formed from plastic materials. Exemplary plastic materials that may be used for constructing the speculum of the present invention include, but are not limited to, polypropylene, polystyrene, and any composite of more than one of these plastics and polymers. The upper and lower members and the rear faceplate assembly may be molded from a colorless transparent or translucent plastic material, such as acrylic plastic, polycarbonate or the like. The rocker may be made from the same or similar materials as the speculum or from metallic materials. The linear support member may be formed from a polyester or polyamide material, such as nylon, or the like. The biasing member (spring) and the pin may be formed from metallic materials or from polymers and plastics. All of these components may be formed by injection molding, extrusion, using a 3D printer or any other suitable technique. In certain embodiments, the materials for forming the speculum, including the upper and lower members, the rear faceplate assembly, the rocker and/or the linear support member, of the present invention include glass-fiber reinforced polymers, polyacrylamide compounds, thermoplastic crystalline polymers, thermoplastic crystalline polymers of aromatic diamines and aromatic dicarboxylic anhydrides, glass-fiber reinforced polyacrylamides, and other materials having sufficient rigidity and strength. Although in the illustrative embodiments, plastic and/or polymer materials are used for the components of the speculum, in other embodiments, some or all of the components may be formed from metallic or fiberglass materials.

Although the embodiments described above are shown with a speculum, it is understood that the battery removal mechanisms may be used with other medical devices that use batteries, either as part of the illumination assembly or as part of another assembly that requires batteries. In addition to the specific embodiments described above, other variations may be made for safe removal of batteries without contaminating them with biological materials, as would be appreciated to those of ordinary skill in the art. Therefore, it is to be understood that other expedients/variations may be employed but that stay within the meaning, scope and spirit of the invention.

In all cases it is understood that the above-described arrangements are merely illustrative of the many possible specific embodiments which represent applications of the present invention. Numerous and varied other arrangements, including use of different materials and various configurations of components of the speculum or another medical device, can be readily devised without departing from the spirit and scope of the invention.

This application claims priority to provisional patent application Nos. 62/649,190 filed on Mar. 28, 2018, 62/574,969 filed on Oct. 20, 2017 and 62/574,412 filed on Oct. 19, 2017, the disclosures of which are incorporated herein by reference.

We claim:

1. A speculum, comprising:
a lower member including a handle and a lower blade extending at an angle from the handle;
an upper blade movably engaged with the lower member by an angular adjustment mechanism so as to allow continuous adjustment of an angle between the upper and lower blades; and
the angular adjustment mechanism comprising:
a guiding arm;
a rotational lever connected to the upper blade and operable by a user to change the angle between the upper and lower blades, the rotational lever being movably engaged with the guiding arm and configured to move relative to the guiding arm to continuously change the angle between the upper and lower blades, and
a locking member movable between a locked position to lock a positional relationship between the rotational lever and the guiding arm and an unlocked position to release a locked positional relationship between the rotational lever and the guiding arm,
wherein the locking member is configured to: (1) automatically lock the positional relationship between the rotational lever and the guiding arm along any position on the guiding arm, (2) automatically release the locked positional relationship during operation of the rotational lever in a first direction, and (3) be manually moved to the unlocked position, without requiring moving of the guiding arm, to permit operation of the rotational lever in a second direction opposite to the first direction.

2. The speculum in accordance with claim 1, wherein the rotational lever is configured to move relative to the guiding arm between a first position corresponding to a closed state of the upper and lower blades and a second position corresponding to a maximum angle between the upper and lower blades, and wherein the rotational lever is configured to be locked relative to the guiding arm at any position within a range from the first position to the second position.

3. The speculum in accordance with claim 1, wherein the guiding arm does not include any ratchet teeth.

4. The speculum in accordance with claim 1, wherein operation of the rotational lever in the first direction causes the angle between the upper and lower blades to increase and wherein the operation of the rotational lever in the first and second directions is substantially silent.

5. The speculum in accordance with claim 1, wherein the locking member comprises a biasing member for biasing the locking member to the locked position.

6. The speculum in accordance with claim 1, wherein:
the locking member comprises a rocker having an opening formed therein, the size of the opening being greater than a thickness of the guiding arm; and
the guiding arm is inserted into the opening formed in the rocker so that when the locking member is in the unlocked position, the guiding arm is allowed to slide through the opening in the rocker, and when the locking member is in the locked position, the guiding arm engages with sidewalls of the opening in the rocker to prevent the guiding arm from sliding through the opening in the rocker.

7. The speculum in accordance with claim 6, wherein the rocker is biased to the locked position and is configured to be manually operated to pivot to the unlocked position.

8. The speculum in accordance with claim 1, wherein engagement between the rotational lever and the guiding arm is maintained when the locking member is in the locked position and when the locking member is in the unlocked position.

9. The speculum in accordance with claim 1, wherein the guiding arm extends from the lower member and the rotational lever extends from a proximal end of the upper blade.

10. The speculum in accordance with claim 9, further comprising a linear support member slidably engaged with the lower member and hingedly engaged with the proximal end of the upper blade,
wherein the linear support member is configured to allow linear adjustment of a vertical distance between the upper blade and the lower blade, and the guiding arm extends from the linear support member.

11. The speculum in accordance with claim 10, wherein the handle includes a plurality of teeth formed thereon, and the linear support member includes a locking projection configured to engage with each tooth, the plurality of teeth defining corresponding fixed open states and a closed state for linear adjustment of the vertical distance between the upper blade and the lower blade.

12. The speculum in accordance with claim 11, wherein the plurality of teeth are formed on an inner surface of the handle and a portion of the linear support member is disposed inside the handle so that the locking projection engages with said plurality of teeth.

13. The speculum in accordance with claim 10, further comprising an illumination assembly including at least one light source disposed adjacent to the lower blade, at least one battery provided in the handle, and a battery ejection mechanism for removal of the at least one battery from the handle.

14. The speculum in accordance with claim 13, wherein said battery ejection mechanism comprises a housing for holding the at least one battery in a retained state and an operating member configured to be operated by a user to cause the housing to move from the retained state to an ejected state, and wherein the at least one battery is released from the housing in the ejected state for removal from the handle.

15. The speculum in accordance with claim 14, wherein the housing includes an open side and wherein in the retained state, the at least one battery is retained within the housing by abutting an inner surface of the handle.

16. The speculum in accordance with claim 15, wherein the handle includes a projection formed on the inner surface thereof, the projection abutting the at least one battery in the retained state.

17. The speculum in accordance with claim 14, wherein:
the handle includes a main body having an open rear side and a rear faceplate configured to engage with the main body and to cover the open rear side of the main body;
the battery ejection mechanism is engaged with the rear faceplate of the handle, and
the rear faceplate further includes an illumination assembly cover for enclosing electrical connections between the at least one battery and the at least one light source and for partially enclosing the at least one light source.

18. The speculum in accordance with claim 1, wherein the angle between the handle and the lower member is between 95 and 120 degrees.

19. A speculum comprising:
a lower member including a handle and a lower blade extending at an angle from the handle;
an upper blade movably engaged with the lower member by an angular adjustment mechanism for adjustment of an angle between the upper and lower blades; and
the angular adjustment mechanism configured to allow continuous adjustment of the angle between the upper and lower blades to any angle within a predetermined range from a closed state to a maximum angle between the upper and lower blades,
wherein the angular adjustment mechanism comprises a lever mechanism for continuously adjusting the angle between the upper and lower blades and a rocker pivotably mounted on the lever mechanism, the rocker is configured to be pivotable between a locked position that locks the lever mechanism and a positional relationship between the upper and lower blades and an unlocked position that unlocks the lever mechanism and releases a locked positional relationship between the upper and lower blades,
wherein the rocker is configured to: (1) automatically lock the positional relationship between the upper and lower blades at any selected angle within the predetermined range, (2) automatically release the locked positional relationship between the upper and lower blades when the angular adjustment mechanism is operated to increase the angle between the upper and lower blades, and (3) be manually moved to the unlocked position to permit operation of the angular adjustment mechanism to decrease the angle between the upper and lower blades.

20. The speculum in accordance with claim 19, wherein the rocker is biased to the locked position and is configured to be manually operated to the unlocked position.

21. The speculum in accordance with claim 19, further comprising an illumination assembly including at least one light source disposed adjacent to the lower blade, at least one battery provided in the handle, and a battery ejection mechanism for removing the at least one battery from the handle.

22. A speculum comprising:
a lower member including a handle having a proximal end and a distal end and a lower blade extending at an angle from the proximal end of the handle;
an upper blade movably engaged with the lower member by an angular adjustment mechanism so as to allow adjustment of an angle between the upper and lower blades;
and an illumination assembly including at least one light source, at least one battery provided in the handle and a battery ejection mechanism for removal of the at least one battery from the handle via an opening formed in the handle,
wherein the battery ejection mechanism includes an operating member configured to be operated by a user to cause the at least one battery to be released from the handle,
wherein the battery ejection mechanism remains attached to the speculum after the at least one battery has been released,
wherein the battery ejection mechanism comprises a housing for holding the at least one battery in a retained state and when the operating member is operated by a user, the housing is caused to move from the retained state to an ejected state, wherein the at least one battery is released from the housing in the ejected state for removal from the handle, and wherein at least a portion of the housing is positioned within the handle in the retained state and the ejected state,
wherein the housing includes an open side and wherein in the retained state, the at least one battery is retained within the housing by a wall of the handle, and
wherein: the handle includes a main body having an open rear side and a rear faceplate configured to be engaged with the main body and to cover the open rear side of the main body, the battery ejection mechanism is engaged with the rear faceplate of the handle, and the at least one battery is retained within the housing by a front wall of the main body.

23. The speculum in accordance with claim 22, wherein when the operating member is operated by a user, the at least one battery is released from the handle without the at least one battery coming into contact with the user and without the at least one battery coming into contact with external surfaces of the speculum.

24. The speculum according to claim 22, wherein the opening is formed at a distal end of the handle and wherein in the retained state, the housing retains the at least one battery adjacent the proximal end of the handle.

25. The speculum according to claim 22, wherein the angular adjustment mechanism is configured to allow continuous and click-free adjustment of the angle between the upper and the lower blades to any angle within a predetermined range from a closed state to a maximum angle between the upper and lower blades.

26. A speculum, comprising:
   a lower blade and an upper blade; and
   an angular adjustment mechanism configured to allow continuous adjustment of an angle between the upper and lower blades, the angular adjustment mechanism comprising:
   a guiding arm;
   a rotational lever connected to the upper blade, the rotational lever configured to be operable to adjust the angle between the upper blade and the lower blade and configured to move relative to the guiding arm to continuously change the angle between the upper and lower blades; and
   a lock configured to be movable between a first position that locks the upper blade and the lower blade at an angle and a second position that unlocks the upper blade and the lower blade from a locked angle,
   wherein the lock is configured to, in the first position, automatically lock the rotational lever at any point along the guiding arm, and
   wherein the lock is a distinct component from the rotational lever and the guiding arm.

27. The speculum according to claim 26, wherein when the lock is in the first position, the rotational lever is movable in a first direction to increase the angle between the upper and lower blades and not movable in a second direction to decrease the angle between the upper and lower blades.

\* \* \* \* \*